US008642330B2

(12) United States Patent
Rock et al.

(10) Patent No.: US 8,642,330 B2
(45) Date of Patent: Feb. 4, 2014

(54) ANTIBODY COMPOSITIONS, METHODS FOR TREATING NEOPLASTIC DISEASE AND METHODS FOR REGULATING FERTILITY

(75) Inventors: Edwin P. Rock, Strafford, PA (US);
Vernon C. Stevens, Dublin, OH (US);
Pierre L. Triozzi, Shaker Heights, OH (US)

(73) Assignee: Onconon, LLC, Washington, DC (US)

( * ) Notice: Subject to any disclaimer, the term of this patent is extended or adjusted under 35 U.S.C. 154(b) by 770 days.

(21) Appl. No.: 12/063,371

(22) PCT Filed: Aug. 8, 2006

(86) PCT No.: PCT/US2006/030988
§ 371 (c)(1),
(2), (4) Date: Sep. 24, 2009

(87) PCT Pub. No.: WO2007/019541
PCT Pub. Date: Feb. 15, 2007

(65) Prior Publication Data
US 2010/0068135 A1 Mar. 18, 2010
US 2012/0141371 A2 Jun. 7, 2012

Related U.S. Application Data

(60) Provisional application No. 60/706,506, filed on Aug. 8, 2005.

(51) Int. Cl.
*C12N 5/16* (2006.01)
*C12N 5/07* (2010.01)
*C12N 15/02* (2006.01)
*C12N 15/08* (2006.01)
*C12N 15/06* (2006.01)
*C12P 21/08* (2006.01)
*C07K 16/00* (2006.01)

(52) U.S. Cl.
USPC ......... 435/326; 435/449; 435/452; 530/388.1

(58) Field of Classification Search
None
See application file for complete search history.

(56) References Cited

U.S. PATENT DOCUMENTS

| 3,791,932 | A | 2/1974 | Schuurs et al. |
|---|---|---|---|
| 3,817,837 | A | 6/1974 | Rubenstein et al. |
| 3,839,153 | A | 10/1974 | Schuurs et al. |
| 3,850,578 | A | 11/1974 | McConnell |
| 3,850,752 | A | 11/1974 | Schuurs et al. |
| 3,853,987 | A | 12/1974 | Dreyer |
| 3,867,517 | A | 2/1975 | Ling |
| 3,879,262 | A | 4/1975 | Schuurs et al. |
| 3,901,654 | A | 8/1975 | Gross |
| 3,935,074 | A | 1/1976 | Rubenstein et al. |
| 3,939,350 | A | 2/1976 | Kronick et al. |
| 3,984,533 | A | 10/1976 | Uzgiris |
| 3,996,345 | A | 12/1976 | Ullman et al. |
| 4,034,074 | A | 7/1977 | Miles |
| 4,098,876 | A | 7/1978 | Piasio et al. |
| 4,275,149 | A | 6/1981 | Litman et al. |
| 4,277,437 | A | 7/1981 | Maggio |
| 4,366,241 | A | 12/1982 | Tom et al. |
| 4,376,110 | A | 3/1983 | David et al. |
| 4,391,904 | A | 7/1983 | Litman et al. |
| 4,399,216 | A | 8/1983 | Axel et al. |
| 4,486,530 | A | 12/1984 | David et al. |
| 4,565,687 | A | 1/1986 | Khazaeli |
| 4,681,581 | A | 7/1987 | Coates |
| 4,683,195 | A | 7/1987 | Mullis et al. |
| 4,683,202 | A | 7/1987 | Mullis |
| 4,735,210 | A | 4/1988 | Goldenberg |
| 4,740,461 | A | 4/1988 | Kaufman |
| 4,804,626 | A | 2/1989 | Bellet |
| 4,816,567 | A | 3/1989 | Cabilly et al. |
| 4,851,356 | A | 7/1989 | Canfield |
| 4,912,040 | A | 3/1990 | Kaufman et al. |
| 4,959,455 | A | 9/1990 | Clark et al. |
| 5,101,827 | A | 4/1992 | Goldenberg |
| 5,102,990 | A | 4/1992 | Rhodes |
| 5,194,594 | A | 3/1993 | Kawli et al. |
| 5,401,629 | A | 3/1995 | Harpold et al. |
| 5,436,128 | A | 7/1995 | Harpold et al. |
| 5,530,101 | A | 6/1996 | Queen et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,585,089 | A | 12/1996 | Queen et al. |
| 5,591,669 | A | 1/1997 | Krimpenfort et al. |
| 5,612,205 | A | 3/1997 | Kay et al. |
| 5,625,126 | A | 4/1997 | Lonberg et al. |

(Continued)

FOREIGN PATENT DOCUMENTS

| EP | 0338841 | B1 | 10/1989 |
|---|---|---|---|
| EP | 0216846 | B1 | 1/1990 |

(Continued)

OTHER PUBLICATIONS

Paul, Fundamental Immunology, 3rd Edition, 1993, pp. 292-295.*
Rudikoff et al., Proc. Natl. Acad. Sci. USA, 79(6):1979-1983, Mar. 1982.*
Colman, Research in Immunology, 145:33-36, 1994.*
Bendig, Methods: A Companion to Methods in Enzymology, 1995; 8:83-93.*
[Fundamental Immunology 242 (William E. Paul, M.D. ed., 3d ed. 1993)].*
Acevedo, H.F. et al., "Expression of Membrane-Associated Human Chorionic Gonadotropin, Its Subunits, and Fragments by Cultured Human Cancer Cells," *Cancer*, Apr. 1, 1992, pp. 1829-1842, vol. 69, No. 7.
Acevedo, H.F., "Human Chorionic Gonadotropin (hCG), The Hormone of Life and Death: a Review," *Journal of Experimental Therapeutics and Oncology*, 2002, pp. 133-145, vol. 2, No. 133.

(Continued)

*Primary Examiner* — Hong Sang
(74) *Attorney, Agent, or Firm* — Fenwick & West LLP

(57) ABSTRACT

Antibody compositions and methods for inhibition of the effects of gonadotropin hormones are provided. Methods for treating cancer and methods for regulating fertility are provided by administration of the antibody compositions to a mammalian subject in need thereof.

6 Claims, 12 Drawing Sheets

(56) References Cited

U.S. PATENT DOCUMENTS

| | | | |
|---|---|---|---|
| 5,625,825 A | 4/1997 | Rostoker et al. |
| RE35,500 E | 5/1997 | Rhodes |
| 5,633,425 A | 5/1997 | Lonberg et al. |
| 5,643,763 A | 7/1997 | Dunn et al. |
| 5,648,471 A | 7/1997 | Buttram et al. |
| 5,661,016 A | 8/1997 | Lonberg et al. |
| 5,674,727 A | 10/1997 | Cole |
| 5,693,761 A | 12/1997 | Queen et al. |
| 5,693,792 A | 12/1997 | Torii et al. |
| 5,697,902 A | 12/1997 | Goldenberg |
| 5,714,350 A | 2/1998 | Co et al. |
| 5,721,367 A | 2/1998 | Kay et al. |
| 5,733,743 A | 3/1998 | Johnson et al. |
| 5,741,957 A | 4/1998 | Deboer et al. |
| 5,750,172 A | 5/1998 | Meade et al. |
| 5,756,687 A | 5/1998 | Denman et al. |
| 5,770,429 A | 6/1998 | Lonberg et al. |
| 5,777,085 A | 7/1998 | Co et al. |
| 5,789,215 A | 8/1998 | Berns et al. |
| 5,789,650 A | 8/1998 | Lonberg et al. |
| 5,814,318 A | 9/1998 | Lonberg et al. |
| 5,827,690 A | 10/1998 | Meade et al. |
| 5,869,057 A | 2/1999 | Rock |
| 5,914,241 A | 6/1999 | Valkirs |
| 5,939,598 A | 8/1999 | Kucherlapati et al. |
| 5,965,375 A | 10/1999 | Valkirs |
| 5,997,871 A | 12/1999 | Gallo |
| 6,025,149 A | 2/2000 | Cuckle |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,339,143 B1 | 1/2002 | Krichevsky |
| 6,403,326 B1 | 6/2002 | Acevedo |
| 6,429,018 B1 | 8/2002 | Cole |
| 6,469,139 B1 | 10/2002 | Roitt |
| 6,503,723 B1 | 1/2003 | Van Lune et al. |
| 6,627,457 B2 | 9/2003 | Pandian |
| 6,673,986 B1 | 1/2004 | Kucherlapati et al. |
| 6,699,834 B1 | 3/2004 | Gallo |
| 6,716,428 B1 | 4/2004 | Stevens |
| 6,764,680 B1 | 7/2004 | Iversen |
| 6,927,034 B2 | 8/2005 | O'Connor |
| 2002/0128190 A1 | 9/2002 | Lobel et al. |
| 2003/0049273 A1 | 3/2003 | Gallo et al. |
| 2003/0092082 A1 | 5/2003 | Acevedo |
| 2004/0072731 A1 | 4/2004 | McMichael |
| 2005/0142135 A1 | 6/2005 | Ji |
| 2005/0260196 A1 | 11/2005 | Cole |
| 2006/0040855 A1 | 2/2006 | Moyle |
| 2006/0073571 A1 | 4/2006 | Saxena et al. |
| 2006/0121010 A1 | 6/2006 | Iverson |

FOREIGN PATENT DOCUMENTS

| | | |
|---|---|---|
| EP | 0256055 B1 | 8/1991 |
| EP | 0323997 B1 | 4/1993 |
| EP | 0463151 B1 | 6/1996 |
| EP | 0546073 B1 | 9/1997 |
| JP | 11-089569 | 4/1999 |
| WO | WO 91/17271 | 11/1991 |
| WO | WO 92/01047 | 1/1992 |
| WO | WO 92/02190 | 2/1992 |
| WO | WO 92/03918 | 3/1992 |
| WO | WO 92/12645 | 8/1992 |
| WO | WO 92/22647 | 12/1992 |
| WO | WO 93/12227 | 6/1993 |
| WO | WO 94/00569 | 1/1994 |
| WO | WO 94/02602 | 2/1994 |
| WO | WO 96/14436 | 5/1996 |
| WO | WO 96/34096 | 10/1996 |
| WO | WO 97/08320 | 3/1997 |
| WO | WO 97/13852 | 4/1997 |
| WO | WO 97/38137 | 10/1997 |
| WO | WO 00/37504 | 6/2000 |
| WO | WO 01/14424 | 3/2001 |
| WO | WO 01/24765 | 4/2001 |
| WO | WO 2005/079489 | 9/2005 |
| WO | WO 2005/095458 | 10/2005 |

OTHER PUBLICATIONS

Acevedo, H.F. et al., "Metastatic Phenotype Correlates with High Expression of Membrane-Associated Complete β-Human Chorionic Gonadotropin in Vivo," *Cancer*, Dec. 1, 1996, pp. 2388-2399, vol. 78, No. 11.

Aggrawal et al., eds., *Human Cytokines: Handbook for Basic & Clinical Research*, 1991, Blackwell Scientific Publications, Boston, Mass., (cover page and table of contents).

Ascoli, M. et al., "The Lutropin/Choriogonadotropin Receptor, a 2002 Perspective," *Endocrine Reviews*, 2002, pp. 141-174, vol. 23, No. 2.

Belagaje, R. et al., "Total Synthesis of a Tyrosine Suppressor Transfer RNA Gene," *The Journal of Biological Chemistry*, 1979, pp. 5765-5780, vol. 254, No. 13.

Birken, S. et al., "Isolation and Characterization of Human Pituitary Chorionic Gonadotropin," *Endocrinology*, 1996, pp. 1402-1411, vol. 137, No. 4.

Birken, S. et al., "Development and Characterization of Antibodies to a Nicked and Hyperglycosylated Form of hCG from a Choriocarcinoma Patient," *Endocrine*, Apr. 1999, pp. 137-144, vol. 10, No. 2.

Birken, S. et al., "Immunochemical Measurement of Early Pregnancy Isoforms of hCG: Potential Applications to Fertility Research, Prenatal Diagnosis, and Cancer," *Archives of Medical Research*, 2001, pp. 635-643, vol. 32.

Birken, S. et al., "Preparation and Characterization of New WHO Reference Reagents for Human Chorionic Gonadotropin and Metabolites," *Clinical Chemistry*, 2003, pp. 144-154, vol. 49, No. 1.

Birken, S., "Specific Measurement of O-Linked Core 2 Sugar-Containing Isoforms of Hyperglycosylated Human Chorionic Gonadotropin by Antibody B152," *Tumor Biology*, 2005, pp. 131-141, vol. 26.

Blake, J. et al., "Evaluation of Peptide Libraries: An Iterative Strategy to Analyze the Reactivity of Peptide Mixtures with Antibodies," *BioConjugate Chem*, 1992, pp. 510-513, vol. 3.

Burtrum, D. et al, "A Fully Human Monoclonal Antibody to the Insulin-Like Growth Factor I Receptor Blocks Ligand-Dependent Signaling and Inhibits Human Tumor Growth in Vivo," *Cancer Research*, Dec. 15, 2003, pp. 8912-8921, vol. 63.

Bowie, J.U. et al., "A Method to Identify Protein Sequences that Fold into a Known Three-Dimensional Structure," *Science*, Jul. 12, 1991, pp. 164-170, vol. 253, No. 5016.

Butler, S.A. et al., "The β-Subunit of Human Chorionic Gonadotropin Exists as a Homodimer," *Journal of Molecular Endocrinology*, 1999, pp. 185-192, vol. 22.

Butler, S.A. et al., "The Increase in Bladder Carcinoma Cell Population Induced by the Free Beta Subunit of Human Chorionic Gonadotropin is a Result of an Anti-Apoptosis Effect and Not Cell Proliferation," *British Journal of Cancer*, 2000, pp. 1553-1556, vol. 82, No. 9.

Butler, S.A. et al., "Ectopic Human Chorionic Gonadotropin β Secretion by Epithelial Tumors and Human Chorionic Gonadotropin β-Induced Apoptosis in Kaposi's Sarcoma: Is There a Connection?" *Clinical Cancer Research*, Oct. 15, 2003, pp. 4666-4673, vol. 9.

Butler, S.A. et al., "Reduction of Bladder Cancer Cell Growth in Response to hCGβ CTP37 Vaccinated Mouse Serum," *Oncology Research*, 2003, pp. 93-100, vol. 14.

Butler, S.A. et al., "The Free Monomeric Beta Subunit of Human Chorionic Gonadotrophin (hCGβ) and the Recently Identified Homodimeric Beta-Beta Subunit (hCGββ) Both Have Autocrine Growth Effects," *Tumor Biology*, 2004, pp. 18-23, vol. 25.

Cevc, G. et al., "Ultraflexible vesicles, Transfersomes, have an extremely low pore penetration resistance and transport therapeutic amounts of insulin across the intact mammalian skin," *Biochimica et Biophyssica Acta*, 1998, pp. 201-215, vol. 1368.

(56) References Cited

OTHER PUBLICATIONS

Chaudhary, V.K. et al., "A Rapid Method of Cloning Functional Variable-Region Antibody Genes in *Escherichia coli* as Single-Chain Immunotoxins," *Proc. Natl. Acad. Sci. USA*, Feb. 1990, pp. 1066-1070, vol. 87.

Chen, H-C. et al., "Characterization and Biological Properties of chemically Deglycosylated Human Chorionic Gonadotropin," *The Journal of Biological Chemistry*, Dec. 10, 1982, pp. 14446-14452, vol. 257, No. 23.

Chen, S-Y. et al., "Intracellular Antibodies as a New Class of Therapeutic Molecules for Gene Therapy," *Human Gene Therapy*, 1994, vol. 5, pp. 595-601.

Chiswell, D. et al., "Phage Antibodies: Will New 'Coloclonal' Antibodies Replace Monoclonal Antibodies?," *TIBTECH*, Mar. 1992, vol. 10, pp. 80-84.

Chothia, C. et al., "Canonical Structures for the Hypervariable Regions of Immunoglobulins," *J. Mol. Biol.*, 1987, pp. 901-917, vol. 196.

Chothia, C. et al., "Conformations of Immunoglobulin Hypervariable Regions," Nature, Dec. 21-28, 1989, pp. 877- 883, vol. 342.

Cole, L.A. et all, "The Deactivation of hCG by Nicking and Dissociation," *Journal of Clinical Endocrinology and Metabolism*, 1993, p. 704-710, vol. 96, No. 3.

Cole, L.A. et al., "Gestational Trophoblastic Diseases: 1. Pathophysiology of Hyperglycosylated hCG," *Gynecologic Oncology*, 2006, pp. 145-150, vol. 102.

Cosgrove, D.E. et al., "Chorionic Gonadotropin Synthesis by Human Tumor Cell Lines: Examination of Subunit Accumulation, Steady-State Levels of mRNA, and Gene Structure," *Biochimica et Biophysica Acta*, 1989, pp. 44-54, vol. 1007, Elsevier.

Cwirla, S.E., "Peptides on Phage: A Vast Library of Peptide for Identifying Ligands," *Proc. Natl. Acad. Sci. USA*, Aug. 1990, pp. 6378-6382, vol. 87.

Dirnhofer, S. et al., "Functional and Immunological Relevance of the COOH-Terminal Extension of Human Chorionic Gonadotropin Beta: Implications for the WHO Birth Control Vaccine," *The FASEB Journal*, Nov. 1993, pp. 1381-1385, vol. 7.

Dranoff, G. et al., "Vaccination with Irradiated Tumor Cells Engineered to Secrete Murine Granulocyte-Macrophage Colony-Stimulating Factor Stimulates Potent, Specific, and Long-Lasting Anti-Tumor Immunity," *Proc. Natl. Acad. Sci. USA*, Apr. 1993, pp. 3539-3543, vol. 90.

Elchalal, U. et al., "The Pathophysiology of Ovarian Hyperstimulation Syndrome—Views and Ideas," *Human Reproduction*, 1997, pp. 1129-1137, vol. 12, No. 6.

Evans, B.E., et al., "Design of Nonpeptidal Ligands for a Peptide Receptor: Cholecystokinin Antagonists," *J. Med. Chem.*, 1987, pp. 1229-1239, vol. 30.

European Patent Office Extended Search Report, European Application No. 06813343.8, Apr. 8, 2009, 9 pages.

European Patent Office Communication, European Application No. 06813343.8, Nov. 30, 2010, 1 page.

Fanger, M. et al., "Production and Use of Anti-FcR Bispecific Antibodies," *Immunomethods*, 1994, pp. 72-81, vol. 4.

Fauchere, J-L., "Elements for the Rational Design of Peptide Drugs," *Advances in Drug Research*, 1986, pp. 29-69, vol. 15.

Felici, F. et al., "Selection of Antibody Ligands from a Large Library of Oligopeptides Expressed on a Multivalent Exposition Vector," *J. Mol. Biol.*, 1991, pp. 301-310, vol. 222.

Filicori, M. et al., "Novel Concepts of Human Chorionic Gonadotropin: Reproductive System Interactions and Potential in the Management of Infertility," *Fertility and Sterility*, Aug. 2005, pp. 275-284, vol. 84, No. 2.

Fotinou, C. et al., "Structure of a Fab Fragment Against a C-Terminal Peptide of hCG at 2.0 Å Resolution," *The Journal of Biological Chemistry*, Aug. 28, 1998, pp. 22515-22518, vol. 273, No. 35.

Fry, D.W. et al., "Specific, Irreversible Inactivation of the Epidermal Growth Factor Receptor and erbB2, by a New Class of Tyrosine Kinase Inhibitor," *Proc. Natl. Acad. Sci. USA*, Sep. 1998, pp. 12022-12027, vol. 95.

Furet, P. et al., "Modelling Study of Protein Kinase Inhibitors: Binding Mode of Staurosporine and Origin of the Selectivity of CGP 52411," *Journal of Computer-Aided Molecular Design*, 1995, pp. 465-472, vol. 9.

Gao, C. et al., "A Method for the Generation of Combinatorial Antibody Libraries Using pIX Phage Display," *Proc. Natl. Acad. Sci. U.S.A.*, 2001, pp. 12612-12616, vol. 99.

Geissler, M. et al., "Genetic Immunization with the Free Human Chorionic Gonadotropin β Subunit Elicits Cytotoxic T Lymphocyte Responses and Protects Against Tumor Formation in Mice," *Laboratory Investigation*, 1997, pp. 859-871, vol. 76, No. 6.

Gilman, A., "G Proteins: Transducers of Receptor-Generated Signals," *Ann. Rev. Biochem.*, 1987, pp. 615-649, vol. 56.

Ginalski, K. et al., "Modeling of Active Forms of Protein Kinases: p. 38—A Case Study," *Acta Biochimica Polonica*, 1997, pp. 557-564, vol. 44, No. 3.

Glenn, G. et al., "Skin Immunization Made Possible by Cholera Toxin," *Nature*, 1998, p. 851, vol. 39.

Gorman et al., "The Rous Sarcoma Virus Long Terminal Repeat is a Strong Promoter When Introduced into a Variety of Eukaryotic Cells by DNA-Mediated Transfection," *Proc. Natl. Acad. Sci. U.S.A.*, 1981, pp. 6777-6781, vol. 79, No. 22.

Goya, M. et al., "Growth Inhibition of Human Prostate Cancer Cells in Human Adult Bone Implanted into Nonobese Diabetic/Severe Combined Immunodeficient Mice by a Ligand-Specific Antibody to Human Insulin-Like Growth Factors," *Cancer Research*, Sep. 1, 2004, pp. 6252-6258, vol. 64.

Green, L. et al., "Regulation of B Cell Development by Variable Gene Complexity in Mice Reconstituted with Human Immunoglobulin Yeast Artificial Chromosomes," *J. Exp. Med.*, 1998, pp. 483-495, vol. 188.

Grosschedl, R. et al., "Cell-Type Specificity of Immunoglobulin Gene Expression is Regulated by at Least Three DNA Sequence Elements," *Cell*, 1985, pp. 885-897, vol. 41.

Hanes, J. et al., "New Advances I Microsphere-based Single-Dose Vaccines," *Advanced Drug Delivery Reviews*, 1997, pp. 97-119, vol. 28.

Hanes, J. et al., "In vitro Selection and Evolution of Functional Proteins by Using Ribosome Display," *Proc. Natl. Acad. Sci. U.S.A.*, 1997, pp. 4937-4942, vol. 94.

Harding, C. et al., "Turnover of a Ia-Peptide Complexes is Facilitated in Viable Antigen-Presenting Cells: Biosynthetic Turnover of Ia vs. Peptide Exchange," *Proc. Natl. Acad. Sci. U.S.A.*, 1989, pp. 4230-4234, vol. 86.

He, L-Z. et al., "A Novel Human Cancer Vaccine Elicits Cellular Responses to the Tumor-Associated Antigen, Human Chorionic Gonadotropin β," *Clinical Cancer Research*, Mar. 15, 2004, pp. 1920-1927, vol. 10.

Hearn, M.T.W. et al., "Molecular Architecture and Biorecognition Processes of the Cystine Knot Protein Superfamily: Part I. The Glycoprotein Hormones," *J. Mol. Recognit.*, 2000, pp. 223-278, vol. 13.

Hedstrom, J. et al., "Concentration of Free hCGβ Subunit in Serum as a Prognostic Marker for Squamous-Cell Carcinoma of the Oral Cavity and Ooropharynx," *Int. J. Cancer (Pred. Oncol.)*, 1999, pp. 525-528, vol. 84.

Ho, H-H. et al., "Characterization of Human Chorionic Gonadotropin Peptide Variants with a Radio-Receptor Assay Using Recombinant Human Luteinizing Hormone/Chorionic Gonadotropin Receptors," *Early Pregnancy: Biology and Medicine*, 1997, pp. 204-212, vol. 3.

Hodgson, J. et al., "Making Monoclonals in Microbes," *Bio/Technology*, May 1991, pp. 421-425, vol. 8, No. 5.

Hoffman, K. et al., "A Model of Cdc25 Phosphatase Catalytic Domain and Cdk-Interaction Surgace Based on the Presence of a Rhodanese Homology Domain," *J. Mol. Biol.*, 1998, pp. 195-208, vol. 282.

Hoogenboom, H. et al., "Building Antibodies from their Genes," *Immunol. Reviews*, 1992, pp. 41-68, vol. 130.

Holliger, P. et al., ""Diabodies": Small Bivalent and Bispecific Antibody Fragments," *Proc. Natl. Acad. Sci. USA*, Jul. 1993, pp. 6444-6448, vol. 90.

(56) References Cited

OTHER PUBLICATIONS

Hotakainen, K. et al., "The Free β-Subunit of Human Chorionic Gonadotropin as a Prognostic Factor in Renal Cell Carcinoma," *British Journal of Cancer*, 2002, pp. 185-189, vol. 86.

Hotakainen, K. et al., "Expression of the Free β-Subunit of Human Chorionic Gonadotropin in Renal Cell Carcinoma: Prognostic Study on Tissue and Serum," *Int. J. Cancer*, 2003, pp. 631-635, vol. 104.

Houghten, R.A. et al., "The Use of Synthetic Peptide Combinatorial Libraries for the Identification of Bioactive Peptides," *BioTechniques*, 1992, pp. 412-421, vol. 13.

Houghten, R.A., "General Method for the Rapid Solid-Phase Synthesis of Large Numbers of Peptides: Specificity of Antigen-Antibody Interaction at the Level of Individual Amino Acids," *Proc. Natl. Acad. Sci. USA*, Aug. 1985, pp. 5131-5135, vol. 82.

Hsu, L.C. et al., "Cloning of cDNAs for Human Aldehyde Dehydrogenases 1 and 2," *Proc. Natl. Acad. Sci. USA*, Jun. 1985, pp. 3771-3775, vol. 82.

Hurwitz, A.A. et al., "CTLA-4 Blockade Synergizes with Tumor-Derived Granulocyte-Macrophage Colony-Stimulating Factor for Treatment of an Experimental Mammary Carcinoma," *Proc. Natl. Acad. Sci. USA*, Aug. 1998, pp. 10067-10071, vol. 95.

Hurwitz, A.A. et al., "Combination Immunotherapy of Primary Prostate Cancer in a Transgenic Mouse Model Using CTLA-4 Blockade," *Cancer Research*, May 1, 2000, pp. 2444-2448.

Huston, J.S. et al., "Protein Engineering of Antibody Binding Sites: Recovery of Specific Activity in an Anti-Digoxin Single-Chain Fv Analogue Produced in *Escherichia coli*," *Proc. Natl. Acad. Sci. USA*, Aug. 1988, pp. 5879-5883, vol. 85.

Hynes, R., "Integrins: Versatility, Modulation, and Signaling in Cell Adhesion," *Cell*, 1992, pp. 11-25, vol. 69.

Iles, R.K. et al., "Beta Human Chorionic Gonadotropin in Serum and Urine. A Marker for Metastatic Urothelial Cancer," *British Journal of Urology*, 1989, pp. 241-244, vol. 64.

Ill, C.R. et al., "Design and Construction of a Hybrid Immunoglobulin Domain with Properties of Both Heavy and Light Chain Variable Regions," *Protein Engineering*, 1997, pp. 949-957, vol. 10, No. 8.

Islami, D. et al., "Effects of Human Chorionic Gonadotropin on Trophoblast Invasion," *Seminars in Reproductive Medicine*, 2001, pp. 49-53, vol. 19, No. 1.

Iversen, P.L. et al., "Monoclonal Antibodies to Two Epitopes of β-Human Chorionic Gonadotropin for the Treatment of Cancer," *Current Opinion in Molecular Therapeutics*, Apr. 2003, pp. 156-160, vol. 5, No. 2.

Jagtap, D.D. et al., "A Detailed Study of the L2β Long-Loop Region of Human Chorionic Gonadotropin Suggests it to be Spatially Close to, but not Part of, the Receptor-Binding Site," *Journal of Endocrinology*, 2002, pp. 311-320, vol. 172.

Jouko, V. et al., "Identification of Csk Tyrosine Phosphorylation Sites and a Tyrosine Residue Important for Kinase Domain Structure," *Biochem J.*, 1997, pp. 927-935, vol. 322.

Kalantarov, G. et al., "Demonstration of Dose Dependent Cytotoxic Activity in Cancer Cells by Specific Human Chorionic Gonadotropin Monoclonal Antibodies," *Cancer*, 1998, pp. 783-787, vol. 83, No. 4.

Kam, W. et al., "Cloning, Sequencing, and Chromosomal Localization of Human Term Placental Alkaline Phosphatase cDNA," *Proc. Natl. Acad. Sci. USA*, 1985, pp. 8715-8719, vol. 82.

Keutmann, H.T. et al., "A Receptor-Binding Region in Human Choriogonadotropin/Lutropin β Subunit," *Proc. Natl. Acad. Sci., USA*, Apr. 1987, pp. 2038-2042, vol. 84.

Khayat, D., "Overview of Medical Treatments of Metastatic Malignant Melanoma," *ASCO Educational Book*, Spring 2000, pp. 414-428.

Khorana, H.G., "Synthesis of a Gene," *Science*, 1979, pp. 614-625, vol. 203.

Kostelny, S. et al., "Formation of a Bispecific Antibody by the Use of Leucine Zippers," *The Journal of Immunology*, 1992, pp. 1547-1553, vol. 148.

Kuroda, H. et al., "Human Chorionic Gonadotropin (hCG) Inhibits Cisplatin-Induced Apoptosis in Ovarian Cancer Cells: Possible Role of Up-Regulation of Insulin-Like Growth Factor-1 by hCG," *Int. J. Cancer*, 1998, pp. 571-578, vol. 76.

Kuroda, H. et al., "Human Ovarian Surface Epithelial (OSE) Cells Express LH/HCG Receptors, and HCG Inhibits Apoptosis of OSE Cells Via Up-Regulation of Insulin-Like Growth Factor-1," *Int. J. Cancer*, 2001, pp. 309-315, vol. 92.

Kuwabara, I. et al., "Efficient Epitope Mapping by Bacteriophage λ Surface Display," *Nature Biotechnology*, 1997, pp. 74-78, vol. 15.

Langer, R., "New Methods of Drug Delivery," *Science*, 1990, pp. 1527-1533, vol. 249.

Lapthorn, A.J. et al., "Crystal Structure of Human Chorionic Gonadotropin," *Nature*, Jun. 9, 1994, pp. 455-461, vol. 369.

Lathe, R. et al., "Synthetic Oligonucleotide Probes Deduced from Amino Acid Sequence Data," *Journal of Molecular Biology*, 1985, pp. 1-12, vol. 183.

Lee, A.C.J. et al., "A Method for Preparing β-hCG COOH Peptide-Carrier Conjugates of Predictable Composition," *Molecular Immunology*, 1980, pp. 749-756, vol. 17.

Licht, P. et al., "On the Role of Human Chorionic Gonadotropin (hCG) in the Embryo-Endometrial Microenvironment: Implication for Differentiation and Implantation," *Seminars in Reproductive Medicine*, 2001, pp. 37-47, vol. 19, No. 1.

Liu, A. et al., "Chimeric Mouse-Human IgG1 Antibody that Can Mediate Lysis of Cancer Cells," *Proc. Natl. Acad. Sci., USA*, 1987, pp. 3439-3443, vol. 84.

Liu, A. et al., "Production of a Mouse-Human Chimeric Monoclonal Antibody to CD20 with Potent Fc-Dependent Biologic Activity," *Journal of Immunology*, 1987, pp. 3521-3526, vol. 139.

Logothetis, C., "Developmental Therapy for Regionally Advanced Prostate Carcinoma," *ASCO Educational Book*, Spring 2000, pp. 300-302.

Lu, D. et al., "Simultaneous Blackade of Both the Epidermal Growth Factor Receptor and the Insulin-like Growth Factor Receptor Signaling Pathways in Cancer Cells with a Fully Human Recombinant Bispecific Antibody," *The Journal of Biological Chemistry*, 2004, pp. 2856-2865, vol. 279.

Luohimo, J. et al., "Serum HCGβ CA 72-4 and CEA are Independent Prognostic Factors in Colorectal Cancer," *Int. J. Cancer*, 2002, pp. 545-548, vol. 101.

Luohimo, J. et al.," Serum HCGβ and CA 72-4 Are Stronger Prognostic Factors Than CEA, CA 19-9 and CA 242 in Pancreatic Cancer," *Oncology*, 2004, pp. 126-131, vol. 66.

Luohimo, J. et al., "Preoperative hCGβ and CA 72-4 are Prognostic Factors in Gastric Cancer," *Int. J. Cancer*, 2004, pp. 929-933, vol. 111.

Lundin, M. et al., "Tissue Expression of Human Chorionic Gonadotropin β Predicts Outcome in Colorectal Cancer: A Comparison with Serum Expression," *Int. J. Cancer (Pred. Oncol.)*, 2001, pp. 18-22, vol. 95.

Mandal, C. et al., "ABGEN: A Knowledge-Based Automated Approach for Antibody Structure Modeling," *Nature Biotechnology*, 1996, pp. 323-328, vol. 14.

Mao, S. et al., "Phage-display Library Selection of High-affinity Human Single-chain Antibodies to Tumor-associated Carbohydrate Antigens Sialyl Lewis$^x$ and Lewis$^x$," *Proc. Natl. Acad. Sci. U.S.A.*, 1999, pp. 6953-6958, vol. 96.

Marasco, W. "Intrabodies: Turning the Humoral Immune System outside in for Intracellular Immunization," *Gene Therapy*, 1997, pp. 11-15, vol. 4.

Marks, J., et al., "Human Antibody Fragments Specific for Human Blood Group Antigens from a Phage Display Library," *Bio/Technology*, Oct. 11, 1993, pp. 1145-1149, vol. 11.

Martin, F. et al., "The Affinity-Selection of a Minibody Polypeptide Inhibitor of Human Interleukin-6," *The EMBO Journal*, 1994, pp. 5303-5309, vol. 13, No. 22.

Meister, L.H.F. et al., "Hyperthyroidism Due to Secretion of Human Chorionic Gonadotropin in a Patient with Metastatic Chriocarcinoma," *Arq. Bras. Endocrinol. Metab.*, Apr. 2005, pp. 319-322, vol. 49, No. 2.

Mendez, M. et al., "Functional Transplant of Megabase Human Immunoglobulin Loci Recapitulates Human Antibody Response in Mice," *Nature Genetics*, 1997, pp. 146-156, vol. 15.

(56) References Cited

OTHER PUBLICATIONS

Miyamoto, S. et al., "Blockade of Paracrine Supply of Insulin-Like Growth Factors Using Neutralizing Antibodies Suppresses the Liver Metastasis of Human Colorectal Cancers," *Clin. Cancer Res.*, May 1, 2005, pp. 3494-3502, vol. 11, No. 9.
Mock, P. et al., "Choriocarcinoma-Like Human Chorionic Gonadotrophin (HCG) and HCG Bioactivity During the First Trimester of Pregnancy," *Human Reproduction*, 2000, pp. 2209-2214, vol. 15, No. 10.
Monfardini, C. et al., "Rational Design, Analysis, and Potential Utility of GM-CSF Antagonists," *Proceeding of the Association of American Physicians*, 1996, pp. 420-431, vol. 108.
Morgan, F.J. et al., "The Amino Acid Sequence of Human Chorionic Gonadotropin," *The Journal of Biological Chemistry*, Jul. 10, 1975, pp. 5247-5258, vol. 250, No. 13.
Moulton, H.M. et al., "Active Specific Immunotherapy with a Beta-Human Chorionic Gonadotropin Peptide Vaccine in Patients with Metastatic Colorectal Cancer: Antibody Response in Associated with Improved Survival," *Clinical Cancer Research*, Jul. 2002, pp. 2044-2051, vol. 8.
Murray, M.J. et al., "Embryo Implantation and Tumor Metastasis: Common Pathways of Invasion and Angiogenesis," *Seminars in Reproductive Endocrinology*, 1999, pp. 275-290, vol. 17, No. 3.
Naz, R.K. et al., "Recent Advances in Contraceptive Vaccine Development: A Mini-Review," *Human Reproduction*, 2005, pp. 3271-3283, vol. 20, No. 12.
Norman, R.J. et al., "hCGβ Core Fragment is a Metabolite of hCG: Evidence from Infusion of Recombinant hCG," *Journal of Endocrinology*, 2000, pp. 299-305, vol. 164.
Nyyssonen, E. et al., "Efficient Production of Antibody Fragments by the Filamentous Fungus *Trichoderma reesei*," *Bio/Technology*, 1993, pp. 591-595, vol. 11.
Okayama, H. et al., "A cDNA Cloning Vector That Permits Expression of cDNA Inserts in Mammalian Cells," *Molecular and Cellular Biology*, Feb. 1983, pp. 280-289, vol. 3, No. 2.
Osborn, L., "Leukocyte Adhesion to Endothelium in Inflammation," *Cell*, 1990, pp. 3-6 vol. 62.
Parmley, S. et al., "Antibody-selectable Filamentous fd Phage Vectors: Affinity Purification of Target Genes," *Gene*, 1988, pp. 305-317, vol. 73.
Paul, A. et al., "Transdermal Immunization with Large Proteins by Means of Ultradeformable Drug Carriers," *Eur. J. Immunology*, 1995, pp. 3521-3524, vol. 25.
PCT International Search Report and Written Opinion, PCT/US2006/030988, May 24, 2007, 10 pages.
Pennica, D. et al., " Cloning and Expression of Human Tissue-type Plasminogen Activator cDNA in *E. coli*," *Nature*, 1983, pp. 214-221, vol. 301.
Peters, W.P. et al., "Neutrophil Migration is Defective During Recombinant Human Granulocyte-Macrophage Colony—Stimulating Factor Infusion After Autologous Bone Marrow Transplantation in Humans," *Blood*, Oct. 1988, pp. 1310-1310, vol. 72, No. 4.
Pietras, K. et al., "Inhibition of PDGF Receptor Signaling in Tumor Stroma Enhances Antitumor Effect of Chemotherapy," *Cancer Research*, Oct. 1, 2002, pp. 5476-5484, vol. 62.
Pinilla, C. et al., "Rapid Identification of High Affinity Peptide Ligands Using Positional Scanning Synthetic Peptide Combinatorial Libraries," *Bio Techniques*, Dec. 1992, pp. 901-905, vol. 13, No. 6.
Queen, C. et al., "A Humanized Antibody That Binds to the Interleukin 2 Receptor," *Proc. Natl. Acad. Sci., USA*, Dec. 1989, pp. 10029-10033, vol. 86.
Rao, C.V., "An Overview of the Past, Present, and Future of Nongonadal LH/hCG Actions in Reproductive Biology and Medicine," *Seminars in Reproductive Medicine*, 2001, pp. 7-17, vol. 19, No. 1.
Restifo, N. et al.,"Cancer Vaccines," *Cancer: Principles and Practice of Oncology, 5th Edition*: Chapter 61, 1997, pp. 3023-3043, vol. 2.
Rizo, J. et al., "Constrained Peptides: Models of Bioactive Peptides and Protein Substructures," *Ann. Rev. Biochem.*, 1992, pp. 387-418, vol. 61.
Rock, E.P. et al., "Immunogenicity of a Fusion Protein Linking the Beta Subunit Carboxyl Terminal Peptide (CTP) of Human Chorionic Gonadotropin to the B Subunit of *Escherichia Coli* Heat-Labile Enterotoxin (LTB)," *Vaccine*, 1996, pp. 1560-1568, vol. 14, No. 16.
Rout, P.K. et al., "Oral Immunization with Recombinant Vaccinia Expressing Cell-Surface-Anchored βhCG Induces Anti-hCG Antibodies and T-Cell Proliferative Response in Rats," *Vaccine*, 1997, pp. 1503-1505, vol. 15, No. 14.
Russell, S. et al., "Retroviral Vectors Displaying Functional Antibody Fragments," *Nucleic Acids Research*, 1993, pp. 1081-1085, vol. 21, No. 5.
Salesse, R. et al., "Peptide Mapping of Intersubunit and Receptor Interactions of Human Choriogonadotropin," *Molecular and Cellular Endocrinology*, 1990, pp. 113-119, vol. 68.
Scott, J., "Discovering Peptide Ligands Using Epitope Libraries," *TIBS*, 1992, pp. 241-245, vol. 17.
Scott, J. et al., "Searching for Peptide Ligands with an Epitope Library," *Science*, 1990, pp. 386-390, vol. 249.
Singh, J. et al., "Structure-Based Design of a Potent, Selective, and Irreversible Inhibitor of the Catalytic Domain of the erbB Receptor Subfamily of Protein Tyrosine Kinases," *Journal of Medical Chemistry*, 1997, pp. 1130-1135, vol. 40.
Siraganian, R. et al.," Histamine Secretion from Mast Cells and Basophils," *TIPS*, 1983, vol. 4, pp. 432-437.
Songsivilai, S. et al., "Bispecific Antibody: A Tool for Diagnosis and Treatment of Disease," *Clin. Exp. Immunol.*, 1990, pp. 315-321, vol. 79.
Span, P.N. et al., "Molecular Beacon Reverse Transcription-PCR of Human Chorionic Gonadotropin-β-3,-5, and-8 mRNAs Has Prognostic Value in Breast Cancer," *Clinical Chemistry*, 2003, pp. 1074-1080, vol. 49, No. 7.
Springer, T.A., "Adhesion Receptors of the Immune System," *Nature*, Aug. 2, 1990, pp. 425-433, vol. 346.
Stenman, U-H. et al., "Human Chorionic Gonadotropin in Cancer," *Clinical Biochemistry*, 2004, pp. 549-561, vol. 37.
Stevens, V.C. et al., "Antifertility Effects of Immunization of Female Baboons with C-Terminal Peptides of the β-Subunit of Human Chorionic Gonadotropin," *Fertility and Sterility*, Jul. 1981, pp. 98-105, vol. 36, No. 1.
Suzuki, S. et al., "Complete Amino Acid Sequence of Human Vitronectin Deduced from cDNA. Similarity of Cell Attachment Sites in Vitronectin and Fibronectin," *The EMBO Journal*, 1985, pp. 2519-2524, vol. 4, No. 10.
Talwar, G.P. et al., "Isoimmunization Against Human Chorionic Gonadotropin with Conjugates of Processed β-Subunit of the Hormone and Tetanus Toxoid," *Proc. Nat. Acad. Sci. USA*, Jan. 1976, pp. 218-222, vol. 73, No. 1.
Talwar, G.P. et al., "A Vaccine That Prevents Pregnancy in Women," *Proc. Nat. Acad. Sci. USA*, Aug. 1994, pp. 8532-8536, vol. 91.
Traunecker, A. et al., "Bispecific Single Chain Molecules (Janusins) Target Cytotoxic Lymphocytes on HIV Infected Cells," *The EMBO Journal*, 1991, pp. 3655-3659, vol. 10, No. 12.
Traunecker, A. et al., "Janusin: New Molecular Design for Bispecific Reagents," *Int J. Cancer*, 1992, pp. 51-52, Supplement 7.
Triozzi, P.L. et al., "Human Chorionic Gonadotropin as a Target for Cancer Vaccines (Review)," *Oncology Reports*, 1999, pp. 7-17, vol. 6.
Tuaillon, N. et al., "Human Immunoglobulin Heavy-Chain Minilocus Recombination in Transgenic Mice: Gene-segment Use in μ and ϒ Transcripts," Proc. Natl. Acad. Sci. USA, Apr. 1993, pp. 3720-3724, vol. 909.
Tuaillon, N. et al., "Analysis of Direct and Inverted $DJ_H$ Rearrangements in a Human Ig Heavy Chain Transgenic Minilocus," *The Journal of Immunology*, 1995, pp. 6453-6465, vol. 154.
Ulloa-Aguirre, A. et al., "Endocrine Regulation of Gonadotropin Glycosylation," *Archives of Medical Research*, 2001, pp. 520-532, vol. 32.
U.S. Appl. No. 07/466,008, filed Jan. 12, 1990.
U.S. Appl. No. 07/610,515, filed Nov. 8, 1990.
U.S. Appl. No. 07/919,297, filed Jul. 24, 1992.
U.S. Appl. No. 08/112,848, filed Aug. 27, 1993.
U.S. Appl. No. 08/234,145, filed Apr. 28, 1994.
U.S. Appl. No. 08/430,938, Apr. 27, 1995.

(56) References Cited

OTHER PUBLICATIONS

U.S. Appl. No. 08/463,191, filed Jun. 5, 1995.
U.S. Appl. No. 08/759,620, filed Dec. 3, 1996.
U.S. Appl. No. 07/574,748, filed Aug. 29, 1990.
U.S. Appl. No. 07/575,962, filed Aug. 31, 1990.
U.S. Appl. No. 07/904,068, filed Jun. 23, 1992.
U.S. Appl. No. 08/209,741, filed Mar. 9, 1994.
Van Elsas, A. et al., "Combination Immunotherapy of B16 Melanoma Using Anti-Cytotoxic T Lymphocyte-associated Antigen 4 (CTLA-4) and Granulocyte/Macrophage Colony-Stimulating Factor (GM-CSF)-producing Vaccines Induces Rejection and Subcutaneous and Metastatic Tumors Accompanied by Autoimmune Depigmentation," *J. Exp. Med.*, Aug. 2, 1999, pp. 355-366, vol. 190, No. 3.
Van Rinsum, J. et al., "Specific Inhibition of Human Natural Killer Cell-Mediated Cytotoxicity by Sialic Acid and Sialo-Oligosaccharides," *Int. J. Cancer*, 1986, pp. 915-922, vol. 38.
Vartiainen, J. et al., "Preoperative Serum Concentration of HCGβ as a Prognostic Factor in Ovarian Cancer," *Int. J. Cancer (Pred. Oncol.)*, 2001, pp. 313-316, vol. 95.
Veber, D. et al., "The Design of Metabolically-stable Peptide Analogs," *TINS*, 1985, p. 392.
Vitetta, E. et al.,"Immunotoxins: Magic Bullets or Misguided Missiles?," *Immunology Today*, 1993, pp. 252-259, vol. 14, No. 6.
Walter, P. et al., "Cloning of the Human Estrogen Receptor cDNA," *Proc. Natl. Acad. Sci. USA*, 1985, pp. 7889-7893, vol. 82.
Ward, E.S. et al., "Binding Activities of a Repertoire of Single Immunoglobulin Variable Domains Secreted from *Escherichia coli*," *Nature*, 1989, pp. 544-546, vol. 341.
Windhagen, A. et al., "Modulation of Cytokine Patterns of Human Autoreactive T Cell Clones by a Single Amino Acid Substitution of Their Peptide Ligand," *Immunity*, 1995, pp. 373-380, vol. 2.
Winter, G. et al., "Humanized Antibodies," *Immunology Today*, 1993, pp. 43-46, vol. 14, No. 6.
Wright, A. et al., "Genetically Engineered Antibodies: Progress and Prospects," *Critical Reviews in Immunology*, 1992, pp. 125-167, vol. 12.
Wu, H. et al., "Structure of Human Chorionic Gonadotropin at 2.4Å Resolution from MAD Analysis of the Selenomethionyl Protein," *Structure*, 1994, pp. 545-558, vol. 2, No. 6.
Wu, W. et al., "Human Chorionic Gonadotropin β (HCGβ) Down-Regulates E-Cadherin and Promotes Human Prostate Carcinoma Cell Migration and Invasion," *Cancer*, Jan. 1, 2006, pp. 68-78, vol. 106, No. 1.
Wu, R. et al., "Synthetic Oligodeoxynucleotides for Analyses of DNA Structure and Function," *Progress in Nucleic Acid Research and Molecular Biololgy*, 1978, pp. 101-141, vol. 21.
Xu, W.X. et al., "Expression and Purification of Three Fusion Proteins Containing a Single B-Cell Epitope (beta5, beta9 or beta8) of Human Chorionic Gonadotropin Beta Subunit," (Abstract), from Sheng Wu Gong Cheng Xue Bao, Jan. 2004, pp. 49-53, vol. 20, No. 1, [Online] [Retrieved on Sep. 28, 2006] Retrieved from the Internet<URL:http://www.ncbi.nlm.nih.gov/entrez/query.fcgi?CMD=Display&DB=pubm ed>.
Yankai, Z. et al., "Ten Tandem Repeats of β-hCG 109-118 Enhance Immunogenicity and Anti-Tumor Effects of β-hCG C-Terminal Peptide Carried by Mycobacterial Heat-Shock Protein HSP65," *Biochemical and Biophysical Research Communications*, 2006, pp. 1365-1371, vol. 345.
Yu, N. et al., "Inhibition of Tumor Growth in Vitro and in Vivo by a Monoclonal Antibody Against Human Chorionic Gonadotropin β," *Immunology Letters*, Oct. 11, 2007, pp. 94-102, vol. 114, No. 2.
Zhang, M-Y. et al., "Identification and Characterization of a New Cross-Reactive Human Immunodeficiency Virus Type 1-Neutralizing Human Monoclonal Antibody," *Journal of Virology*, 2004, pp. 9233-9242, vol. 78.
Japanese Patent Office, Office Action, Japanese Patent Office Application No. 2008-526153, Sep. 27, 2011, nine pages.
Australian Patent Office, Examiner's First Report, Australian Patent No. 2006-278260, Feb. 24, 2011, two pages.
Canadian Intellectual Property Office, Examination Report, Canadian Patent Application No. 2,615,460, Jul. 4, 2011, six pages.
European Patent Office, Examination Report, European Patent Office Application No. 06813343.8, Jul. 5, 2011, seven pages.
Rudikoff, S. et al., "Single Amino Acid Substitution Altering Antigen-Binding Specificity," *Proceedings of the National Academy of Sciences*, Mar. 1, 1982, pp. 1979-1983, vol. 79, Washington, D.C. USA.
Japanese Patent Office, Final Office Action, Japanese Patent Application No. 2008-526153, Apr. 3, 2003, six pages.
Cosowsky, L. et al., "The Groove between the α- and β-Subunits of Hormones with Lutropin (LH) Activity Appears to Contact the LH Receptor, and Its Conformation is Changed during Hormone Binding," *The Journal of Biological Chemistry*, Aug. 25, 1995, pp. 20011-20019, vol. 270, No. 34.
European Patent Office, Examination Report, European Patent Application No. 06813343.8, May 2, 2013, ten pages.
Ferrat, G. et al., "A peptide mimic of an antigenic loop of [alpha]-human chorionic gonadotropin hormone: solution structure and interaction with a llama $V_{HH}$ domain," *Biochemical Journal*, Sep. 1, 2002, pp. 415-422, vol. 366, No. 2.
Holliger, P. et al., "Engineered antibody fragments and the rise of single domains," *Nature Biotechnology*, Sep. 2005, pp. 1126-1136, vol. 23, No. 9.
Moyle, W. R. et al., "Localization of Residues That Confer Antibody Binding Specificity Using Human Chorionic Gonadotropin/Luteinizing Hormone β Subunit Chimeras and Mutants," *The Journal of Biological Chemistry*, May 25, 1990, pp. 8511-8518, vol. 265, No. 15.
Moyle, W. R. et al., "Use of monoclonal antibodies to subunits of human chorionic gonadotropin to examine the orientation of the hormone in its complex with receptor," *Proceedings of the National Academy of Science USA*, Apr. 1982, pp. 2245-2249, vol. 79.

* cited by examiner

```
HCG L2 BETA LOOP:  C P T M T R V L Q G V L P A L P Q V V C    SEQ ID NO: 7
 LH L2 BETA LOOP:  C P T M M R V L Q A V L P P L P Q V V C    SEQ ID NO: 8
FSH L2 BETA LOOP:  C Y T R D L V Y K D P A R P K I Q K T C    SEQ ID NO: 9
                  38  40      45      50    55  57
```

2B2.6F5 Heavy Chain DNA Sequence (SEQ ID NO: 1)
TGTCCATGTCCTCTCCACAGACACTGAACACACTGACTCTAACCATGAGAGATGAGCTGGATCTTTCTCTTCCTCCTGTCAGGAACTGCA
GGTGTCCACTCTGAGGTCCACCTGACCTGTCTGGACCTGTGCTGGTGAAGCCTGGGGCTTCAGTGAAGATGTCCTGTAAGGCTTCTG
GATACACATTCACTGACTACTATATGAGCTGGGTGAAGCAGAGCCATGAAAGAGCCTTGAGTGGATTGGAATTATTGATCCTTATA
CGGTGATACTAGTACAACCAGAAGTTCATGGGCAAGGCCACATTGACTGTTGACATGTCCTCCAGCACAGCCTACATGGAGCTCAAC
AGCCTGACATCTGACGACTCTGCAGTCTATTACTGTGCAAGAGACATTGACTACTGGGGCCGCGGCACCACTCTCACCGTCTCCCCAG
CTAGCACAACACCCCCA

2B2.6F5 Heavy Chain Protein Sequence (SEQ ID NO: 2)
Met S S P Q T L N T L T L T M R W S W I F L L L S G T A G V H S E V H L Q Q S G P V L V K P G A S V K M S C K A S G Y T F T D Y Y
M T W V K Q S H E K S L E W I G I I D P Y N G D T S Y N Q K F M G K A T L T V D M S S S T A Y M E L N S L T S D D S A V Y Y C A R
D I D Y W G R G T T L T V S P A S T T P P

2B3.3E8 Heavy Chain DNA Sequence (SEQ ID NO: 3)
AGTTGTAGTTACCATAGTAGCATCTTGCACAGAAATATGTAGCCGTGTCCTCATTTTTGAGGTTGTTGATCTGCAAATAGGCAGTGCTG
GCAGAGGTTTCCAAAGAAGGCAAACCGTCCCTTGAAGTCATCAGCATATGTTGGCACTCCAGAGTAGGTGTTTATCCAGCCCATCC
ACTTTAAACCCTTTCCTGGAGCCTGTTTCACCCAGCTCATTCCATAGGTTGTGAAGGTATACCAGAAGCCTTGCAGGAGATCTTGACT
GTCTCTCCAGGCTTCTTCAGTCAGCTCAGTGTACCAACTGATCTGTCGTTGGGCACTTGGCAGCTGCATCAGGAATAGCAA
GTCCACAGCCAACCATGATGTCTAAGACTTGGGCTCAGTGGTGCCTTAAGACTAACTGGTCACTCCCTTTTCATCAAAGCCAGCAA
ACGCAGTGTTCGG

2B3.3E8 Heavy Chain Protein Sequence (SEQ ID NO: 4)
Met G W L W N L L F L M A A A Q S A Q A Q I Q L V Q S G P E L K K P G E T V K I S C K A S G Y T F T T Y G M S W V K Q A P G K G L
K W M G W I N T Y S G V P T Y A D D F K G R F A F S L E T S A S T A Y L Q I N N L K N E D T A T Y F C A R C Y Y G N Y N

2B3.3F5 Heavy Chain DNA Sequence (SEQ ID NO: 5)
TTGTAGTTACCATAGTAGCATCTTGCACAGAAATATGTAGCCGTGTCCTCATTTTTGAGGTTGTTGATCTGCAAATAGGCAGTGCTGGC
AGAGGTTTCCAAAGAAGGCAAACCGTCCCTTGAAGTCATCAGCATATGTTGGCACTCCAGAGTAGGTGTTTATCCAGCCCATCAC
TTTAAACCCTTTCCTGGAGCCTGTTTCACCCAGCTCATTCCATAGGTTGTGAAGGTATACCAGAAGCCTTGCAGGAGATCTTGACTGT
CTCTCCAGGCTTCTTCAGTCAGCTCAGTGTACCAACTGATCTGTCGTTGGGCACTTGGCAGCTGCATCAGGAATAGCAAGT
TCCACAGCCAACCATGATGTCTAAAACTTGGGCTCAGTGGTGCCTTAAAAC

2B3.3F5 Heavy Chain Protein Sequence (SEQ ID NO: 6)
Met G W L W N L L F L M A A A Q S A Q A Q I Q L V Q S G P E L K K P G E T V K I S C K A S G Y T F T T Y G M S W V K Q A P G K G L
K W M G W I N T Y S G V P T Y A D D F K G R F A F S L E T S A S T A Y L Q I N N L K N E D T A T Y F C A R C Y Y G N Y

SEQUENCE LISTING

<160> NUMBER OF SEQ ID NOS: 10

<210> SEQ ID NO 1
<211> LENGTH: 458
<212> TYPE: DNA
<213> ORGANISM: Homo sapiens

<400> SEQUENCE: 1

```
tgtccatgtc ctctccacag acactgaaca cactgactct aaccatgaga tggagctgga      60
tctttctctt cctcctgtca ggaactgcag gtgtccactc tgaggtccac ctgcaacagt     120
ctggacctgt gctggtgaag cctggggctt cagtgaagat gtcctgtaag gcttctggat     180
acacattcac tgactactat atgacctggg tgaagcagag ccatgaaaag agccttgagt     240
ggattggaat tattgatcct ataacggtg atactagcta caaccagaag ttcatgggca     300
aggccacatt gactgttgac atgtcctcca gcacagccta catggagctc aacagcctga     360
catctgacga ctctgcagtc tattactgtg caagagacat tgactactgg ggccgcggca     420
ccactctcac cgtctcccca gctagcacaa cacccccca                            458
```

<210> SEQ ID NO 2
<211> LENGTH: 151
<212> TYPE: PRT
<213> ORGANISM: Homo sapiens

<400> SEQUENCE: 2

```
Met Ser Ser Pro Gln Thr Leu Asn Thr Leu Thr Met Arg Trp
1               5                   10                  15

Ser Trp Ile Phe Leu Phe Leu Leu Ser Gly Thr Ala Gly Val His Ser
                20                  25                  30

Glu Val His Leu Gln Gln Ser Gly Pro Val Leu Val Lys Pro Gly Ala
            35                  40                  45

Ser Val Lys Met Ser Cys Lys Ala Ser Gly Tyr Thr Phe Thr Asp Tyr
    50                  55                  60

Tyr Met Thr Trp Val Lys Gln Ser His Glu Lys Ser Leu Glu Trp Ile
65                  70                  75                  80

Gly Ile Ile Asp Pro Tyr Asn Gly Asp Thr Ser Tyr Asn Gln Lys Phe
                85                  90                  95

Met Gly Lys Ala Thr Leu Thr Val Asp Met Ser Ser Ser Thr Ala Tyr
            100                 105                 110

Met Glu Leu Asn Ser Leu Thr Ser Asp Asp Ser Ala Val Tyr Tyr Cys
        115                 120                 125

Ala Arg Asp Ile Asp Tyr Trp Gly Arg Gly Thr Thr Leu Thr Val Ser
    130                 135                 140

Pro Ala Ser Thr Thr Pro Pro
145                 150
```

<210> SEQ ID NO 3
<211> LENGTH: 457
<212> TYPE: DNA
<213> ORGANISM: Homo sapiens

<400> SEQUENCE: 3

```
agttgtagtt accatagtag catcttgcac agaaatatgt agccgtgtcc tcattttga      60
ggttgttgat ctgcaaatag gcagtgctgg cagaggtttc caaagagaag gcaaaccgtc    120
ccttgaagtc atcagcatat gttggcactc cagagtaggt gtttatccag cccatccact    180
```

```
ttaaacccctt tcctggagcc tgtttcaccc agctcattcc ataggttgtg aaggtatacc    240
cagaagcctt gcaggagatc ttgactgtct ctccaggctt cttcagctca ggtccagact    300
gtaccaactg gatctgtgct tgggcacttt gggcagctgc catcaggaat agcaagttcc    360
acagccaacc catgatgtct aagacttggg ctcagtggtg ccttaagact aactggtcac    420 tcccttttc atcaaagcca gcaaacgcag tgttcgg                              457
```

<210> SEQ ID NO 4
<211> LENGTH: 124
<212> TYPE: PRT
<213> ORGANISM: Homo sapiens

<400> SEQUENCE: 4

```
Met Gly Trp Leu Trp Asn Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Thr Tyr Gly Met Ser Trp Val Lys Gln Ala Pro Gly Lys Gly Leu
    50                  55                  60

Lys Trp Met Gly Trp Ile Asn Thr Tyr Ser Gly Val Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Cys Tyr Tyr Gly Asn Tyr Asn
        115                 120
```

<210> SEQ ID NO 5
<211> LENGTH: 407
<212> TYPE: DNA
<213> ORGANISM: Homo sapiens

<400> SEQUENCE: 5

```
ttgtagttac catagtagca tcttgcacag aaatatgtag ccgtgtcctc atttttgagg     60
ttgttgatct gcaaataggc agtgctggca gaggtttcca agagaaggc aaaccgtccc    120 ttgaagtcat cagcatatgt tggcactcca gagtaggtgt ttatccagcc catccacttt   180
aaaccctttc ctggagcctg tttcacccag ctcattccat aggttgtgaa ggtatacccca  240 gaagccttgc aggagatctt gactgtctct ccaggcttct tcagctcagg tccagactgt   300
accaactgga tctgtgcttg ggcactttgg gcagctgcca tcaggaatag caagttccac   360
agccaaccca tgatgtctaa aacttgggct cagtggtgcc ttaaaac                 407
```

<210> SEQ ID NO 6
<211> LENGTH: 123
<212> TYPE: PRT
<213> ORGANISM: Homo sapiens

<400> SEQUENCE: 6

```
Met Gly Trp Leu Trp Asn Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45
```

```
Thr Thr Tyr Gly Met Ser Trp Val Lys Gln Ala Pro Gly Lys Gly Leu
        50                  55                  60

Lys Trp Met Gly Trp Ile Asn Thr Tyr Ser Gly Val Pro Thr Tyr Ala
 65                  70                  75                  80

Asp Asp Phe Lys Gly Arg Phe Ala Phe Ser Leu Glu Thr Ser Ala Ser
                 85                  90                  95

Thr Ala Tyr Leu Gln Ile Asn Asn Leu Lys Asn Glu Asp Thr Ala Thr
            100                 105                 110

Tyr Phe Cys Ala Arg Cys Tyr Tyr Gly Asn Tyr
            115                 120

<210> SEQ ID NO 7
<211> LENGTH: 20
<212> TYPE: PRT
<213> ORGANISM: Homo sapiens

<400> SEQUENCE: 7

Cys Pro Thr Met Thr Arg Val Leu Gln Gly Val Leu Pro Ala Leu Pro
 1               5                   10                  15

Gln Val Val Cys
            20

<210> SEQ ID NO 8
<211> LENGTH: 20
<212> TYPE: PRT
<213> ORGANISM: Homo sapiens

<400> SEQUENCE: 8

Cys Pro Thr Met Met Arg Val Leu Gln Ala Val Leu Pro Pro Leu Pro
 1               5                   10                  15

Gln Val Val Cys
            20

<210> SEQ ID NO 9
<211> LENGTH: 20
<212> TYPE: PRT
<213> ORGANISM: Homo sapiens

<400> SEQUENCE: 9

Cys Tyr Thr Arg Asp Leu Val Tyr Lys Asp Pro Ala Arg Pro Lys Ile
 1               5                   10                  15

Gln Lys Thr Cys
            20

<210> SEQ ID NO 10
<211> LENGTH: 27
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (9)..(9)
<223> OTHER INFORMATION: Xaa = hydroxyproline
```

```
<400> SEQUENCE: 10

Ala Pro Pro Pro Pro Pro Pro Cys Xaa Thr Met Thr Arg Val Leu Gln
1               5                   10                  15

Gly Val Leu Pro Ala Leu Pro Gln Val Val Cys
            20                  25
```

ANTIBODY COMPOSITIONS, METHODS FOR TREATING NEOPLASTIC DISEASE AND METHODS FOR REGULATING FERTILITY

CROSS-REFERENCE TO RELATED APPLICATIONS

This application is the National Phase of International Application No. PCT/US2006/0030988, filed Aug. 8, 2006, which claims the benefit of U.S. Provisional Application No. 60/706,506, filed Aug. 8, 2005, the disclosures of which are incorporated herein by reference in their entirety.

FIELD

The invention generally relates to antibody compositions and methods for inhibition of the effects of gonadotropin hormones, including methods for treating cancer and methods for regulating fertility by administering the antibody compositions to a mammalian subject in need thereof.

BACKGROUND

Research in human chorionic gonadotropin (hCG) relates to three elements. A) structure of hCG protein chains and carbohydrates; B) biology of hCG in fertility and cancer; and C) vaccination strategies for immune targeting of hCG, including against hCG peptides, beta chain, or carbohydrates to generate either humoral or T cell-mediated immune responses.

Human chorionic gonadotropin is a 38 kD heterodimeric glycoprotein. Morgan et al., *J. Biol. Chem.* 250: 5247, 1975; Hearn and Gomme, *J. Mol. Recognit.* 13: 223, 2000. Key features of hCG's structure can be seen on diagrams of the primary structure of hCG's alpha and beta chains, as depicted in FIG. 1A. Birken, et al., *Clin Chem* 49: 144, 2003. The alpha subunit of hCG (alpha-hCG, or hCGα in FIG. 1A) is common to glycoprotein hormones including follicle stimulating hormone (FSH), luteinizing hormone (LH), and thyroid stimulating hormone (TSH). Alpha-hCG's protein chain contains 92 amino acids and carries two N-linked oligosaccharides at residues 52 and 78. hCG's hormone-specific beta chain (beta-hCG, or hCGβ in FIG. 1A) contains 145 amino acids. Relative to the highly homologous LH beta chain and unique among the glycoprotein hormones, beta-hCG has an additional 31 amino acids at the carboxyl terminus. 4 Morgan et al., *J. Biol. Chem.* 250: 5247, 1975. This carboxyl terminal peptide (CTP) is both kinky and hydrophilic with nine proline (29 mole %) and eight serine (26 mole %) residues. Beta-hCG carries two N-linked oligosaccharides at residues 13 and 30, as well as four O-linked oligosaccharides at residues 121, 127, 132, and 138.

Tertiary structure of the hCG heterodimer is notable for membership in the cystine knot growth factor family (CKGF) of cytokines. Lapthorn et al., *Nature* 369: 455, 1994; Wu et al., *Structure* 2: 545, 1994. The CKGF family includes glycoprotein hormones, nerve growth factor (NGF), platelet derived growth factor (PDGF), and transforming growth factor-beta (TGF-beta), among at least forty other such proteins. Hearn and Gomme, *J. Mol. Recognit.* 13: 223, 2000. CKGF cytokines are characterized by strong, specific, non-covalent dimerization of two subunits. Each subunit features a remarkable, conserved configuration (knot) of three cystine disulfide bonds in which two disulfides form a ring through which the third disulfide bond passes. Secondary structure is primarily of beta strands. Tertiary structure of each subunit is highly elongated with a high surface:volume ratio and absence of any defined hydrophobic core region. Quaternary structure of hCG comprises head to tail association of subunits along their long axes, involving approximately 25% of their surface area. Dimerization is stabilized by a 21 amino acid loop that extends from the cystine knot of beta-hCG and loops around alpha-hCG, forming a disulfide bonded "seat belt". Beta-hCG may be proteolytically nicked between residues 44 and 45 or 47 and 48 (hCGβn in FIG. 1A). Nicking leads to deactivation of hCG and hastens dissociation of subunits. Cole et al., *J. Clin. Edocrinol. Metab.* 76: 704, 1993. A urinary metabolite, the core fragment of beta-hCG (hCGβcf in FIG. 1A), has no known function. Norman et al., *J. Endocrinol.* 164: 299, 2000; Birken et al., *Arch. Med. Res.* 32: 635, 2001. In addition to the alpha-beta heterodimer, beta-hCG has been found in both monomeric and homodimeric forms. Butler et al., *J. Mol. Endocrinol.* 22: 185, 1999.

Eight oligosaccharides comprise about 30% of hCG's molecular weight. This is more carbohydrate than found on the closest homolog; LH carries only three N-linked oligosaccharides, two on the alpha and one on the beta chain. Each oligosaccharide carries up to two negatively charged terminal sugars. Thus hCG carries a noteworthy net negative charge. Oligosaccharides associated with hCG are highly heterogeneous, accounting for a substantial proportion of the hormone's size and charge heterogeneity.

Alpha-beta heterodimeric hCG binds to and activates the LH/hCG receptor. Ascoli et al., *Endocr. Rev.* 23: 141, 2002. By contrast, none of alpha-hCG, beta-hCG, nicked beta-hCG, or beta-hCG core fragment bind to a recombinant human LH-hCG receptor. Ho et al., *Early Pregnancy* 3: 204, 1997. The carboxyl terminal peptide does not appear to be of any importance to receptor binding or signaling since antibodies specific for this region of beta-hCG do not interfere with LH/hCG receptor signaling. Iverson et al., *Curr. Opin. Mol. Ther.* 5: 156, 2003; Dirnhofer et al., *FAEB J.* 7: 1381, 1993. Chemically deglycosylated hCG binds to but does not activate the rat LH/hCG receptor. Chen et al., *J. Biol. Chem.* 257: 14446, 1982. Individual N-linked carbohydrate moieties likely do not affect hCG function. Hearn and Gomme, *J. Mol. Recognit.* 13: 223, 2000.

Human chorionic gonadotropin has a demonstrated role in reproduction. Ascheim and Zondek, *Klin. Wochenschr* 248, 1927. hCG is obligately required for reproduction and appears to have myriad roles in pregnancy given the expression in many tissues of LH/hCG receptors. Rao, *Semin. Reprod. Med.* 19: 7, 2001; Filicori et al., *Fertil. Steril* 84: 275, 2005. Some of these proposed receptor-mediated roles include facilitation of cytotrophoblast invasion, angiogenesis, and immunosuppression (Islami et al., *Semin. Reprod. Med.* 19: 49, 2001; Licht et al., *Semin. Reprod. Med.* 19: 37, 2001), as well as inhibition of apoptosis. Kuroda et al., *Int. J. Cancer* 91: 309, 2001. In addition, the net negative charge conferred by extensive sialylation of hCG on the syncitiotrophoblast surface could by itself also be immunosuppressive. Van et al., *Int. J. Cancer* 38: 915, 1986.

In non-pregnant states, serum hCG may be present at low concentrations via pulsatile secretion of scant quantities from the anterior pituitary. Birken et al., *Endocrinology* 137: 1402, 1996. Yet hCG is also produced by cancer cells of many non-reproductive tissues. Cosgrove et al., *Biochim. Biophys. Acta.* 1007: 44, 1989; Stenman et al., *Clin. Biochem.* 37: 549, 2004. Given the parallels between human reproduction and malignant transformation, hCG has thus been proposed to be a marker of malignant transformation. Acevedo, *J. Exp. Ther. Oncol.* 2: 133, 2002; Murray and Lessey, *Semin. Reprod. Endocrinol.* 17: 275, 1999. Consistent with this, alpha-beta heterodimeric hCG has been shown to block cisplatin-induced apoptosis in ovarian carcinoma cells that express the LH/hCG receptor. Kuroda et al., *Int. J. Cancer* 76: 571, 1998. However, hCG is neither sensitive nor specific for malignancy.

Two surprising observations have been made concerning hCG's putative role in cancer. First, membrane-bound hCG was found on the surface of many different types of cultured cancer cells. Acevedo et al., Cancer 69: 1829, 1992. This was noteworthy because hCG is a secreted protein with no transmembrane domain. Second, serum beta-hCG was noted to be associated with more aggressive, metastatic presentations of bladder cancer. Iles et al., Br. J. Urol. 64: 241, 1989. Also metastatic phenotype was found to correlate with expression of beta-hCG in an animal model. Acevedo and Hartsock, Cancer 78: 2388, 1996. These findings were of uncertain significance because beta-hCG does not bind to the LH/hCG receptor. Subsequently, hCG-beta has been found by multivariate analysis to be an independent negative prognostic indicator in six different epithelial cancers including colorectal, gastric, oral, pancreatic, ovarian, and renal cell. Louhimo et al., Int. J. Cancer 101: 545, 2002; Louhimo et al., Int. J. Cancer 111: 929, 2004; Hedstrom et al., Int. J. Cancer 84: 525, 1999; Louhimo et al., Oncology 66: 126, 2004; Vartianinen et al., Int. J. Cancer 95: 313, 2001; Hotakainen et al., Br. J. Cancer 86: 185, 2002. Curiously, while tissue levels of beta-hCG by immunohistochemistry were also negatively prognostic in colorectal cancer, only serum beta-hCG was significantly prognostic in renal cell carcinoma. Lundin et al., Int. J. Cancer 95: 18, 2001; Hotakainen et al., Int. J. Cancer 104: 631, 2003. Thus soluble beta-hCG can now be presumed to play an important role in cancer progression.

Beta-hCG was found to inhibit apoptosis of bladder cancer cells in vitro as either a monomer or homodimer. Butler et al., *Br. J. Cancer* 82: 1553, 2000; Butler and Iles, *Tumour Biol.* 25: 18, 2004. The authors propose a mechanism in which beta-hCG blocks apoptosis mediated by TGF-beta via binding to without activating TGF-beta receptors. Similarly, one can imagine that beta-hCG could inhibit activity of another CKGF cytokine, PDGF. Pietras et al., *Cancer Res.* 62: 5476, 2002. Engineered expression of beta-hCG in prostate cancer cells has been shown to down-regulate E-cadherin and upregulate invasiveness. Wu and Walker, Cancer 106: 68, 2006. In the latter experiments, conditioned medium was found to confer the same effect, indicating that soluble beta-hCG in the culture supernatant produced this effect. Although the receptor in this instance is unknown, there are at least 40 CKGF cytokine family members (Hearn and Gomme, *J. Mol. Recognit.* 13: 223, 2000), so involvement of additional, as yet unidentified receptor(s) is likely. The finding that hCG has been shown to inhibit Kaposi's sarcoma has not been thought to be mutually exclusive with hCG's role in diverse epithelial cancers of broader public health significance. Butler and Iles, *Clin Cancer Res.* 9: 4666, 2003.

Vaccination targeting hCG to regulate fertility has been pursued for decades. Naz et al., *Hum. Reprod.* 20: 3271, 2005. At the outset these vaccines sought to generate active specific humoral immunity either to the CTP of beta-hCG or to full-length beta-hCG. Lee et al., *Mol. Immunol.* 17: 749, 1980; Talwar et al., *Proc. Natl. Acad. Sci. U.S.A.* 91: 8532, 1994. Efficacy of such vaccines has in principle been demonstrated. Stevens et al., *Fertil. Steril.* 36: 98, 1981; Talwar et al., *Proc. Natl. Acad. Sci. U.S.A.* 91: 8532, 1994. Embellishments of these approaches have employed different beta-hCG components or recombinant antigen expression as fusion proteins. Rock et al., *Vaccine* 14: 1560, 1996; Rout and Vrati, *Vaccine* 15: 1503, 1997; Xu et al., *Sheng Wu Gong. Cheng. Xue. Bao.* 20: 49, 2004; Yankai et al., *Biochem. Biophys. Res. Commun.* 345: 1365, 2006; Geissler et al., *Lab Invest.* 76: 859, 1997.

Similar approaches have been pursued for cancer treatment. Triozzi and Stevens, *Oncol. Res.* 6: 7, 1999; Moulton et al., *Clin. Cancer Res.* 8: 2044, 2002. Additional refinements have included passively administered antibodies (Butler et al., *Oncol. Res.* 14: 93, 2003), monoclonal antibodies specific for the CTP (Kalantarov and Acevedo, Cancer 83: 783, 1998), genetic immunization (Geissler et al., *Lab Invest.* 76: 859, 1997), and a targeted fusion protein to generate active T cell mediated immunity against beta-hCG. He et al., *Clin. Cancer Res.* 10: 1920, 2004. A further alternative seeks to target via a monoclonal antibody the O-linked core 2 sugar-containing oligosaccharide isoforms displayed on the CTP of hyperglycosylated hCG (H-hCG). Birken et al., *Arch. Med. Res.* 32: 635, 2001; Birken et al., *Endocrine* 10: 137, 1999; Birken, *Tumour Biol.* 26: 131, 2005; Cole et al., *Gynecol. Oncol.* 102: 145, 2006; U.S. Pat. No. 6,764,680; U.S. Patent Application No. 2005/0260196.

Most of the above approaches employ an active immunization strategy. Thus months are required for either antibody or T cell mediated immunity to develop, and some recipients will fail to generate an adequate immune response. None of the above approaches to immune targeting of beta-hCG or H-hCG seeks explicitly to block binding of beta-hCG to the LH/hCG or any other receptor. In particular, formulations targeting either the CTP or H-hCG don't block receptor binding. Although experimental methods have been developed to allow targeting of cancer cells that bear surface-bound beta-hCG, the weight of data on beta-hCG's prognostic significance argues that blockade of serum beta-hCG binding to receptors mediating deleterious effects will be critically important in treatment of cancer by immune targeting of hCG. Furthermore, none of the above approaches have been shown to synergize with cancer chemotherapy.

Thus a need exists in the art to generate more effective treatment of cancers that secrete beta-hCG. To address this problem, means are needed to target beta-hCG in a manner that fulfills the following two criteria. First, the agent generated should be able to target serum beta-hCG quickly following passive administration. In practice this could be accomplished by use of monoclonal antibodies or similar mediators of immune specificity. Second, the method must generate treatment that blocks binding of beta-hCG to its receptor(s) mediating deleterious effects associated with cancer progression. In practice this implies generation of immune specificity for an epitope that is both conformationally defined and surface-accessible.

SUMMARY

The present invention generally relates to antibody compositions and methods for inhibition of the effects of gonadotropin hormones, including methods for treating cancer and methods for regulating fertility by administering the antibody compositions to a mammalian subject in need thereof. The invention further relates to inhibition of binding of the human chorionic gonadotropin beta chain to any of its cognate receptors and to consequential inhibitory effects on growth of human cancers.

A method for treating a neoplastic disease in a mammalian subject is provided which comprises administering to the mammal subject a pharmaceutical composition comprising an antibody which specifically binds to β-L2 loop of human chorionic gonadotropin (hCG) in an amount effective to reduce or eliminate the neoplastic disease in the mammalian subject. In the method, the antibody can comprise an amino acid sequence of SEQ ID NO:2 or SEQ ID NO:4. The antibody can be a human monoclonal antibody 2B2.6F5 (ATCC Patent Deposit Designation No. PTA-7777) or a human monoclonal antibody 2B3.3E8 (ATCC Patent Deposit Designation No. PTA-7775). Antibody compositions are provided which comprise an amino acid sequence of SEQ ID NO:2 or SEQ ID NO:4. Antibody compositions are provided which comprise a human monoclonal antibody 2B2.6F5 (ATCC Patent Deposit Designation No. PTA-7777) or a human monoclonal antibody 2B3.3E8 (ATCC Patent Deposit Designation No. PTA-7775). In a further aspect, the antibody is linked to a cytotoxic agent, e.g., a cytotoxic drug or a radioactive isotope. In a further aspect, the method for treating neoplastic disease further comprises administering a pharmaceutical composition comprising a chemotherapeutic agent in combination with the monoclonal antibody to the mammalian subject.

A method for inducing abortion in a mammalian subject is provided which comprises administering to the mammal subject a pharmaceutical composition comprising a human monoclonal antibody 2B2.6F5 (ATCC Patent Deposit Designation No. PTA-7777) or a human monoclonal antibody 2B3.3E8 (ATCC Patent Deposit Designation No. PTA-7775), which specifically binds to human chorionic gonadotropin in an amount effective to inducing abortion in the mammalian subject. A method for reducing fertility in a mammalian subject is provided which comprises administering to the mammal subject a pharmaceutical composition comprising a human monoclonal antibody 2B2.6F5 (ATCC Patent Deposit Designation No. PTA-7777) or a human monoclonal antibody 2B3.3E8 (ATCC Patent Deposit Designation No. PTA-7775), which specifically binds to human chorionic gonadotropin in an amount effective to reduce fertility in the mammalian subject. The antibody can further comprise an amino acid sequence of SEQ ID NO:2 or SEQ ID NO:4.

An isolated monoclonal antibody is provided which binds to human chorionic gonadotropin comprising an amino acid sequence in its heavy chain variable region as set forth in SEQ ID NO:2 or an amino acid sequence which is at least 90% homologous to SEQ ID NO:2.

An isolated monoclonal antibody which binds to human chorionic gonadotropin comprising an amino acid sequence in its heavy chain variable region as set forth in SEQ ID NO:4 or an amino acid sequence which is at least 90% homologous to SEQ ID NO:4.

An isolated monoclonal antibody is provided which binds to human chorionic gonadotropin comprising an amino acid sequence in its light chain variable region and a heavy chain variable region, wherein the heavy chain variable region is set forth in SEQ ID NO:2 or SEQ ID NO:4 or an amino acid sequence which is at least 90% homologous to in SEQ ID NO:2 or SEQ ID NO:4.

In one aspect, the isolated monoclonal antibody has one or more of the following characteristics: (i) inhibits proliferation in vitro of BXPC-3 pancreatic carcinoma cells; and (ii) does not inhibit proliferation in vitro of MCF-7 breast carcinoma cells or HeLa cells. In a further aspect, the antibody has a dissociation equilibrium constant ($K_D$) of approximately $10^{-8}$ M or less, when determined by surface plasmon resonance (SPR) using recombinant human chorionic gonadotropin as an analyte and the antibody as a ligand. the antibody is capable of binding human chorionic gonadotropin with a binding affinity of about $10^8$ $M^{-1}$ or greater. The isolated monoclonal antibody can be an antibody fragment or a single chain antibody.

The isolated monoclonal antibody can be a binding-domain immunoglobulin fusion protein comprising (i) a variable heavy chain amino acid sequence as set forth in SEQ ID NO:2 or a variable heavy chain sequence which is at least 90% homologous to SEQ ID NO:2, fused to a variable light chain amino acid sequence via a linker peptide, that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The isolated monoclonal antibody can be a binding-domain immunoglobulin fusion protein comprising (i) a variable heavy chain amino acid sequence as set forth in SEQ ID NO:4 or a variable heavy chain sequence which is at least 90% homologous to SEQ ID NO:4, fused to a variable light chain amino acid sequence via a linker peptide, that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The isolated monoclonal antibody can bind to a predetermined antigen with an equilibrium association constant (Ka) of at least $10^{10}$ $M^{-1}$. The isolated monoclonal antibody can be bind to a predetermined antigen with an equilibrium association constant (Ka) of at least $10^9$ $M^{-1}$. The antibody can bind to a predetermined antigen with an equilibrium association constant (Ka) of at least $10^8$ $M^{-1}$.

An isolated human monoclonal antibody is provided which binds to human chorionic gonadotropin comprising an amino acid sequence in its human heavy chain variable region as set forth in SEQ ID NO:2 or an amino acid sequence which is at least 90% homologous to SEQ ID NO:2. An isolated human monoclonal antibody is provided which binds to human chorionic gonadotropin comprising an amino acid sequence in its human heavy chain variable region as set forth in SEQ ID NO:4 or an amino acid sequence which is at least 90% homologous to SEQ ID NO:4. A pharmaceutical composition is provided which comprises the antibody and a pharmaceutically acceptable carrier. An isolated recombinant anti-human chorionic gonadotropin antibody or antigen-binding fragment thereof, said antibody is provided which comprises a human constant region wherein said antibody or antigen binding fragment (i) competitively inhibits binding of 2B2.6F5 antibody (ATCC Patent Deposit Designation No. PTA-7777) to human chorionic gonadotropin, and (ii) binds to a neutralizing epitope of human chorionic gonadotropin in vivo with an affinity of at least $1 \times 10^8$ liter/mole, measured as an associate constant (Ka) as determined by surface plasmon resonance. An isolated recombinant anti-human chorionic gonadotropin antibody or antigen-binding fragment thereof, said antibody is provided which comprises a human constant region wherein said antibody or antigen binding fragment (i) competitively inhibits binding of 2B3.3E8 antibody (ATCC Patent Deposit Designation No. PTA-7775) to human chorionic gonadotropin, and (ii) binds to a neutralizing epitope of human chorionic gonadotropin in vivo with an affinity of at least $1 \times 10^8$ liter/mole, measured as an associate constant (Ka) as determined by surface plasmon resonance.

A method of detecting human chorionic gonadotropin in a sample is provided, wherein the method comprises (a) providing a sample; (b) contacting the sample of (a) with a human monoclonal antibody 2B2.6F5 (ATCC Patent Deposit Designation No. PTA-7777) or a human monoclonal antibody 2B3.3E8 (ATCC Patent Deposit Designation No. PTA-7775), which specifically binds a polypeptide comprising human chorionic gonadotropin under conditions which permit binding of the polypeptide ligand to human chorionic gonadotropin; and (c) detecting binding of the antibody 2B2.6F5 or antibody 2B3.3E8 with human chorionic gonadotropin in the sample, wherein detection of binding indicates the presence of human chorionic gonadotropin in the sample; thereby detecting human chorionic gonadotropin in the sample.

A isolated human monoclonal antibody is provided which specifically binds to amino acids 38-57 of the β-L2 loop of human chorionic gonadotropin (SEQ ID NO:7) or an analog thereof. In one aspect, the antibody blocks binding of hCG to LH/hCG receptor.

A method for diagnosing cancer in a mammalian subject suspected of having neoplastic disease or suspected of being at risk for neoplastic disease is provided which comprises obtaining a test sample from blood or tissue of the subject, the test sample comprising a cell population providing a human monoclonal antibody 2B2.6F5 (ATCC Patent Deposit Designation No. PTA-7777) or a human monoclonal antibody 2B3.3E8 (ATCC Patent Deposit Designation No. PTA-7775) to detect the presence or absence of an human chorionic gonadotropin marker on the cells within the cell population, and analyzing the cell population detected by the human chorionic gonadotropin marker to identify and characterize the cells, the presence of human chorionic gonadotropin marker on or in the cells indicative of neoplastic disease or risk of neoplastic disease in the mammalian subject.

A method of screening a drug candidate compound for treatment of cancer in a mammalian subject is provided which comprises administering a therapeutically effective amount of the drug candidate compound to the subject suspected of having cancer, obtaining test samples from blood or tissue of the subject before and after treatment with the drug candidate compound, the test samples comprising a cell population suspected of containing tumor cells, providing a human monoclonal antibody 2B2.6F5 (ATCC Patent Deposit Designation No. PTA-7777) or a human monoclonal antibody 2B3.3E8 (ATCC Patent Deposit Designation No. PTA-7775), to detect the presence or absence of an human chorionic gonadotropin marker on the cells in the test sample, analyzing the cell population detected by the human chorionic gonadotropin marker to identify the tumor cells in the test samples before treatment with the drug candidate compound compared to after treatment with the drug candidate compound, wherein the presence of a decreased number of the tumor cells in the specimen after treatment compared to a number of the tumor cells in a specimen before treatment indicating effectiveness of the drug candidate compound in treating the cancer in the mammalian subject.

BRIEF DESCRIPTION OF THE DRAWINGS

FIG. 1B shows amino acid sequence in vicinity of beta-hCG L2 long loop.

FIG. 6 shows relative affinity of monoclonal antibodies for hCG versus LH.

FIG. 7 shows monoclonal antibody blocking of hCG binding to LH/hCG receptor.

FIG. 8 shows an effect of antibody on the growth of cancer cells in vitro.

FIG. 9 shows synergy with chemotherapy of monoclonal antibody to inhibit growth of cancer cells in vitro.

FIG. 10 shows an effect of monoclonal antibody on tumor growth in vivo.

FIG. 11 shows DNA and amino acid sequences of mAb 2B2.6F5 heavy chain DNA and amino acid sequence, mAb 2B3.3E8 heavy chain DNA and amino acid sequence, and mAb 2B3.3F5 heavy chain DNA and amino acid sequence.

DETAILED DESCRIPTION

The invention relates to the field of vaccines including antibodies that target human chorionic gonadotropin (hCG) or that target a substituent component of hCG. The invention relates to antibody compositions and methods for inhibition of the effects of gonadotropin hormones, including methods for treating cancer and methods for regulating fertility by administering the antibody compositions to a mammalian subject in need thereof. The invention further relates to inhibition of binding of the human chorionic gonadotropin beta chain to any of its cognate receptors and to consequential inhibitory effects on growth of human cancers. The binding inhibition can be demonstrated with antibody compositions of the present invention.

Antibody compositions of the invention are targeted to beta-hCG to provide more effective methods for treatment of cancers and methods for regulating fertility wherein the cells secrete beta-hCG. The antibodies can target beta-hCG in a manner that fulfills the following two criteria. First, the antibody compositions should be able to target serum beta-hCG quickly following passive administration. In practice this can be accomplished by use of monoclonal antibodies or similar mediators of immune specificity. Second, the method must generate a therapeutic treatment that blocks binding of beta-hCG to its receptor(s) mediating deleterious effects associated with cancer progression or methods for regulating fertility. In practice this implies generation of immune specificity for an epitope that is both conformationally defined and surface-accessible.

Such a method might be accomplished by generation of immune specificity for the beta-hCG L2 long loop, which includes surface-accessible amino acids at positions 48 through 53. A cyclic peptide of beta-hCG positions 38-57 inhibited binding of hCG to rat ovarian membrane receptor and testosterone production by Leydig cells. Keutmann, et al., *Proc. Natl Acad. Sci. U.S.A.* 84: 2038-2042, 1987. However, confirmation of binding inhibition could not be replicated in two separate systems. Salesse, et al., *Mol. Cell. Endocrinol.* 68: 113-119, 1990; Jagtap, et al., *J Endocrinol.* 172: 311-320, 2002. Polyclonal antisera raised against the conformational epitope produced by this cyclic peptide were able to neutralize the hormone in an in vivo assay, suggesting that the epitope is in the vicinity of the receptor binding site. On the other hand, this finding could also have followed from more rapid clearance of the bound hCG. Finally, the L2 long loop is known to be cleaved between residues 44 and 45, as well as residues 47 and 48. Such cleavage alters antibody binding and might interfere with the approach proposed. In summary, blocking receptor binding by β-hCG would be useful for cancer treatment and fertility regulation. The present invention provides antibody compositions having immune specificity for the β-hCG L2 long loop that have been demonstrated to block LH/hCG receptor binding by β-hCG.

Figure 1A:
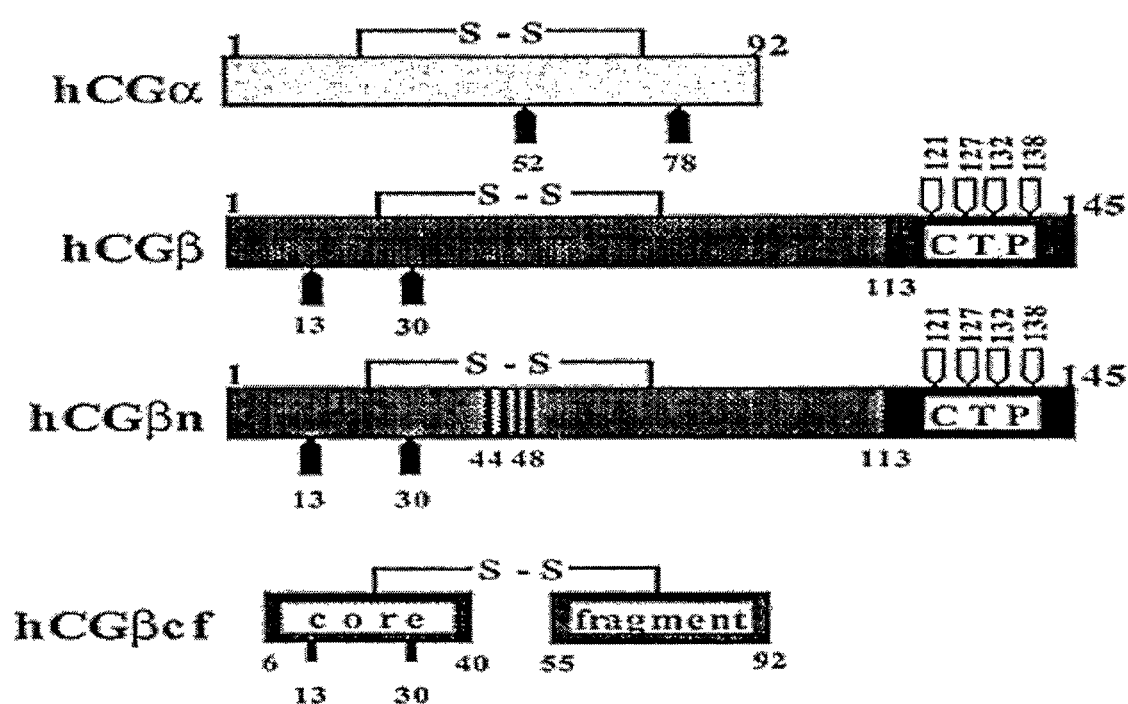
FIG. 1A shows diagrams of structures of hCG and metabolites.

FIG. 1B shows amino acid sequences from the beta chains of hCG, LH, and FSH that correspond to the L2 beta long loop of the HCG and HCG beta chain protein structure. The L2 beta long loop describes a region of the beta-hCG protein chain's known three-dimensional structure that is composed of two strands of amino acids that are joined by a hairpin turn. "L2" indicates that this is the second of three hairpin turns between strands in the HCG beta protein sequence. Number 2 in the figure refers to amino acid numbering of the beta-hCG protein chain from amino acid positions 38 to 57 in the L2 beta long loop. Number 4 indicates amino acids comprising an immunogen that enables selection of monoclonal antibodies or related proteins that specifically target the L2 beta long loop of a particular gonadotropin beta chain, for example hCG. Number 6 indicates surface-accessible amino kids in the L2 beta long loop of the HCG protein crystal structure. Number 8 indicates a non-conservative amino acid (51 A→P) difference between HCG and LH that enables specific targeting of HCG vs. LH.

Figure 2:
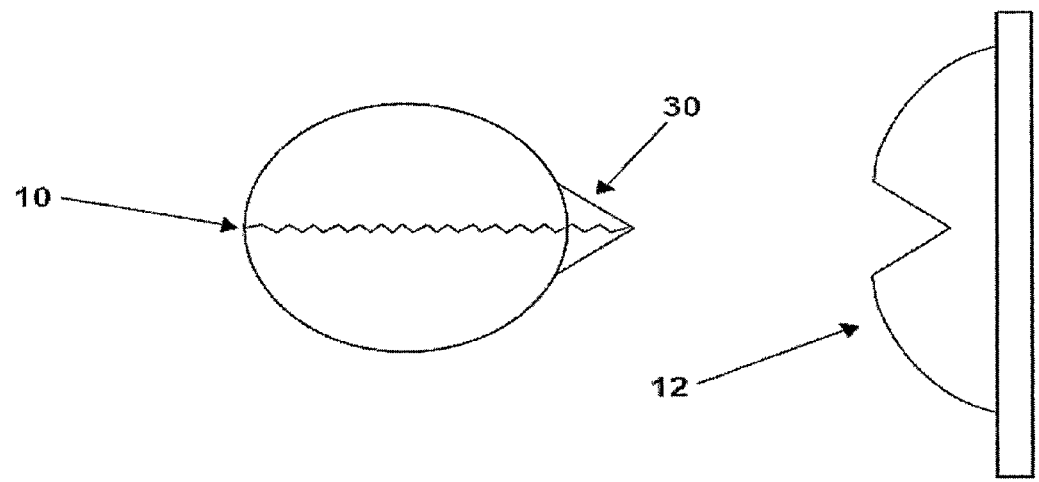
FIG. 2 shows a schematic depiction of gonadotropin heterodimer and hCG beta chain binding to respective receptors.
Figure 2:
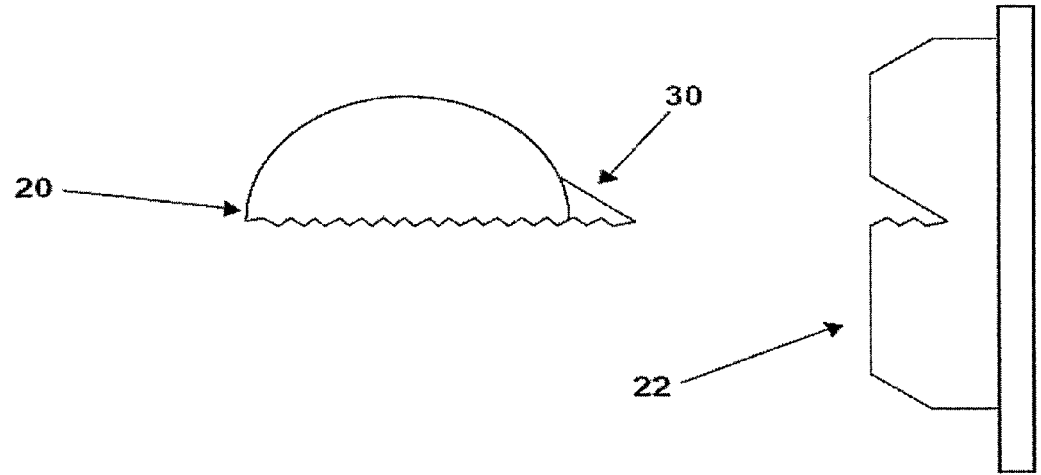

FIG. 2 shows a schematic depiction of binding of heterodimeric gonadotropin and HCG beta chain to their respective receptors. Number 10 refers to a heterodimeric gonadotropin, such as HCG, LH, or FSH. Number 12 refers to a gonadotropin receptor, including LH-HCG, FSH, and TSH receptors. Number 20 refers to the hCG beta chain in a form without an associated common alpha chain glycoprotein hormone chain, including monomeric, homodimeric, or other multimeric forms. Number 22 depicts receptor(s) to which HCG beta binds, separate and distinct from the LH-HCG, FSH, and TSH receptors. Number 30 refers to the L2 beta hairpin loop of gonadotropin beta chain. This is the specific region of gonadotropin protein structure that is targeted by the invention described here.

Figure 3:
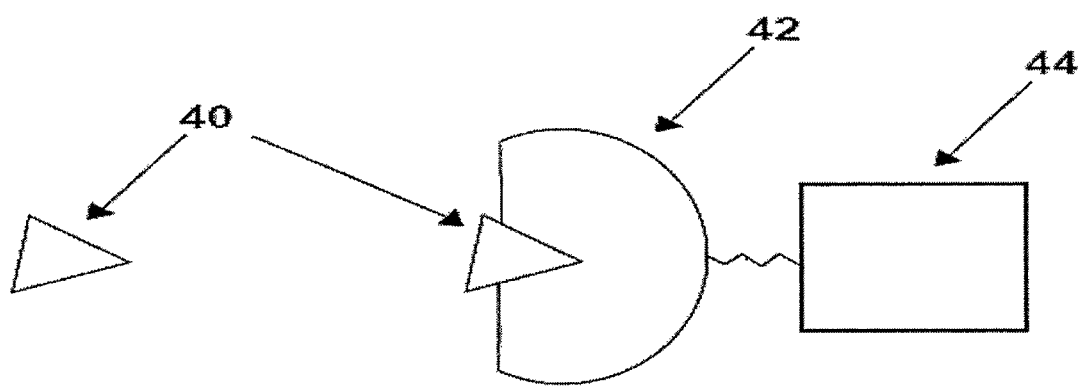
FIG. 3 shows a schematic depiction of generation of immune specificity for gonadotropin L2 beta long loop.

FIG. 3 shows the method described herein to induce immune specificity for the L2 beta long loop of gonadotropins. Number 40 represents the beta-hCG L2 long loop amino acid sequence (38-57) of the gonadotropin beta chain. This sequence is bounded by two cysteine moieties that can be induced to form an intramolecular cystine disulfide bond, causing cyclization of the peptide. Although a 38-57 cystine disulfide bond is not formed in the native gonadotropin protein structure, formation of the intramolecular disulfide bond in the 38-57 sequence induces a three-dimensional conformation that approximates the native L2 beta long loop. Such cyclized peptide(s) can be covalently linked to a carrier protein such as diphtheria toxoid in order to boost the antipeptide immune response in animal(s) or in vivo experimental system(s) that are used to generate monoclonal antibodies or related proteins conferring immune specificity. Formation of the 38-57 disulfide bond thus enables selection of monoclonal antibodies or related proteins that are specific for the gonadotropin L2 beta long loop. Number 42 represents a monoclonal antibody that confers immune specificity for the L2 beta long loop of the HCG beta chain and is generated in response to Number 40. Number 44 represents any covalently linked small molecule or macromolecule that influences effector function(s). Such effector functions modify the outcome of the immune specificity (Part 42) that targets the gonadotropin L2 beta long loop.

Figure 4:
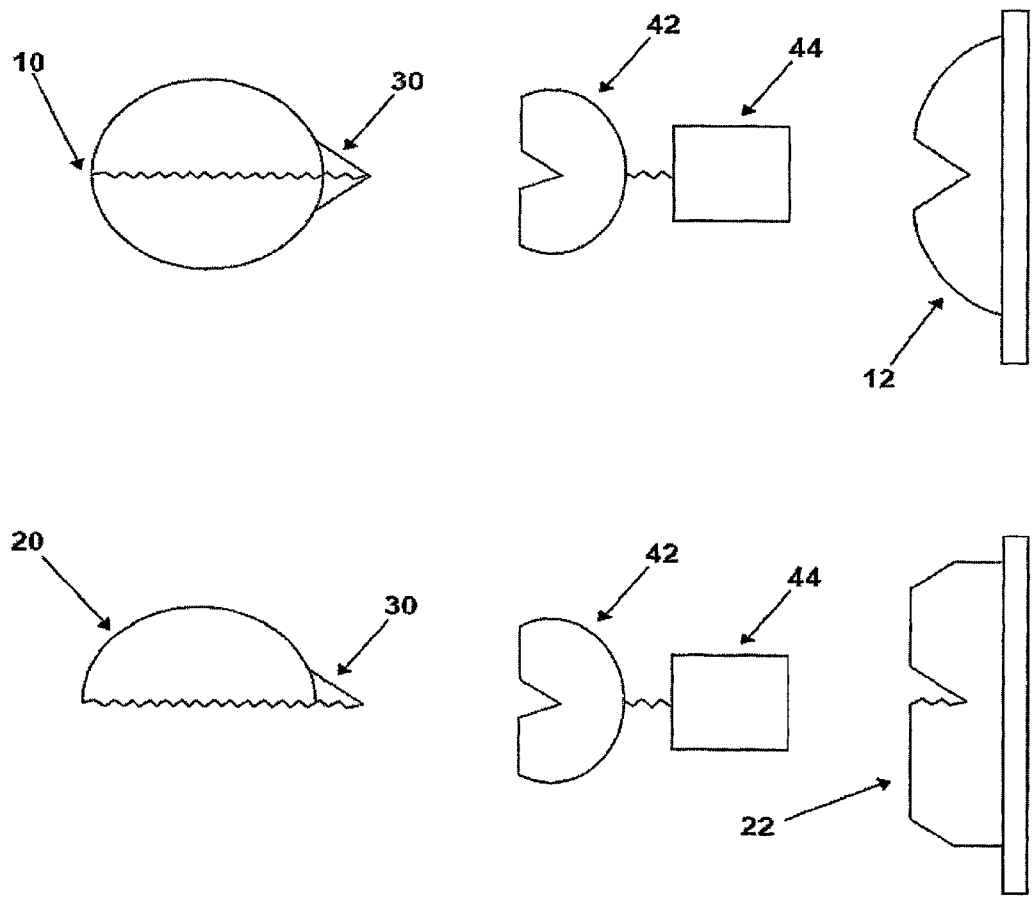
FIG. 4 shows a schematic depiction of blockade of receptor binding by monoclonal antibody specific for gonadotropin L2 beta loop.

FIG. 4 shows schematically the action of a monoclonal antibody (42) with immune specificity for the L2 beta long loop (30) in preventing binding to receptors (12, 22) by heterodimeric gonadotropin(s) (10) or the HCG beta chain (20) and any consequent intracellular signalling events. Thus this invention blocks receptor binding of the beta-hCG protein regardless of whether it is in the form of heterodimeric hCG, monomeric beta-hCG, or homodimeric beta-hCG. Alternative embodiments may be based on a fragment of such a monoclonal antibody (42) and/or a recombinant formulation of such a protein that provides immune specificity for the L2 beta long loop (30). Additional alternative embodiments may be derived by engineering an immune effector function (44) that is different from the constant domains of the original monoclonal antibody.

Figure 5:
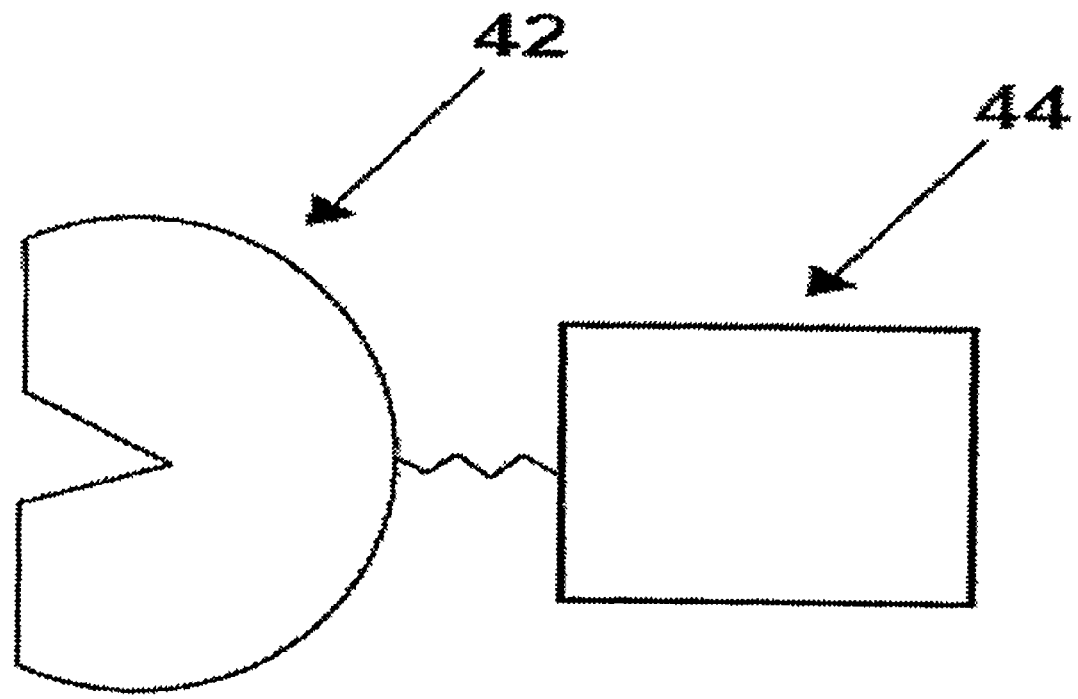
FIG. 5 shows a schematic depiction of immune effector function targeted by antibody binding fragment that confers specificity on gonadotropin beta chain.

FIG. 5 shows potential immune effector function(s) (44) that are separate, distinct, and/or additive to those inherent to a monoclonal antibody or fragment that provides specificity for, the gonadotropin L2 beta long loop.

Reference numerals in FIGS. 1-5 refer to: Amino acid numbering of HCG beta chain (2); Immunogen to induce immune specificity for L2 beta long loop (4); Surface-accessible amino acids of HCG in L2 beta long loop (6); Basis of LH versus HCG beta chain immune specificity (8); Heterodimeric gonadotropin (10); Heterodimeric gonadotropin recepto (12); HCG beta chain (20); Receptor(s) to which HCG beta chain binds (22); L2 beta hairpin loop of gonadotropin beta chain (30); 38-57 loop peptide of HCG beta chain (40); Protein conferring humoral immune specificity to gonadotropin beta chain (42); Protein conferring immune effector function (44).

The present invention provides an antibody composition that binds to the L2 long loop of beta-hCG protein. The antibody compositions can be used in methods for treating neoplastic disease, in methods for inducing abortions in a mammalian subject, and in methods for reducing fertility in a mammalian subject. The antibody compositions can comprise an amino acid sequence of SEQ ID NO:2 or SEQ ID NO:4. The antibody can further comprise a human monoclonal antibody 2B2.6F5 (ATCC Patent Deposit Designation No. PTA-7777) or a human monoclonal antibody 2B3.3E8 (ATCC Patent Deposit Designation No. PTA-7775).

In a further aspect, methods for treating disease in a mammalian subject are provided which comprise administering monoclonal antibodies directed to follicle stimulating hormone (FSH), leutinizing hormone (LH) or thyroid stimulating hormone (TSH), wherein the disease is reduced or eliminated in the mammalian subject. In a detailed aspect the monoclonal antibodies are directed to the L2 long loop of the beta subunit polypeptide of FSH, LH or TSH.

It is to be understood that this invention is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Patient", "subject" or "mammal" are used interchangeably and refer to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles.

"Treating" or "treatment" includes the administration of the antibody compositions, compounds or agents of the present invention to prevent or delay the onset of the symptoms, complications, or biochemical indicia of a disease, alleviating the symptoms or arresting or inhibiting further development of the disease, condition, or disorder (e.g., cancer, metastatic cancer, metastatic epithelial cancer, colorectal carcinoma, gastric carcinoma, oral carcinoma, pancreatic carcinoma, ovarian carcinoma, or renal cell carcinoma). Treatment can be prophylactic (to prevent or delay the onset of the disease, or to prevent the manifestation of clinical or subclinical symptoms thereof) or therapeutic suppression or alleviation of symptoms after the manifestation of the disease.

"Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancerous" or "malignant cell" is understood as a cell having specific structural properties, lacking differentiation and being capable of invasion and metastasis. Examples of cancers are, breast, lung, brain, bone, liver, kidney, colon, and prostate cancer. (see DeVita et al., Eds., *Cancer Principles and Practice of Oncology*, 6th. Ed., Lippincott Williams & Wilkins, Philadelphia, Pa., 2001; this reference is herein incorporated by reference in its entirety for all purposes).

Cancer-associated" refers to the relationship of a nucleic acid and its expression, or lack thereof, or a protein and its level or activity, or lack thereof, to the onset of malignancy in a subject cell. For example, cancer can be associated with expression of a particular gene that is not expressed, or is expressed at a lower level, in a normal healthy cell. Conversely, a cancer-associated gene can be one that is not expressed in a malignant cell (or in a cell undergoing transformation), or is expressed at a lower level in the malignant cell than it is expressed in a normal healthy cell.

In the context of the cancer, the term "transformation" refers to the change that a normal cell undergoes as it becomes malignant. In eukaryotes, the term "transformation" can be used to describe the conversion of normal cells to malignant cells in cell culture.

"Proliferating cells" are those which are actively undergoing cell division and growing exponentially. "Loss of cell proliferation control" refers to the property of cells that have lost the cell cycle controls that normally ensure appropriate restriction of cell division. Cells that have lost such controls proliferate at a faster than normal rate, without stimulatory signals, and do not respond to inhibitory signals.

"Advanced cancer" means cancer that is no longer localized to the primary tumor site, or a cancer that is Stage III or IV according to the American Joint Committee on Cancer (AJCC).

"Well tolerated" refers to the absence of adverse changes in health status that occur as a result of the treatment and would affect treatment decisions.

"Metastatic" refers to tumor cells, e.g., human epithelial cancer, colorectal carcinoma, gastric carcinoma, oral carcinoma, pancreatic carcinoma, ovarian carcinoma, or renal cell carcinoma, that are able to establish secondary tumor lesions in the alimentary tract, kidney, pancrease, ovaries, lungs, liver, bone or brain of immune deficient mice upon injection into the mammary fat pad and/or the circulation of the immune deficient mouse.

"Non-metastatic" refers to tumor cells, e.g., human epithelial cancer cells, that are unable to establish secondary tumor lesions in the lungs, liver, bone or brain or other target organs of epithelial cell metastasis, e.g., colorectal carcinoma, gastric carcinoma, oral carcinoma, pancreatic carcinoma, ovarian carcinoma, or renal cell carcinoma in immune deficient mice upon injection into the mammary fat pad and/or the circulation. The human tumor cells used herein and addressed herein as non-metastatic are able to establish primary tumors upon injection into the mammary fat pad of the immune deficient mouse, but they are unable to disseminate from those primary tumors.

"Lymphocyte" as used herein has the normal meaning in the art, and refers to any of the mononuclear, nonphagocytic leukocytes, found in the blood, lymph, and lymphoid tissues, e.g., B and T lymphocytes.

"Disease caused by hormonal imbalance" refers to diseases caused by an imbalance of gonadotropin hormone, for example, human chorionic gonadotropin, in the mammalian subject. Disease caused by hormonal imbalance include, but are not limited to, prostate cancer, polycystic ovary disease, rheumatic disease, septic shock, endometriosis, leiomyomatosis, ovarian degeneration during cytotoxic chemotherapy, or Alzheimer's disease. "Disease caused by hormonal imbalance" further refers to diseases caused by an imbalance of gonadotropin hormone, for example, follicle stimulating hormone (FSH), leutinizing hormone (LH) or thyroid stimulating hormone (TSH), in the mammalian subject.

"Polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to human chorionic gonadotropin β chain (β-hCG), under suitable binding conditions, (2) ability to block β-hCG binding to an leutinizing hormone (LH)/hCG receptor, or (3) ability to β-hCG-expressing cell growth in vitro or in vivo. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, *J. Adv. Drug Res.* 15: 29, 1986; Veber and Freidinger *TINS* p. 392 (1985); and Evans et al. *J. Med. Chem.* 30: 1229, 1987, which are incorporated herein by reference. Such compounds are often developed with the aid of computerized molecular modeling. Peptide mimetics that are structurally similar to therapeutically useful peptides may be used to produce an equivalent therapeutic or prophylactic effect.

Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —CH$_2$NH—, —CH$_2$S—, —CH=CH-(cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61: 387, 1992, incorporated herein by reference); for example, by adding internal cysteine residues capable of forming intramolecular disulfide bridges which cyclize the peptide.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99% homology. In particular, conservative amino acid replacements are contemplated. Conservative amino acid replacement does not against the overall homology which can be maintained at least 75%, more preferably at least 80%, 90%, 95%, and most preferably 99% homology. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253: 164, 1991. Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. *Nature* 354: 105, 1991, which are each incorporated herein by reference.

"Antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An intact "antibody" comprises at least two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH$_1$, CH$_2$ and CH$_3$. Each light chain is comprised of a light chain variable region (abbreviated herein as LCVR or V$_L$) and a light chain constant region. The light chain constant region is comprised of one domain, C$_L$. The V$_H$ and V$_L$ regions can be further subdivided into regions of hypervariability, termed complementarity determining regions (CDR), interspersed with regions that are more conserved, termed framework regions (FR). Each V$_H$ and V$_L$ is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system. The term antibody includes antigen-binding portions of an intact antibody that retain capacity to bind β-hCG. Examples of binding include (i) a Fab fragment, a monovalent fragment consisting of the $V_L$, $V_H$, $C_L$ and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the $V_L$ and $V_H$ domains of a single arm of an antibody, (v) a dAb fragment (Ward et al., *Nature* 341: 544-546, 1989), which consists of a VH domain; and (vi) an isolated complementarity determining region (CDR).

An antibody other than a "bispecific" or "bifunctional" antibody is understood to have each of its binding sites identical. An antibody substantially inhibits adhesion of a receptor to a counterreceptor when an excess of antibody reduces the quantity of receptor bound to counterreceptor by at least about 20%, 40%, 60% or 80%, and more usually greater than about 85% (as measured in an in vitro competitive binding assay).

"Fab antibodies" or "Fab fragments" refers to antibody fragments lacking all or part of an immunoglobulin constant region, and containing the Fab regions of the antibodies. Fab antibodies are prepared as described herein.

"Single chain antibodies" or "single chain Fv (scFv)" refers to an antibody fusion molecule of the two domains of the Fv fragment, $V_L$ and $V_H$. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., *Science* 242: 423-426, 1988; and Huston et al., *Proc. Natl. Acad. Sci. USA*, 85: 5879-5883, 1988). Such single chain antibodies are included by reference to the term "antibody" fragments can be prepared by recombinant techniques or enzymatic or chemical cleavage of intact antibodies.

"Human sequence antibody" includes antibodies having variable and constant regions (if present) derived from human germline immunoglobulin sequences. The human sequence antibodies of the invention can include amino acid residues not encoded by human germline immunoglobulin sequences (e.g., mutations introduced by random or site-specific mutagenesis in vitro or by somatic mutation in vivo). Such antibodies can be generated in non-human transgenic animals, e.g., as described in PCT Publication Nos. WO 01/14424 and WO 00/37504. However, the term "human sequence antibody", as used herein, is not intended to include antibodies in which CDR sequences derived from the germline of another mammalian species, such as a mouse, have been grafted onto human framework sequences (e.g., humanized antibodies).

Also, recombinant immunoglobulins may be produced. See, Cabilly, U.S. Pat. No. 4,816,567, incorporated herein by reference in its entirety and for all purposes; and Queen et al., *Proc. Nat'l Acad. Sci. USA* 86: 10029-10033, 1989.

"Monoclonal antibody" refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions (if present) derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

"Polyclonal antibody" refers to a preparation of more than 1 (two or more) different antibodies to a cell surface receptor or a ligand, e.g., β-hCG binding to LH/hCG receptor. Such a preparation includes antibodies binding to a range of β-hCG binding to LH/hCG receptor. Similarly antibodies to β-hCG can act as peptidomimetics that bind to LH/hCG receptor and thus inhibit β-hCG binding to LH/hCG receptor. These and other antibodies suitable for use in the present invention can be prepared according to methods that are well known in the art and/or are described in the references cited here. In preferred embodiments, anti-β-hCG antibodies used in the invention are "human antibodies"—e.g., antibodies isolated from a human—or they are "human sequence antibodies".

"Immune cell response" refers to the response of immune system cells to external or internal stimuli (e.g., antigen, cell surface receptors, β-hCG, LH/hCG receptor, cytokines, chemokines, and other cells) producing biochemical changes in the immune cells that result in immune cell migration, killing of target cells, phagocytosis, production of antibodies, other soluble effectors of the immune response, and the like.

"Immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, metastatic epithelial cancer, colorectal carcinoma, gastric carcinoma, oral carcinoma, pancreatic carcinoma, ovarian carcinoma, or renal cell carcinoma, invading pathogens, cells or tissues infected with pathogens, or, in cases of autoimmunity or pathological inflammation, normal human cells or tissues.

"T lymphocyte response" and "T lymphocyte activity" are used here interchangeably to refer to the component of immune response dependent on T lymphocytes (e.g., the proliferation and/or differentiation of T lymphocytes into helper, cytotoxic killer, or suppressor T lymphocytes, the provision of signals by helper T lymphocytes to B lymphocytes that cause or prevent antibody production, the killing of specific target cells by cytotoxic T lymphocytes, and the release of soluble factors such as cytokines that modulate the function of other immune cells).

Cancer Treatment

Blockade of β-hCG binding to LH/hCG receptor by antibody compositions, for example, an antibody which specifically binds to β-L2 loop of human chorionic gonadotropin (hCG), can enhance the memory or secondary immune response to cancerous cells in the patient. Antibodies to hCG can be combined with an immunogenic agent, such as cancerous cells, purified tumor antigens (including recombinant proteins, peptides, and carbohydrate molecules), cells, and cells transfected with genes encoding immune stimulating cytokines and cell surface antigens, or used alone, to stimulate immunity.

Antibodies to β-hCG are effective when following a vaccination protocol. Many experimental strategies for vaccination against tumors have been devised (see Rosenberg, *ASCO Educational Book* Spring: 60-62, 2000; Logothetis, *ASCO*

*Educational Book* Spring: 300-302, 2000; Khayat, *ASCO Educational Book* Spring: 414-428, 2000; Foon, *ASCO Educational Book* Spring: 730-738, 2000; see also Restifo et al., *Cancer: Principles and Practice of Oncology,* 61: 3023-3043, 1997. In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination. Dranoff et al., *Proc. Natl. Acad. Sci. U.S.A.,* 90: 3539-43, 1993.

Antibodies to β-hCG can boost GM-CSF-modified tumor cell vaccines improves efficacy of vaccines in a number of experimental tumor models such as mammary carcinoma (Hurwitz et al., 1998, supra), primary prostate cancer (Hurwitz et al., *Cancer Research,* 60: 2444-8, 2000) and melanoma (van Elsas et al., *J. Exp. Med.,* 190: 355-66, 1999). In these instances, non-immunogenic tumors, such as the B 16 melanoma, have been rendered susceptible to destruction by the immune system. The tumor cell vaccine can also be modified to express other immune activators such as IL2, and costimulatory molecules, among others.

"Antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

Chemotherapeutic agents can be used in combination with monoclonal antibodies to β-hCG, e.g., an antibody which specifically binds to β-L2 loop of hCG, in methods for treatment of neoplastic disease. An antibody-cytotoxin conjugate comprising antibodies to β-hCG can also be used to boost immunity induced through standard cancer treatments. In these instances, it can be possible to reduce the dose of chemotherapeutic reagent administered (Mokyr et al., *Cancer Research* 58: 5301-5304, 1998). The scientific rationale behind the combined use of antibodies to β-hCG and chemotherapy is that cell death, that is a consequence of the cytotoxic action of most chemotherapeutic compounds, should result in increased levels of tumor antigen in the antigen presentation pathway. Thus, antibodies to β-hCG can boost an immune response primed to chemotherapy release of tumor cells. Examples of chemotherapeutic agents combined with treatment with antibodies to β-hCG can include, but are not limited to, *Actinomycetes* or *Streptomyces* antibiotics, duocarmycin, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, duocarmycin, epoetin alpha, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol™), pilocarpine, prochloroperazine, rituximab, saproin, tamoxifen, taxol, topotecan hydrochloride, trastuzumab, vinblastine, vincristine and vinorelbine tartrate. For prostate cancer treatment, a preferred chemotherapeutic agent with which anti-β-hCG can be combined is paclitaxel (Taxol™). For melanoma cancer treatment, a preferred chemotherapeutic agent with which anti-β-hCG can be combined is dacarbazine (DTIC).

A "solid tumor" includes, but is not limited to, sarcoma, melanoma, carcinoma, or other solid tumor cancer.

"Sarcoma" refers to a tumor which is made up of a substance like the embryonic connective tissue and is generally composed of closely packed cells embedded in a fibrillar or homogeneous substance. Sarcomas include, but are not limited to, chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

"Melanoma" refers to a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

"Carcinoma" refers to a malignant new growth made up of epithelial cells tending to infiltrate the surrounding tissues and give rise to metastases. Exemplary carcinomas further include, for example, epithelial cancer, colorectal carcinoma, gastric carcinoma, oral carcinoma, pancreatic carcinoma, ovarian carcinoma, or renal cell carcinoma. Exemplary carcinomas further include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma viflosum.

"Leukemia" refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease—acute or chronic; (2) the type of cell involved; myeloid (myelogenous), lymphoid (lymphogenous), or monocytic; and (3) the increase or non-increase in the number of abnormal cells in the blood—leukemic or aleukemic (subleukemic). Leukemia includes, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

Additional cancers include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site.

Thus, an intact IgG antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk *J. Mol. Biol.* 196: 901-917, 1987; Chothia et al., *Nature* 342: 878-883, 1989.

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai and Lachmann, *Clin. Exp. Immunol.* 79: 315-321, 1990, Kostelny et al., *J. Immunol.* 148: 1547-1553, 1992. In addition, bispecific antibodies may be formed as "diabodies" (Holliger et al., *PNAS USA* 90: 6444-6448, 1993 or "Janusins" (Traunecker et al., *EMBO J.* 10: 3655-3659, 1991 and Traunecker et al., *Int J Cancer* 7:51-52, 1992). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Fab or scFV Phage Libraries

An approach for a phage display library to identify an antibody composition which binds to β-hCG, e.g., an antibody which specifically binds to β-L2 loop of hCG, or that specifically binds to a ligand or a cell surface receptor on a metastatic cell, for example, LH/hCG receptor, has been the use of Fab or single-chain Fv (scFv) phage-libraries. See, e.g., Huston et al., *Proc. Natl. Acad. Sci. U.S.A.,* 85: 5879-5883, 1988; Chaudhary et al., *Proc. Natl. Acad. Sci. U.S.A.,* 87: 1066-1070, 1990; Zhang et al., *J. Virol.* 78: 9233-9242, 2004. Various embodiments of Fab or scFv libraries displayed on bacteriophage coat proteins have been described. Refinements of phage display approaches are also known, for example as described in WO96/06213 and WO92/01047 (Medical Research Council et al.) and WO97/08320 (Morphosys), which are incorporated herein by reference. The display of Fab libraries is known, for instance as described in WO92/01047 (CAT/MRC) and WO91/17271 (Affymax).

Hybrid antibodies or hybrid antibody fragments that are cloned into a display vector can be selected against the appropriate antigen associated with a metastatic cell, e.g., a cell surface receptor or ligand to a cell surface receptor on a metastatic tumor cell, in order to identify variants that maintained good binding activity because the antibody or antibody fragment will be present on the surface of the phage or phagemid particle. See for example Barbas III et al., *Phage Display, A Laboratory Manual*, Cold Spring Harbor Laboratory Press, Cold Spring Harbor, N.Y., 2001, the contents of which are incorporated herein by reference. For example, in the case of Fab fragments, the light chain and heavy chain Fd products are under the control of a lac promoter, and each chain has a leader signal fused to it in order to be directed to the periplasmic space of the bacterial host. It is in this space that the antibody fragments will be able to properly assemble. The heavy chain fragments are expressed as a fusion with a phage coat protein domain which allows the assembled antibody fragment to be incorporated into the coat of a newly made phage or phagemid particle. Generation of new phagemid particles requires the addition of helper phage which contain all the necessary phage genes. Once a library of antibody fragments is presented on the phage or phagemid surface, a process termed panning follows. This is a method whereby) the antibodies displayed on the surface of phage or phagemid particles are bound to the desired antigen, ii) non-binders are washed away, iii) bound particles are eluted from the antigen, and iv) eluted particles are exposed to fresh bacterial hosts in order to amplify the enriched pool for an additional round of selection. Typically three or four rounds of panning are performed prior to screening antibody clones for specific binding. In this way phage/phagemid particles allow the linkage of binding phenotype (antibody) with the genotype (DNA) making the use of antibody display technology very successful. However, other vector formats could be used for this humanization process, such as cloning the antibody fragment library into a lytic phage vector (modified T7 or Lambda Zap systems) for selection and/or screening.

After selection of desired hybrid antibodies and/or hybrid antibody fragments, it is contemplated that they can be produced in large volume by any technique known to those skilled in the art, e.g., prokaryotic or eukaryotic cell expression and the like. For example, hybrid antibodies or fragments may be produced by using conventional techniques to construct an expression vector that encodes an antibody heavy chain in which the CDRs and, if necessary, a minimal portion of the variable region framework, that are required to retain original species antibody binding specificity (as engineered according to the techniques described herein) are derived from the originating species antibody and the remainder of the antibody is derived from a target species immunoglobulin which may be manipulated as described herein, thereby producing a vector for the expression of a hybrid antibody heavy chain.

In a detailed embodiment, a Fab or single-chain Fv (scFv) antibody library can be prepared from the peripheral blood lymphocytes of 5, 10, 15, or 20 or more patients with various cancer diseases. Completely human high-affinity Fab or scFv antibodies can then be selected by using synthetic sialyl Lewis$^x$ and Lewis$^x$ BSA conjugates. In one study, these human scFv antibodies were specific for sialyl Lewis$^x$ and Lewis$^x$, as demonstrated by ELISA, BIAcore, and flow cytometry binding to the cell surface of pancreatic adenocarcinoma cells. Nucleotide sequencing revealed that at least four unique scFv genes were obtained. The $K_d$ values ranged from 1.1 to $6.2 \times 10^{-7}$ M that were comparable to the affinities of mAbs derived from the secondary immune response. These antibodies could be valuable reagents for probing the structure and function of carbohydrate antigens and in the treatment of human tumor diseases. Mao et al., *Proc. Natl. Acad. Sci. U.S.A.* 96: 6953-6958, 1999.

In a further detailed embodiment, phage displayed combinatorial antibody libraries can be used to generate and select a wide variety of antibodies to an appropriate antigen associated with a metastatic cell, e.g., a cell surface receptor or a ligand to a cell surface receptor on a metastatic tumor cell. The phage coat proteins pVII and pIX can be used to display the heterodimeric structure of the antibody Fv region. Aspects of this technology have been extended to construct a large, human Fab or single-chain Fv (scFv) library of $4.5 \times 10^9$ members displayed on pIX of filamentous bacteriophage. Furthermore, the diversity, quality, and utility of the library were demonstrated by the selection of Fab or scFv clones against six different protein antigens. Notably, more than 90% of the selected clones showed positive binding for their respective antigens after as few as three rounds of panning. Analyzed Fabs or scFvs were also found to be of high affinity. For example, kinetic analysis (BIAcore) revealed that Fabs or scFvs against staphylococcal enterotoxin B and cholera toxin B subunit had a nanomolar and subnanomolar dissociation constant, respectively, affording affinities comparable to, or exceeding that, of mAbs obtained from immunization. High specificity was also attained, not only between very distinct proteins, but also in the case of more closely related proteins, e.g., *Ricinus communis* ("ricin") agglutinins ($RCA_{60}$ and $RCA_{120}$), despite >80% sequence homology between the two. The results suggested that the performance of pIX-display libraries can potentially exceed that of the pill-display format and make it ideally suited for panning a wide variety of target antigens. Gao et al., *Proc. Natl. Acad. Sci. U.S.A.* 99: 12612-12616, 2001.

Specific binding between an antibody or other binding agent and an antigen means a binding affinity of at least $10^{-6}$ M. Preferred binding agents bind with affinities of at least about $10^{-7}$ M, and preferably $10^{-8}$ M to $10^{-9}$ M, $10^{-10}$ M, $10^{-11}$ M, or $10^{-12}$ M. The term epitope means an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

"Epitope" refers to that portion of any molecule capable of being recognized by and bound by an antibody or T-cell receptor at one or more of the antibody's or T cell receptor's antigen binding region. Epitopes usually consist of chemically active surface groupings of molecules such as amino acids or sugar side chains and have specific three dimensional structural characteristics as well as specific charge characteristics. By "inhibiting and/or neutralizing epitope" is intended an epitope, which, when bound by an antibody, results in loss of biological activity of the molecule or organism containing the epitope, in vivo, in vitro or in situ, more preferably in vivo, including binding of HCG to an LH/hCG receptor. An antibody is said to specifically bind an antigen when the dissociation constant is less than 1 µM, preferably less than 100 nM and most preferably less than 10 nM. Conformational and nonconformational epitopes are distinguished in that the binding to the former but not the latter is lost in the presence of denaturing solvents.

Epitopes recognized by antibodies, and fragments and regions thereof, of the present invention can include 5 or more amino acids comprising at least one amino acid of each or both of the following amino acid sequences of β-hCG, which provide a topographical or three dimensional epitope of β-hCG which is recognized by, and/or binds with anti-β-hCG activity, an antibody, and fragments, and variable regions thereof, of the present invention: Screening Methods for determining β-hCG neutralizing and/or inhibiting activity are also provided in the present invention. In the context of the present invention, anti-β-hCG neutralizing activity or β-hCG inhibiting activity refers to the ability of a β-hCG neutralizing compound to block at least one biological activity of β-hCG, such as preventing β-hCG from binding to a LH/hCG receptor, blocking production of β-hCG by intracellular processing, such as transcription, translation or post-translational modification, expression on the cell surface, secretion or assembly of the bioactive β-hCG. Additionally, β-hCG neutralizing compounds can act by inducing regulation of metabolic pathways such as those involving the up or down regulation of β-hCG production. Alternatively β-hCG neutralizing compounds can modulate cellular sensitivity to β-hCG by decreasing such sensitivity. β-hCG neutralizing compounds can be selected from the group consisting of antibodies, or fragments or portions thereof, peptides, peptido mimetic compounds or organo mimetic compounds that neutralizes β-hCG activity in vitro, in situ or in vivo is considered a β-hCG neutralizing compound if used according to the present invention. Screening methods which can be used to determine β-hCG neutralizing activity of a β-hCG neutralizing compound can include in vitro or in vivo assays. Such in vitro assays can include an assay for (i) inhibition of proliferation in vitro of BXPC-3 pancreatic carcinoma cells; and (ii) no inhibition of proliferation in vitro of MCF-7 breast carcinoma cells or HeLa cells at an antibody concentration about 4 nM or greater; (ii) inhibition of β-hCG binding to LH/hCG receptor; or (iii) inhibition of cell migration in a cell migration assay. Alternatively or additionally, in vivo testing of β-hCG neutralizing activity of β-hCG neutralizing compounds can be tested using an in vitro assay for inhibition of proliferation in vitro of BXPC-3 pancreatic carcinoma cells at an antibody concentration about 4 nM or greater, as described herein.

"Neutralizing" refers to an antibody that inhibits β-hCG activity by preventing the binding of human β-hCG to its specific receptor, LH/hCG receptor, or by inhibiting the signaling of β-hCG through its receptor, should binding occur. A monoclonal antibody is neutralizing if it is 90% effective, preferably 95% effective and most preferably 100% effective in inhibiting β-hCG activity, for example, as measured by in vitro cell assay, such as (i) inhibition of proliferation in vitro of BXPC-3 pancreatic carcinoma cells; and (ii) no inhibition of proliferation in vitro of MCF-7 breast carcinoma cells or HeLa cells.

"Agent" is used herein to denote a chemical compound, a mixture of chemical compounds, a biological macromolecule, or an extract made from biological materials.

"Altered antibody" refers to a protein encoded by an altered immunoglobulin coding region, which may be obtained by expression in a selected host cell. Such altered antibodies are engineered antibodies (e.g., chimeric or humanized antibodies) or antibody fragments lacking all or part of an immunoglobulin constant region, e.g., Fv, Fab, or F(ab)$_2$ and the like.

"Altered immunoglobulin coding region" refers to a nucleic acid sequence encoding altered antibody of the invention. When the altered antibody is a CDR-grafted or humanized antibody, the sequences that encode the complementarity determining regions (CDRs) from a non-human immunoglobulin are inserted into a first immunoglobulin partner comprising human variable framework sequences. Optionally, the first immunoglobulin partner is operatively linked to a second immunoglobulin partner.

"High affinity" refers to an antibody having a binding affinity characterized by a $K_d$ equal to or less than $3.5 \times 10^{-11}$ M for human β-hCG as determined by surface plasmon resonance.

By "binding specificity for human β-CG" is meant a high affinity for human chorionic gonadotropin. Monoclonal antibodies have a high binding specificity for β-hCG and do not bind with high affinity to other associated hCG subunits or receptors. Monoclonal antibodies mAb 2B2.6F5 and 2B3.3E8 have a high binding specificity for β-hCG, and do not bind to α-hCG or to LH/hCG receptor.

The terms Fv, Fc, Fd, Fab, or F(ab)$_2$ are used with their standard meanings (see, e.g., Harlow et al., Antibodies A Laboratory Manual, Cold Spring Harbor Laboratory, (1988)).

"Engineered antibody" describes a type of altered antibody, i.e., a full-length synthetic antibody (e.g., a chimeric or humanized antibody as opposed to an antibody fragment) in which a portion of the light and/or heavy chain variable domains of a selected acceptor antibody are replaced by analogous parts from one or more donor antibodies which have specificity for the selected epitope. For example, such molecules may include antibodies characterized by a humanized heavy chain associated with an unmodified light chain (or chimeric light chain), or vice versa. Engineered antibodies may also be characterized by alteration of the nucleic acid sequences encoding the acceptor antibody light and/or heavy variable domain framework regions in order to retain donor antibody binding specificity. These antibodies can comprise replacement of one or more CDRs (preferably all) from the acceptor antibody with CDRs from a donor antibody described herein.

A "chimeric antibody" refers to a type of engineered antibody which contains naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity. See, e.g., Queen et al., *Proc. Natl. Acad Sci USA*, 86: 10029-10032, 1989, Hodgson et al., *Bio/Technology*, 2: 421, 1991.

"Donor antibody" refers to an antibody (monoclonal, or recombinant) which contributes the nucleic acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

"Acceptor antibody" refers to an antibody (monoclonal, or recombinant) heterologous to the donor antibody, which contributes all (or any portion, but preferably all) of the nucleic acid sequences encoding its heavy and/or light chain framework regions and/or its heavy and/or light chain constant regions to the first immunoglobulin partner. Preferably a human antibody is the acceptor antibody.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate).

CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

By "sharing the antigen binding specificity or neutralizing ability" is meant, for example, that although mAb 2B2.6F5 or 2B3.3E8 can be characterized by a certain level of antigen affinity, a CDR encoded by a nucleic acid sequence of mAb 2B2.6F5 or 2B3.3E8 in an appropriate structural environment may have a lower, or higher affinity. It is expected that CDRs of mAb 2B2.6F5 or 2B3.3E8 in such environments will nevertheless recognize the same epitope(s) as the original monoclonal antibodies. Exemplary heavy chain CDRs include SEQ ID NO:1; SEQ ID NO:3; and SEQ ID NO:5. See, for example, FIG. 11.

A "functional fragment" is a partial heavy or light chain variable sequence (e.g., minor deletions at the amino or carboxy terminus of the immunoglobulin variable region) which retains the same antigen binding specificity and/or neutralizing ability as the antibody from which the fragment was derived.

An "analog" is an amino acid sequence modified by at least one amino acid, wherein said modification can be chemical or a substitution or a rearrangement of a few amino acids (i.e., no more than 10), which modification permits the amino acid sequence to retain the biological characteristics, e.g., antigen specificity and high affinity, of the unmodified sequence. For example, (silent) mutations can be constructed, via substitutions, when certain endonuclease restriction sites are created within or surrounding CDR-encoding regions.

Analogs may also arise as allelic variations. An "allelic variation or modification" is an alteration in the nucleic acid sequence encoding the amino acid or peptide sequences of the invention. Such variations or modifications may be due to degeneracy in the genetic code or may be deliberately engineered to provide desired characteristics. These variations or modifications may or may not result in alterations in any encoded amino acid sequence.

"Carrier agents" or "effector agents" refers to non-protein carrier molecules to which the altered antibodies, and/or natural or synthetic light or heavy chains of the donor antibody or other fragments of the donor antibody may be associated by conventional means. Such non-protein carriers can include conventional carriers used in the diagnostic field, e.g., polystyrene or other plastic beads, polysaccharides, e.g., as used in the BIAcore® [Pharmacia] system, or other non-protein substances useful in the medical field and safe for administration to humans and animals. Other effector agents may include a macrocycle, for chelating a heavy metal atom, or radioisotopes. Such effector agents may also be useful to increase the half-life of the altered antibodies, e.g., polyethylene glycol.

Components of an immune response can be detected in vitro by various methods that are well known to those of ordinary skill in the art. For example, (1) cytotoxic T lymphocytes can be incubated with radioactively labeled target cells and the lysis of these target cells detected by the release of radioactivity; (2) helper T lymphocytes can be incubated with antigens and antigen presenting cells and the synthesis and secretion of cytokines measured by standard methods (Windhagen et al., *Immunity,* 2: 373-80, 1995); (3) antigen presenting cells can be incubated with whole protein antigen and the presentation of that antigen on MHC detected by either T lymphocyte activation assays or biophysical methods (Harding et al., *Proc. Natl. Acad. Sci.,* 86: 4230-4, 1989); (4) mast cells can be incubated with reagents that cross-link their Fc-epsilon receptors and histamine release measured by enzyme immunoassay (Siraganian et al., *TIPS,* 4: 432-437, 1983).

Similarly, products of an immune response in either a model organism (e.g., mouse) or a human patient can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., *Blood,* 72: 1310-5, 1988); (3) the proliferation of peripheral blood mononuclear cells in response to mitogens or mixed lymphocyte reaction can be measured using $^3$H-thymidine; (4) the phagocytic capacity of granulocytes, macrophages, and other phagocytes in PBMCs can be measured by placing PMBCs in wells together with labeled particles (Peters et al., *Blood,* 72: 1310-5, 1988); and (5) the differentiation of immune system cells can be measured by labeling PBMCs with antibodies to CD molecules such as CD4 and CD8 and measuring the fraction of the PBMCs expressing these markers.

For convenience, immune responses are often described in the present invention as being either "primary" or "secondary" immune responses. A primary immune response, which is also described as a "protective" immune response, refers to an immune response produced in an individual as a result of some initial exposure (e.g. the initial "immunization") to a particular antigen, e.g., cell surface receptor, ligand, β-hCG, or LH/hCG receptor. Such an immunization can occur, for example, as the result of some natural exposure to the antigen (for example, from initial infection by some pathogen that exhibits or presents the antigen) or from antigen presented by cancer cells of some tumor in the individual (for example, a metastatic epithelial cancer, colorectal carcinoma, gastric carcinoma, oral carcinoma, pancreatic carcinoma, ovarian carcinoma, or renal cell carcinoma). Alternatively, the immunization can occur as a result of vaccinating the individual with a vaccine containing the antigen. For example, the vaccine can be a cancer vaccine comprising one or more antigens from a cancer cell e.g., cells from a metastatic epithelial cancer, colorectal carcinoma, gastric carcinoma, oral carcinoma, pancreatic carcinoma, ovarian carcinoma, or renal cell carcinoma.

A primary immune response can become weakened or attenuated over time and can even disappear or at least become so attenuated that it cannot be detected. Accordingly, the present invention also relates to a "secondary" immune response, which is also described here as a "memory immune response." The term secondary immune response refers to an immune response elicited in an individual after a primary immune response has already been produced. Thus, a secondary or immune response can be elicited, e.g., to enhance an existing immune response that has become weakened or attenuated, or to recreate a previous immune response that has either disappeared or can no longer be detected. An agent that can be administrated to elicit a secondary immune response is after referred to as a "booster" since the agent can be said to "boost" the primary immune response.

As an example, and not by way of limitation, a secondary immune response can be elicited by re-introducing to the individual an antigen that elicited the primary immune response (for example, by re-administrating a vaccine). However, a secondary immune response to an antigen can also be elicited by administrating other agents that can not contain the actual antigen. For example, the present invention provides methods for potentiating a secondary immune response by administrating an antibody to β-hCG to an individual. In such methods the actual antigen need not necessarily be administered with the antibody to β-hCG and the composition containing the antibody need not necessarily contain the antigen. The secondary or memory immune response can be either a humoral (antibody) response or a cellular response. A secondary or memory humoral response occurs upon stimulation of memory B cells that were generated at the first presentation of the antigen. Delayed type hypersensitivity (DTH) reactions are a type of cellular secondary or memory immune response that are mediated by $CD4^+$ cells. A first exposure to an antigen primes the immune system and additional exposure(s) results in a DTH.

"Immunologically cross-reactive" or "immunologically reactive" refers to an antigen which is specifically reactive with an antibody which was generated using the same ("immunologically reactive") or different ("immunologically cross-reactive") antigen. Generally, the antigen is β-hCG or LH/hCG receptor, or subsequence thereof.

"Immunologically reactive conditions" refers to conditions which allow an antibody, generated to a particular epitope of an antigen, to bind to that epitope to a detectably greater degree than the antibody binds to substantially all other epitopes, generally at least two times above background binding, preferably at least five times above background. Immunologically reactive conditions are dependent upon the format of the antibody binding reaction and typically are those utilized in immunoassay protocols. See, Harlow and Lane, *Antibodies, A Laboratory Manual*, Cold Spring Harbor Publications, New York, 1988 for a description of immunoassay formats and conditions.

"Cell surface receptor" refers to molecules and complexes of molecules capable of receiving a signal and the transmission of such a signal across the plasma membrane of a cell. An example of a "cell surface receptor" of the present invention is an LH/hCG receptor on a metastatic cell.

"Nonspecific T cell activation" refers to the stimulation of T cells independent of their antigenic specificity.

"Effector cell" refers to an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Effector cells express specific Fc receptors and carry out specific immune functions. An effector cell can induce antibody-dependent cell-mediated cytotoxicity (ADCC), e.g., a neutrophil capable of inducing ADCC. For example, monocytes, macrophages, neutrophils, eosinophils, and lymphocytes which express FcαR are involved in specific killing of target cells and presenting antigens to other components of the immune system, or binding to cells that present antigens. An effector cell can also phagocytose a target antigen, target cell, metastatic cancer cell, or microorganism.

"Target cell" refers to any undesirable cell in a subject (e.g., a human or animal) that can be targeted by the Ab or Ab composition of the invention. The target cell can be a cell expressing or overexpressing human LH/hCG receptor. Cells expressing human LH/hCG receptor can include tumor cells, e.g. a metastatic epithelial cancer, colorectal carcinoma, gastric carcinoma, oral carcinoma, pancreatic carcinoma, ovarian carcinoma, or renal cell carcinoma.

Targets of interest for antibody compositions metastatic cancer cells, e.g., metastatic epithelial cancer cells, include, but are not limited to, cell surface receptors, growth factor receptors, β-hCG, LH/hCG receptor, (See, for example, Burtrum D., et al, *Cancer Res.*, 63: 8912-8921, 2003; Lu et al., *J. Biol. Chem.* 279: 2856-2865, 2004; Miyamoto et al., *Clin. Cancer Res.* 11: 3494-3502, 2005; Goya et al., *Cancer Research* 64: 6252-6258, 2004) antibodies, including anti-idiotypic antibodies and autoantibodies present in cancer, such as metastatic cancer, metastatic epithelial cancer, colorectal carcinoma, gastric carcinoma, oral carcinoma, pancreatic carcinoma, ovarian carcinoma, or renal cell carcinoma. Other targets are adhesion proteins such as integrins, selectins, and immunoglobulin superfamily members. Springer, *Nature*, 346: 425-433, 1990; Osborn, *Cell*, 62: 3, 1990; Hynes, *Cell*, 69: 11, 1992. Other targets of interest are growth factor receptors (e.g., FGFR, PDGFR, EGF, her/neu, NGFR, and VEGF) and their ligands. Other targets are G-protein receptors and include substance K receptor, the angiotensin receptor, the α- and β-adrenergic receptors, the serotonin receptors, and PAF receptor. See, e.g., Gilman, *Ann. Rev. Biochem.* 56: 625-649, 1987. Other targets include ion channels (e.g., calcium, sodium, potassium channels, channel proteins that mediate multidrug resistance), muscarinic receptors, acetylcholine receptors, GABA receptors, glutamate receptors, and dopamine receptors (see Harpold, U.S. Pat. No. 5,401,629 and U.S. Pat. No. 5,436,128). Other targets are cytokines, such as interleukins IL-1 through IL-13, tumor necrosis factors α- and β, interferons α-, β- and γ, tumor growth factor Beta (TGF-β), colony stimulating factor (CSF) and granulocyte monocyte colony stimulating factor (GM-CSF). See Aggrawal et al., eds., *Human Cytokines Handbook for Basic & Clinical Research*, Blackwell Scientific, Boston, Mass., 1991. Other targets are hormones, enzymes, and intracellular and intercellular messengers, such as adenyl cyclase, guanyl cyclase, and phospholipase C. Drugs are also targets of interest. Target molecules can be human, mammalian or bacterial. Other targets are antigens, such as proteins, glycoproteins and carbohydrates from microbial pathogens, both viral and bacterial, and tumors. Still other targets are described in U.S. Pat. No. 4,366,241, incorporated herein by reference in its entirety and for all purposes. Some agents screened by the target merely bind to a target. Other agents agonize or antagonize the target.

Recombinant Expression of Anti-Human-β-CG Antibodies

Recombinant human antibodies that bind to β-hCG, e.g., an antibody which specifically binds to β-L2 loop of hCG, inhibit β-hCG binding to LH/hCG receptor, are provided according to the present invention using known techniques based on the teaching provided herein. See, e.g., Ausubel et al., eds. *Current Protocols in Molecular Biology*, Wiley Interscience, N.Y. (1987, 1992, 1993); and Sambrook et al. *Molecular Cloning: A Laboratory Manual*, Cold Spring Harbor Laboratory Press (1989), the entire contents of which are incorporated herein by reference.

The DNA encoding an anti-hCG antibody of the present invention can be genomic DNA or cDNA which encodes at least one of the heavy chain constant region ($C_H$), the heavy chain variable region ($V_H$), the light chain variable region ($V_L$) and the light chain constant regions ($C_L$). A convenient alternative to the use of chromosomal gene fragments as the source of DNA encoding the murine V region antigen-binding segment is the use of cDNA for the construction of chimeric immunoglobulin genes, e.g., as reported by Liu et al., *Proc. Natl. Acad. Sci., USA* 84:3439 (1987) and *J. Immunology* 139: 3521 (1987), which references are hereby entirely incorporated herein by reference. The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

Such techniques for synthesizing such oligonucleotides are well known and disclosed by, for example, Wu, et al., *Prog. Nucl. Acid. Res. Molec. Biol.* 21:101-141 (1978)), and Ausubel et al., eds. *Current Protocols in Molecular Biology*, Wiley Interscience (1987, 1993), the entire contents of which are herein incorporated by reference.

Because the genetic code is degenerate, more than one codon can be used to encode a particular amino acid (Watson, et al., infra). Using the genetic code, One or more different oligonucleotides can be identified, each of which would be capable of encoding the amino acid. The probability that a particular oligonucleotide will, in fact, constitute the actual anti-β-hCG antibody encoding sequence can be estimated by considering abnormal base pairing relationships and the frequency with which a particular codon is actually used (to encode a particular amino acid) in eukaryotic or prokaryotic cells expressing an anti-β-hCG antibody or fragment. Such "codon usage rules" are disclosed by Lathe, et al., *J. Molec. Biol.* 183:1-12 (1985). Using the "codon usage rules" of Lathe, a single oligonucleotide, or a set of oligonucleotides, that contains a theoretical "most probable" nucleotide sequence capable of encoding anti-β-hCG variable or constant region sequences is identified.

Although occasionally an amino acid sequence can be encoded by only a single oligonucleotide, frequently the amino acid sequence can be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the protein.

The oligonucleotide, or set of oligonucleotides, containing the theoretical "most probable" sequence capable of encoding an anti-β-hCG antibody or fragment including a variable or constant region is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the variable or constant region anti-β-hCG gene (Sambrook et al., infra).

A suitable oligonucleotide, or set of oligonucleotides, which is capable of encoding a fragment of the variable or constant anti-β-hCG region (or which is complementary to such an oligonucleotide, or set of oligonucleotides) is identified (using the above-described procedure), synthesized, and hybridized by means well known in the art, against a DNA or, more preferably, a cDNA preparation derived from cells which are capable of expressing anti-β-hCG antibodies or variable or constant regions thereof. Single stranded oligonucleotide molecules complementary to the "most probable" variable or constant anti-β-hCG region peptide coding sequences can be synthesized using procedures which are well known to those of ordinary skill in the art (Belagaje, et al., *J. Biol. Chem.* 254: 5765-5780 (1979); Maniatis, et al., In: Molecular Mechanisms in the Control of Gene Expression, Nierlich, et al., Eds., Acad. Press, NY (1976); Wu, et al., *Prog. Nucl. Acid Res. Molec. Biol.* 21: 101-141 (1978); Khorana, *Science* 203: 614-625 (1979)). Additionally, DNA synthesis can be achieved through the use of automated synthesizers.

Techniques of nucleic acid hybridization are disclosed by Sambrook et al. (infra), and by Hayrnes, et al. (In: Nucleic Acid Hybridization, A Practical Approach, IRL Press, Washington, D.C. (1985)), which references are herein incorporated by reference. Techniques such as, or similar to, those described above have successfully enabled the cloning of genes for human aldehyde dehydrogenases (Hsu, et al., *Proc. Natl. Acad. Sci. USA* 82: 3771-3775 (1985)), fibronectin (Suzuki, et al., *Bur. Mol. Biol. Organ. J.* 4: 2519-2524 (1985)), the human estrogen receptor gene (Walter, et al., *Proc. Natl. Acad. Sci. USA* 82: 7889-7893 (1985)), tissue-type plasminogen activator (Pennica, et al., *Nature* 301: 214-221 (1983)) and human term placental alkaline phosphatase complementary DNA (Keun, et al., *Proc. Natl. Acad. Sci. USA* 82: 8715-8719 (1985)).

In an alternative way of cloning a polynucleotide encoding an anti-β-hCG antibody variable or constant region, a library of expression vectors is prepared by cloning DNA or, more preferably, cDNA (from a cell capable of expressing an anti-β-hCG antibody or variable or constant region) into an expression vector. The library is then screened for members capable of expressing a protein which competitively inhibits the binding of an anti-β-hCG antibody, such as mAb 2B2.6F5 or 2B3.3E8, to LH/hCG receptor and which has a nucleotide sequence that is capable of encoding polypeptides that have the same amino acid sequence as anti-β-hCG antibodies or fragments thereof. In this embodiment, DNA, or more preferably cDNA, is extracted and purified from a cell which is capable of expressing an anti-β-hCG antibody or fragment. The purified cDNA is fragmentized (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment such as in a lambda phage library, expression in prokaryotic cell (e.g., bacteria) or eukaryotic cells, (e.g., mammalian, yeast, insect or, fungus). See, e.g., Ausubel, infra, Harlow, infra, Colligan, infra; Nyyssonen et al. *Bio/Technology* 11: 591-595 (Can 1993); Marks et al., *Bio/Technology* 11: 1145-1149, 1993. Once nucleic acid encoding such variable or constant anti-β-hCG regions is isolated, the nucleic acid can be appropriately expressed in a host cell, along with other constant or variable heavy or light chain encoding nucleic acid, in order to provide recombinant MAbs that bind β-hCG with inhibitory activity. Such antibodies preferably include a murine or human anti-β-hCG variable region which contains a framework residue having complimentarity determining residues which are responsible for antigen binding. In a preferred embodiment, an anti-β-hCG variable light or heavy chain encoded by a nucleic acid as described above binds an epitope of at least 5 amino acids of, SEQ ID NO:2, SEQ ID NO:4, or SEQ ID NO:6.

Human genes which encode the constant (C) regions of the murine and chimeric antibodies, fragments and regions of the present invention can be derived from a human fetal liver library, by known methods. Human C regions genes can be derived from any human cell including those which express and produce human immunoglobulins. The human $C_H$ region can be derived from any of the known classes or isotypes of human H chains, including γ, μ, α, δ, or ϵ, and subtypes thereof, such as G1, G2, G3 and G4. Since the H chain isotype is responsible for the various effector functions of an antibody, the choice of $C_H$ region will be guided by the desired effector functions, such as complement fixation, or activity in antibody-dependent cellular cytotoxicity (ADCC). Preferably, the $C_H$ region is derived from gamma 1 (IgG1), gamma 3 (IgG3), gamma 4 (IgG4), or mu (IgM).

Human Antibodies and Humanization of Antibodies

Human antibodies avoid certain of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, it has been postulated that one can develop humanized antibodies or generate fully human antibodies through the introduction of human antibody function into a rodent so that the rodent would produce antibodies having fully human sequences.

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy could provide an ideal source for production of fully human monoclonal antibodies (Mabs) an important milestone towards fulfilling the promise of antibody therapy in human disease. Fully human antibodies are expected to minimize the immunogenic and allergic responses intrinsic to mouse or mouse-derivatized Mabs and thus to increase the efficacy and safety of the administered antibodies. The use of fully human antibodies can be expected to provide a substantial advantage in the treatment of chronic and recurring human diseases, such as inflammation, autoimmunity, and cancer, which require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Mabs with the desired specificity could be readily produced and selected.

Such approach is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, filed Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, and Ser. No. 08/759,620, filed Dec. 3, 1996. See also Mendez et al., *Nature Genetics* 15: 146-156, 1997 and Green and Jakobovits, *J. Exp. Med.* 188: 483-495, 1998. See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, and WO 98/24893, published Jun. 11, 1998. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, and 5,814,318 each to Lonberg and Kay, U.S. Pat. No. 5,591,669 to Krimpenfort and Berns, U.S. Pat. Nos. 5,612,205, 5,721,367, 5,789,215 to Berns et al., and U.S. Pat. No. 5,643,763 to Choi and Dunn, and GenPharm International U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884, the disclosures of which are hereby incorporated by reference in their entirety. See further Taylor et al., 1992, Chen et al., 1993, Tuaillon et al., 1993, Choi et al., 1993, Lonberg et al., 1994, Taylor et al., 1994, and Tuaillon et al., 1995, Fishwild et al., 1996, the disclosures of which are hereby incorporated by reference in their entirety.

A transgenic mouse possessing an Ig locus has been produced through use of the minilocus approach. An advantage of the minilocus approach is the rapidity with which constructs including portions of the Ig locus can be generated and introduced into animals. Commensurately, however, a significant disadvantage of the minilocus approach is that, in theory, insufficient diversity is introduced through the inclusion of small numbers of V, D, and J genes. Indeed, the published work appears to support this concern. B-cell development and antibody production of animals produced through use of the minilocus approach appear stunted. Therefore, research surrounding the present invention has consistently been directed towards the introduction of large portions of the Ig locus in order to achieve greater diversity and in an effort to reconstitute the immune repertoire of the animals.

Human anti-mouse antibody (HAMA) responses have led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against β-hCG in order to vitiate concerns and/or effects of HAMA or HACA response.

Humanization and Display Technologies

As was discussed above in connection with human antibody generation, there are advantages to producing antibodies with reduced immunogenicity. To a degree, this can be accomplished in connection with techniques of humanization and display techniques using appropriate libraries. It will be appreciated that murine antibodies or antibodies from other species can be humanized or primatized using techniques well known in the art. See e.g., Winter and Harris, *Immunol Today* 14: 43-46, 1993 and Wright et al., *Crit. Reviews in Immunol.* 12:125-168, 1992. The antibody of interest may be engineered by recombinant DNA techniques to substitute the $C_H1$, $C_H2$, $C_H3$, hinge domains, and/or the framework domain with the corresponding human sequence (see WO 92/02190 and U.S. Pat. Nos. 5,530,101, 5,585,089, 5,693,761, 5,693,792, 5,714,350, and 5,777,085). Also, the use of Ig cDNA for construction of chimeric immunoglobulin genes is known in the art (Liu et al., *PNAS USA* 84: 3439, 1987 and *J. Immunol.* 139: 3521, 1987). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Rabat et al. (1991) Sequences of Proteins of Immunological Interest, NIH publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG2, IgG3 and IgG4. Particularly preferred isotypes for antibodies of the invention are IgG2 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

In one approach, consensus sequences encoding the heavy and light chain J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, cosmids, YACs, EBV derived episomes, and the like. A convenient vector is one that encodes a functionally complete human $C_H$ or $C_L$ immunoglobulin sequence, with appropriate restriction sites engineered so that any $V_H$ or $V_L$ sequence can be easily inserted and expressed. In such vectors, splicing usually occurs between the splice donor site in the inserted J region and the splice acceptor site preceding the human C region, and also at the splice regions that occur within the human $C_H$ exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al., *Mol. Cell. Bio.* 3: 280, 1983), Rous sarcoma virus LTR (Gorman et al., *P.N.A.S.* 79: 6777, 1982), and moloney murine leukemia virus LTR (Grosschedl et al., *Cell* 41: 885, 1985); native 1 g promoters, etc.

Further, human antibodies or antibodies from other species can be generated through display-type technologies, including, without limitation, phage display, retroviral display, ribosomal display, and other techniques, using techniques well known in the art and the resulting molecules can be subjected to additional maturation, such as affinity maturation, as such techniques are well known in the art. Wright and Harris, supra, Hanes and Plucthau, *PNAS USA* 94: 4937-4942, 1997 (ribosomal display), Parmley and Smith, *Gene* 73: 305-318, 1988 (phage display), Scott, *TIBS* 17: 241-245, 1992, Cwirla et al., *PNAS USA* 87: 6378-6382, 1990, Russel et al., *Nucl. Acids Research* 21: 1081-1085, 1993, Hoganboom et al., *Immunol. Reviews* 130: 43-68, 1992, Chiswell and McCafferty, *TIBTECH* 10: 80-84, 1992, and U.S. Pat. No. 5,733, 743. If display technologies are utilized to produce antibodies that are not human, such antibodies can be humanized as described above.

Using these techniques, antibodies can be generated to β-hCG expressing cells, β-hCG, hCG or forms of hCG, epitopes or peptides thereof, and expression libraries thereto (see e.g. U.S. Pat. No. 5,703,057) which can thereafter be screened as described above for the activities described above.

Design and Generation of Other Therapeutics

In accordance with the present invention and based on the activity of the antibodies that are produced and characterized herein, such as antibodies to β-hCG, or an antibody which specifically binds to β-L2 loop of hCG, the design of other therapeutic modalities including other antibodies, other antagonists, or chemical moieties other than antibodies is facilitated. Such modalities include, without limitation, antibodies having similar binding activity or functionality, advanced antibody therapeutics, such as bispecific antibodies, immunotoxins, and radiolabeled therapeutics, generation of peptide therapeutics, gene therapies, particularly intrabodies, antisense therapeutics, and small molecules. Furthermore, as discussed above, the effector function of the antibodies of the invention may be changed by isotype switching to an IgG1, IgG2, IgG3, IgG4, IgD, IgA, IgE, or IgM for various therapeutic uses.

In connection with the generation of advanced antibody therapeutics, where complement fixation is a desirable attribute, it may be possible to sidestep the dependence on complement for cell killing through the use of bispecifics, immunotoxins, or radiolabels, for example.

In connection with bispecific antibodies, bispecific antibodies can be generated that comprise (i) two antibodies one with a specificity to β-hCG and another to a second molecule that are conjugated together, (ii) a single antibody that has one chain specific to β-hCG and a second chain specific to a second molecule, or (iii) a single chain antibody that has specificity to β-hCG and the other molecule. Such bispecific antibodies can be generated using techniques that are well known for example, in connection with (i) and (ii) see e.g., Fanger et al., *Immunol Methods* 4: 72-81, 1994 and Wright and Harris, supra. and in connection with (iii) see e.g., Traunecker et al., *Int. J. Cancer* 7: 51-52, 1992.

In addition, "Kappabodies" (Ill et al., *Protein Eng* 10: 949-57, 1997), "Minibodies" (Martin et al., *EMBO J.* 13: 5303-9, 1994), "Diabodies" (Holliger et al., *PNAS USA* 90: 6444-6448, 1993), or "Janusins" (Traunecker et al., *EMBO J* 10: 3655-3659, 1991) and Traunecker et al., *Int J Cancer* 7:51-52, 1992) may also be prepared.

In connection with immunotoxins, antibodies can be modified to act as immunotoxins utilizing techniques that are well known in the art. See e.g., Vitetta, *Immunol Today* 14: 252, 1993. See also U.S. Pat. No. 5,194,594. In connection with the preparation of radiolabeled antibodies, such modified antibodies can also be readily prepared utilizing techniques that are well known in the art. See e.g., Junghans et al., Cancer Chemotherapy and Biotherapy 655-686 (2d edition, Chafier and Longo, eds., Lippincott Raven, 1996). See also U.S. Pat. Nos. 4,681,581, 4,735,210, 5,101,827, 5,102,990 (RE 35,500), U.S. Pat. Nos. 5,648,471, and 5,697,902. Each of immunotoxins and radiolabeled molecules would be likely to kill cells expressing β-hCG, and particularly those cells in which the antibodies of the invention are effective.

In connection with the generation of therapeutic peptides, through the utilization of structural information related to β-hCG and antibodies thereto, such as the antibodies of the invention (as discussed below in connection with small molecules) or screening of peptide libraries, therapeutic peptides can be generated that are directed against β-hCG. Design and screening of peptide therapeutics is discussed in connection with Houghten et al., *Biotechniques* 13: 412-421, 1992, Houghten *PNAS USA* 82: 5131-5135, 1985, Pinalla et al., *Biotechniques* 13: 901-905, 1992, Blake and Litzi-Davis, *BioConjugate Chem.* 3: 510-513, 1992. Immunotoxins and radiolabeled molecules can also be prepared, and in a similar manner, in connection with peptidic moieties as discussed above in connection with antibodies.

Important information related to the binding of an antibody to an antigen can be gleaned through phage display experimentation. Such experiments are generally accomplished through panning a phage library expressing random peptides for binding with the antibodies of the invention to determine if peptides can be isolated that bind. If successful, certain epitope information can be gleaned from the peptides that bind.

In general, phage libraries expressing random peptides can be purchased from New England Biolabs (7-mer and 12-mer libraries, Ph.D.-7 Peptide 7-mer Library Kit and Ph.D.-12 Peptide 12-mer Library Kit, respectively) based on a bacteriophage M13 system. The 7-mer library represents a diversity of approximately $2.0 \times 10^9$ independent clones, which represents most, if not all, of the $20^7 = 1.28 \times 10^9$ possible 7-mer sequences. The 12-mer library contains approximately $1.9 \times 10^9$ independent clones and represents only a very small sampling of the potential sequence space of $20^{12} = 4.1 \times 10^{15}$ 12-mer sequences. Each of 7-mer and 12-mer libraries are panned or screened in accordance with the manufacturer's recommendations in which plates were coated with an antibody to capture the appropriate antibody (a goat anti-human IgG Fc for an IgG antibody for example) followed by washing. Bound phage are eluted with 0.2 M glycine-HCl, pH 2.2. After 3 rounds of selection/amplification at constant stringency (0.5% Tween), through use of DNA sequencing, one can characterize clones from the libraries that are reactive with one or more of the antibodies. Reactivity of the peptides can be determined by ELISA. For an additional discussion of epitope analysis of peptides see also Scott and Smith, *Science* 249: 386-390, 1990; Cwirla et al., *PNAS USA* 87: 6378-6382, 1990; Felici et al., *J. Mol. Biol.* 222: 301-310, 1991, and Kuwabara et al., *Nature Biotechnology* 15: 74-78, 1997.

The design of gene and/or antisense therapeutics through conventional techniques is also facilitated through the present invention. Such modalities can be utilized for modulating the function of β-hCG. In connection therewith the antibodies of the present invention facilitate design and use of functional assays related thereto. A design and strategy for antisense therapeutics is discussed in detail in International Patent Application No. WO 94/29444. Design and strategies for gene therapy are well known. However, in particular, the use of gene therapeutic techniques involving intrabodies could prove to be particularly advantageous. See e.g., Chen et al., *Human Gene Therapy* 5: 595-601, 1994 and Marasco, *Gene Therapy* 4: 11-15, 1997. General design of and considerations related to gene therapeutics is also discussed in International Patent Application No. WO 97/38137. Genetic materials encoding an antibody of the invention (such as mAb 2B2.6F5 or 2B3.3E8, or others) may be included in a suitable expression system (whether viral, attenuated viral, non-viral, naked, or otherwise) and administered to a host for in vivo generation of the antibody in the host.

Small molecule therapeutics can also be envisioned in accordance with the present invention. Drugs can be designed to modulate the activity of hCG based upon the present invention. Knowledge gleaned from the structure of the β-hCG molecule and its interactions with other molecules in accordance with the present invention, such as the antibodies of the invention, LH/hCG receptor, and others can be utilized to rationally design additional therapeutic modalities. In this regard, rational drug design techniques such as X-ray crystallography, computer-aided (or assisted) molecular modeling (CAMM), quantitative or qualitative structure-activity relationship (QSAR), and similar technologies can be utilized to focus drug discovery efforts. Rational design allows prediction of protein or synthetic structures which can interact with the molecule or specific forms thereof which can be used to modify or modulate the activity of hCG. Such structures can be synthesized chemically or expressed in biological systems. This approach has been reviewed in Capsey et al., Genetically Engineered Human Therapeutic Drugs (Stockton Press, NY, 1988). Indeed, the rational design of molecules (either peptides, peptidomimetics, small molecules, or the like) based upon known, or delineated, structure-activity relationships with other molecules (such as antibodies in accordance with the invention) has become generally routine. See, e.g., Fry et al., *Proc Natl Acad Sci USA* 95: 12022-7, 1998; Hoffman et al., *J Mol Biol* 282: 195-208, 1998; Ginalski et al., *Acta Biochim Pol* 44: 557-64, 1997; Jouko et al., *Biochem J* 322: 927-35, 1997; Singh et al., *J Med Chem* 40: 1130-5, 1997; Mandel et al., *Nat Biotechnol* 14: 323-8, 1996; Monfardini et al., *Proc Assoc Am Physicians* 108: 420-31, 1996; Furet et al., *J Comput Aided Mol Des* 9: 465-72, 1995.

Further, combinatorial libraries can be designed and synthesized and used in screening programs, such as high throughput screening efforts.

Preparation of Antibodies in Transgenic Mice

Antibodies in accordance with the invention are preferably prepared through the utilization of a transgenic mouse that has a substantial portion of the human antibody producing genome inserted but that is rendered deficient in the production of endogenous, murine, antibodies. Such mice, then, are capable of producing human immunoglobulin molecules and antibodies and are deficient in the production of murine immunoglobulin molecules and antibodies. In particular, however, a preferred embodiment of transgenic production of mice and antibodies therefrom is disclosed in U.S. patent application Ser. No. 08/759,620, filed Dec. 3, 1996, the disclosure of which is hereby incorporated by reference. See also Mendez et al., *Nature Genetics* 15: 146-156, 1997, the disclosure of which is hereby incorporated by reference.

Through use of such technology, we have produced fully human monoclonal antibodies to a variety of antigens. Essentially, we immunize lines of mice with an antigen of interest, recover lymphatic cells (such as B-cells) from the mice that express antibodies, fuse such recovered cells with a myeloid-type cell line to prepare immortal hybridoma cell lines, and such hybridoma cell lines are screened and selected to identify hybridoma cell lines that produce antibodies specific to the antigen of interest. We utilized these techniques in accordance with the present invention for the preparation of antibodies specific to β-hCG. Herein, we describe the production of multiple hybridoma cell lines that produce antibodies specific to β-hCG. Further, we provide a characterization of the antibodies produced by such cell lines, including nucleotide and amino acid sequence analyses of the heavy and light chains of such antibodies.

The antibodies derived from hybridoma cell lines for mAb 2B2.6F5 and 2B3.3E8 were expressed as discussed herein. Each of the antibodies produced by the aforementioned cell lines are either fully human IgG1 heavy chains and human IgG1 light chains. In general, antibodies in accordance with the invention possess very high affinities, typically possessing $K_d$'s of from about $10^{-9}$ through about $10^{-11}$ M, when measured by either solid phase or solution phase.

As will be appreciated, antibodies in accordance with the present invention can be expressed in cell lines other than hybridoma cell lines. Sequences encoding the cDNAs or genomic clones for the particular antibodies can be used for transformation of a suitable mammalian or nonmammalian host cells. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, particle bombardment, encapsulation of the polynucleotide(s) in liposomes, peptide conjugates, dendrimers, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, $NSO_0$, HeLa cells, baby hamster kidney (BHK) cells, monkey kidney cells (COS), human hepatocellular carcinoma cells (e.g., Hep G2), and a number of other cell lines. Non-mammalian cells including but not limited to bacterial, yeast, insect, and plants can also be used to express recombinant antibodies. Site directed mutagenesis of the antibody CH2 domain to eliminate glycosylation may be preferred in order to prevent changes in either the immunogenicity, pharmacokinetic, and/or effector functions resulting from non-human glycosylation. The expression methods are selected by determining which system generates the highest expression levels and produce antibodies with constitutive β-hCG binding properties.

Further, expression of antibodies of the invention (or other moieties therefrom) from production cell lines can be enhanced using a number of known techniques. For example, the glutamine sythetase and DHFR gene expression systems are common approaches for enhancing expression under certain conditions. High expressing cell clones can be identified using conventional techniques, such as limited dilution cloning and Microdrop technology. The GS system is discussed in whole or part in connection with European Patent Nos. 0 216 846, 0 256 055, and 0 323 997 and European Patent Application No. 89303964.4.

Antibodies of the invention can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750, 172, and 5,741,957.

In connection with functional analysis of antibodies in accordance with the present invention, such antibodies proved to be potent inhibitors of β-hCG and its binding to its LH/hCG receptor. For example, antibodies in accordance with the present invention, e.g., mAb 2B2.6F5 and 2B3.3E8 were demonstrated to bind to β-hCG and block binding of hCG to LH/hCG receptor. See FIGS. 6 and 7. For example, antibodies in accordance with the present invention, e.g., mAb 2B2.6F5 and 2B3.3E8, were shown to inhibit (ii) inhibit proliferation in vitro of BXPC-3 pancreatic carcinoma cells; and (ii) to not inhibit proliferation in vitro of MCF-7 breast carcinoma cells or HeLa cells.

The results demonstrated in accordance with the present invention indicate that antibodies of the present invention possess certain qualities that may make the present antibodies more efficacious than current therapeutic antibodies against β-hCG, for treatment of neoplastic disease.

In particular, the antibodies mAb 2B2.6F5 or 2B3.3E8 of the invention possess highly desirable properties. Their structural characteristics, functions, or activities provide criteria that facilitate the design or selection of additional antibodies or other molecules as discussed above.

Treatment Regimes

The invention provides pharmaceutical compositions comprising one or a combination of antibodies, e.g., antibodies to β-hCG (monoclonal, polyclonal or single chain Fv; intact or binding fragments thereof) formulated together with a pharmaceutically acceptable carrier. Some compositions include a combination of multiple (e.g., two or more) monoclonal antibodies or antigen-binding portions thereof of the invention. In some compositions, each of the antibodies or antigen-binding portions thereof of the composition is a monoclonal antibody or a human sequence antibody that binds to a distinct, pre-selected epitope of an antigen.

In prophylactic applications, pharmaceutical compositions or medicaments are administered to a patient susceptible to, or otherwise at risk of a disease or condition (i.e., a neoplastic disease) in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, compositions or medicants are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved. Typically, the immune response is monitored and repeated dosages are given if the immune response starts to wane.

Effective Dosages

Effective doses of the antibody compositions of the present invention, e.g., antibodies to β-hCG, for the treatment of cancer-related conditions and diseases, e.g., metastic cancer, described herein vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy.

For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody in the patient. In some methods, dosage is adjusted to achieve a plasma antibody concentration of 1-1000 μg/ml and in some methods 25-300 μg/ml. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Doses for nucleic acids encoding immunogens range from about 10 ng to 1 g, 100 ng to 100 mg, 1 μg to 10 mg, or 30-300 μg DNA per patient. Doses for infectious viral vectors vary from 10-100, or more, virions per dose.

Routes of Administration

Antibody compositions for inducing an immune response, e.g., antibodies to β-hCG, for the treatment of cancer-related conditions and diseases, e.g., metastic cancer, can be administered by parenteral, topical, intravenous, oral, subcutaneous, intraarterial, intracranial, intraperitoneal, intranasal or intramuscular means for prophylactic as inhalants for antibody preparations targeting brain lesions, and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. Intramuscular injection on intravenous infusion are preferred for administration of antibody. In some methods, particular therapeutic antibodies are injected directly into the cranium. In some methods, antibodies are administered as a sustained release composition or device, such as a Medipad™ device.

Agents of the invention can optionally be administered in combination with other agents that are at least partly effective in treating various diseases including various cancer-related diseases. In the case of tumor metastasis to the brain, agents of the invention can also be administered in conjunction with other agents that increase passage of the agents of the invention across the blood-brain barrier (BBB).

Formulation

Antibody compositions for inducing an immune response, e.g., antibodies to β-hCG for the treatment of cancer-related conditions and diseases, e.g., metastic cancer, are often administered as pharmaceutical compositions comprising an active therapeutic agent, i.e., and a variety of other pharmaceutically acceptable components. (See Remington's Pharmaceutical Science, 15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, compositions of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, *Science* 249: 1527, 1990 and Hanes, *Advanced Drug Delivery Reviews* 28: 97-119, 1997. The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins. Glenn et al., *Nature* 391: 851, 1998. Co-administration can be achieved by using the components as a mixture or as linked molecules obtained by chemical crosslinking or expression as a fusion protein.

Alternatively, transdermal delivery can be achieved using a skin patch or using transferosomes. Paul et al., *Eur. J. Immunol.* 25: 3521-24, 1995; Cevc et al., *Biochem. Biophys. Acta* 1368: 201-15, 1998.

The pharmaceutical compositions are generally formulated as sterile, substantially isotonic and in full compliance with all Good Manufacturing Practice (GMP) regulations of the U.S. Food and Drug Administration.

Diagnostic Uses

Characteristics of Antibodies and Antibody Compositions for Use as Diagnostic Reagents. Human antibodies for use in diagnostic methods to identify metastatic tumor cells, e.g., cells from metastatic epithelial cancer, colorectal carcinoma, gastric carcinoma, oral carcinoma, pancreatic carcinoma, ovarian carcinoma, or renal cell carcinoma, are preferably produced using the methods described above. The methods result in virtually unlimited numbers of antibodies and antibody compositions of the invention of any epitope binding specificity and very high binding affinity to any desired antigen. In general, the higher the binding affinity of an antibody for its target, the more stringent wash conditions can be performed in an immunoassay to remove nonspecifically bound material without removing target antigen. Accordingly, antibodies and antibody compositions of the invention used in the above assays usually have binding affinities of at least $10^8$, $10^9$, $10^{10}$, $10^{11}$ or $10^{12}$ M$^{-1}$. Further, it is desirable that antibodies used as diagnostic reagents have a sufficient on-rate to reach equilibrium under standard conditions in at least 12 hours, preferably at least five hours and more preferably at least one hour.

Antibodies and antibody compositions of the invention used in the claimed methods preferably have a high immunoreactivity, that is, percentages of antibodies molecules that are correctly folded so that they can specifically bind their target antigen. Such can be achieved by expression of sequences encoding the antibodies in *E. coli* as described above. Such expression usually results in immunoreactivity of at least 80%, 90%, 95% or 99%.

Some methods of the invention employ polyclonal preparations of antibodies and antibody compositions of the invention as diagnostic reagents, and other methods employ monoclonal isolates. The use of polyclonal mixtures has a number of advantages with respect to compositions made of one monoclonal antibody. By binding to multiple sites on a target, polyclonal antibodies or other polypeptides can generate a stronger signal (for diagnostics) than a monoclonal that binds to a single site. Further, a polyclonal preparation can bind to numerous variants of a prototypical target sequence (e.g., allelic variants, species variants, strain variants, drug-induced escape variants) whereas a monoclonal antibody may bind only to the prototypical sequence or a narrower range of variants thereto. However, monoclonal antibodies are advantageous for detecting a single antigen in the presence or potential presence of closely related antigens.

In methods employing polyclonal human antibodies prepared in accordance with the methods described above, the preparation typically contains an assortment of antibodies with different epitope specificities to the intended target antigen. In some methods employing monoclonal antibodies, it is desirable to have two antibodies of different epitope binding specificities. A difference in epitope binding specificities can be determined by a competition assay.

Samples and Target. Although human antibodies can be used as diagnostic reagents for any kind of sample, they are most useful as diagnostic reagents for human samples. Samples can be obtained from any tissue or body fluid of a patient. Preferred sources of samples include, whole blood, plasma, semen, saliva, tears, urine, fecal material, sweat, buccal, skin and hair. Samples can also be obtained from biopsies of internal organs or from cancers. Samples can be obtained from clinical patients for diagnosis or research or can be obtained from undiseased individuals, as controls or for basic research.

The methods can be used for detecting any type of target antigen. Exemplary target antigens including tumor antigens, for example, tumor antigens for metastatic epithelial cancer, colorectal carcinoma, gastric carcinoma, oral carcinoma, pancreatic carcinoma, ovarian carcinoma, or renal cell carcinoma. Other target antigens are human proteins whose expression levels or compositions have been correlated with human disease or other phenotype. Examples of such antigens include adhesion proteins, hormones, growth factors, cellular receptors, autoantigens, autoantibodies, and amyloid deposits. Other targets of interest include tumor cell antigens, such as carcinoembryonic antigen. Other antigens of interest are class I and class II MHC antigens.

Formats for Diagnostic Assays. Human antibodies can be used to detect a given target in a variety of standard assay formats. Such formats include immunoprecipitation, Western blotting, ELISA, radioimmunoassay, and immunometric assays. See Harlow & Lane, supra; U.S. Pat. Nos. 3,791,932; 3,839,153; 3,850,752; 3,879,262; 4,034,074; 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876, each incorporated herein by reference in their entirety and for all purposes.

Immunometric or sandwich assays are a preferred format. See U.S. Pat. Nos. 4,376,110; 4,486,530; 5,914,241; and 5,965,375, each incorporated herein by reference in their entirety and for all purposes. Such assays use one antibody or population of antibodies immobilized to a solid phase, and another antibody or population of antibodies in solution. Typically, the solution antibody or population of antibodies is labelled. If an antibody population is used, the population typically contains antibodies binding to different epitope specificities within the target antigen. Accordingly, the same population can be used for both solid phase and solution antibody. If monoclonal antibodies are used, first and second monoclonal antibodies having different binding specificities are used for the solid and solution phase. Solid phase and solution antibodies can be contacted with target antigen in either order or simultaneously. If the solid phase antibody is contacted first, the assay is referred to as being a forward assay. Conversely, if the solution antibody is contacted first, the assay is referred to as being a reverse assay. If target is contacted with both antibodies simultaneously, the assay is referred to as a simultaneous assay. After contacting the target with antibody, a sample is incubated for a period that usually varies from about 10 min to about 24 hr and is usually about 1 hr. A wash step is then performed to remove components of the sample not specifically bound to the antibody being used as a diagnostic reagent. When solid phase and solution antibodies are bound in separate steps, a wash can be performed after either or both binding steps. After washing, binding is quantified, typically by detecting label linked to the solid phase through binding of labelled solution antibody. Usually for a given pair of antibodies or populations of antibodies and given reaction conditions, a calibration curve is prepared from samples containing known concentrations of target antigen. Concentrations of antigen in samples being tested are then read by interpolation from the calibration curve. Analyte can be measured either from the amount of labelled solution antibody bound at equilibrium or by kinetic measurements of bound labelled solution antibody at a series of time points before equilibrium is reached. The slope of such a curve is a measure of the concentration of target in a sample.

Suitable supports for use in the above methods include, for example, nitrocellulose membranes, nylon membranes, and derivatized nylon membranes, and also particles, such as agarose, a dextran-based gel, dipsticks, particulates, microspheres, magnetic particles, test tubes, microtiter wells, SEPHADEX™. (Amersham Pharmacia Biotech, Piscataway N.J.) Immobilization can be by absorption or by covalent attachment. Optionally, antibodies can be joined to a linker molecule, such as biotin for attachment to a surface bound linker, such as avidin.

Labels

The particular label or detectable group used in the assay is not a critical aspect of the invention, so long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, Texas red, rhodamine, and the like), radiolabels (e.g., $^3$H, $^{14}$C, $^{35}$S, $^{125}$I, $^{121}$I, $^{112}$In, $^{99m}$Tc), other imaging agents such as microbubbles (for ultrasound imaging), $^{18}$F, $^{11}$C, $^{15}$O, (for Positron emission tomography), $^{99m}$TC, $^{111}$In (for Single photon emission tomography), enzymes (e.g., horse radish peroxidase, alkaline phosphatase and others commonly used in an ELISA), and calorimetric labels such as colloidal gold or colored glass or plastic (e.g. polystyrene, polypropylene, latex, and the like) beads. Patents that described the use of such labels include U.S. Pat. Nos. 3,817,837; 3,850,752; 3,939,350; 3,996,345; 4,277,437; 4,275,149; and 4,366,241, each incorporated herein by reference in their entirety and for all purposes. See also *Handbook of Fluorescent Probes and Research Chemicals*, $6^{th}$ Ed., Molecular Probes, Inc., Eugene Oreg.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, and the like Chemiluminescent compounds include luciferin, and 2,3-dihydrophthalazinediones, e.g., luminol. For a review of various labeling or signal producing systems which may be used, see, U.S. Pat. No. 4,391,904, incorporated herein by reference in its entirety and for all purposes.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Frequently, the β-hCG proteins and antibodies to β-hCG will be labeled by joining, either covalently or non-covalently, a substance which provides for a detectable signal.

Toxicity

Preferably, a therapeutically effective dose of the antibody compositions described herein will provide therapeutic benefit without causing substantial toxicity.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1, Kits Also within the scope of the invention are kits comprising the compositions (e.g., monoclonal antibodies, human sequence antibodies, human antibodies, multispecific and bispecific molecules) of the invention and instructions for use. The kit can further contain a least one additional reagent, or one or more additional human antibodies of the invention (e.g., a human antibody having a complementary activity which binds to an epitope in the antigen distinct from the first human antibody). Kits typically include a label indicating the intended use of the contents of the kit. The term label includes any writing, or recorded material supplied on or with the kit, or which otherwise accompanies the kit.

The following cDNA clones described in the specification and further described in the examples below will be deposited with the American Type Culture Collection, 10801 University Boulevard, Manassas, Va. 20110-2209 under the Budapest Treaty on Aug. 8, 2006. The hybridoma cell line for mAb 2B2.6F5 has the ATCC Patent Deposit Designation No. indicated: PTA-7777. The hybridoma cell line for mAb 2B3.3E8 has the ATCC Patent Deposit Designation No. indicated: PTA-7775.

Date of Deposit: Aug. 8, 2006
Name and Complete Address of the Depository Authority:
American Type Culture Collection
10801 University Boulevard
Manassas, Va. 20110-2209
Other embodiments and uses will be apparent to one skilled in the art in light of The present disclosures.

EXEMPLARY EMBODIMENTS

Example 1

Antigens

The immunogen for generation of monoclonal antibodies was the, conjugate of a peptide and a carrier protein. The peptide was based on beta-hCG L2 Long Loop amino acids 38-57 (LP, Loop Peptide). The carrier protein was diphtheria toxoid (DT, Sanofi Aventis, Toronto, Canada). The chemical name of this antigenic formulation is Ala-($Pro_6$)-beta-hCG (38-57)-Gly[$Hyp^{39}$]-DT conjugate. Hydroxyproline was substituted for proline at position 39 of the beta-hCG protein sequence. Amino acid sequence of the beta-bCG(38-57) LP is Ala-Pro-Pro-Pro-Pro-Pro-Pro-Cys-Hyp-Thr-Met-Thr-Arg-Val-Leu-Gln-Gly-Val-Leu-Pro-Ala-Leu-Pro -Gln-Val-Val-Cys (SEQ ID NO:7). The homologous L2 Long Loop of any other glycoprotein cystine knot growth factor could be substituted for residues 38-57 of beta-hCG with or without hydroxyproline substitution at position 39. Alternative carrier proteins would also be amenable to this procedure. See U.S. Pat. No. 6,716,428.

Loop Peptide (LP) was synthesized by standard Fmoc synthesis methods using an automated process on an ACT synthesizer and the manufacturer's directions (Advanced ChemTech, Louisville, Ky.). Dimethylformamide (DMF), Dichloromethane (DCM), Trifluoroacetic acid (TFA), 1,2 Ethanedithiol (EDT), N,N-Diisopropylethylamine (DIEA), and Benzotriazolyl N-oxy-trisdimethylaminophosphonium hexafluorophosphate (BOP) were obtained from Sigma (St. Louis, Mo.). Fmoc-protected-glycine-p-alkoxybenzyl alcohol resin (Wang resin) served as the solid support. This was prepared by washing in DMF and DCM. Fmoc-Gly was deprotected with 20% piperidine in DMF. After coupling, the resin was washed in DMF. Fmoc cysteine, the next amino acid residue in the LP was coupled using DIEA in the presence of BOP. Coupling efficiency was checked with ninhydrin. If the coupling was incomplete, up to two additional coupling cycles were repeated. After completion of 27 standard cycles of deprotection, neutralisation, coupling, and washing, a sample of peptide resin was evaluated for amino acid composition prior to cleavage of the completed peptide mixture from the resin. Protected peptide-resin was exposed to a Cleavage reagent consisting of p-cresol:TFA:EDT:$H_2O$ for two hours to cleave peptide from resin and to remove side chain protecting groups. The peptide/resin mixture was washed successively with ethyl ether over a sintered glass funnel. This was followed by 70% acetic acid in order to dissolve the peptide and separate it from the resin. The crude peptide was cyclized via formation of an intra-chain disulfide bond by treatment with potassium ferricyanide ($K_3Fe(CN)_6$) for 20 hours at room temperature. Cyclized peptide was removed from non-cyclized peptide by ion exchange chromatography over a Biorex-70 cation exchange resin (Bio-Rad, Hercules, Calif.) with 70% acetic acid. Chromatographed pools of peptide were checked by reverse phase high performance liquid chromatography (RP HPLC) to assess peptide admixture. Peptide was purified from crude cyclized mixture in two stages. First, low-pressure reversed phase chromatography was performed on a $C_{18}$ silica resin with a 0.1% trifluoroacetic acid plus acetonitrile gradient. This was followed by anion exchange chromatography over an AG-1×8 anion exchange column (Bio-Rad, Hercules, Calif.) with elution using 10% acidic acid. Aliquots were tested for purity by thin layer chromatography and reverse phase HPLC. Peptide aliquots of adequate purity were lyophilized to remove remaining solvent. Dry aliquots of peptide were dissolved in USP Purified Water and shell frozen, then lyophilized. Aliquots were then pooled, and yield was established by weighing.

Diphtheria toxoid (DT, Sanofi-Aventis, Toronto, Canada) was used as the carrier in the examples described. However, as is known to those skilled in the art, many different carrier proteins could be employed for this purpose. DT manufacture is based on toluene treatment of a culture of *Corynebacterium diphtheriae* strain L34T1. The toxin is purified, dialysed, detoxified with formaldehyde, and concentrated by ultrafiltration. After ammonium sulfate precipitation, toxoid is dissolved and diafiltered to remove ammonium sulfate.

LP-DT conjugate was produced by a double two-stage process using two different heterobifunctional linker reagents, N-succinimidyl-3(2-pyridylthio) propionate (SPDP, Pierce Chemical, Rockford, Ill.) and ε-maleimidocaproic acid N-hydroxysuccinimide ester (eMCS, Sigma Aldrich Fine Chemicals, St. Louis, Mo.). The process resulted in conjugation of lysine amino groups in DT (via SPDP) to the amino terminus of the peptide (via eMCS). Purified DT was reacted with SPDP to form an intermediate, SPDP-DT. LP was reacted with eMCS to form another intermediate, maleimido-LP (M-LP). SPDP-DT and M-LP were then reacted with each other to form LP-DT conjugate via a thioether bond. Removal of unreacted reagents, purification of intermediates, and buffer exchanges were accomplished via sequential diafiltration steps. Purified DT was adjusted to 20 mg/ml with Sodium Borate buffer, pH 9.2. SPDP was added at 10 ml/min sufficient to activate DT for coupling at 18 moles of peptide per mole DT. The mixture was stirred for one hour at room temperature to allow coupling of SPDP via its activated N-hydroxysuccinimide ester to amino groups of the DT to produce SPDP-DT. This reaction mixture was concentrated then purified by diafiltration against 30 volumes of Citrate Coupling Buffer (CCB, pH 6.0). Samples were assessed for pH (6.0±0.2), purity by size exclusion chromatography HPLC, protein concentration by Lowry, and thiol quantification by 5,5'-dithio-bis-2-nitrobenzoic acid (Ellman's reagent, Sigma-Aldrich, St. Louis, Mo.) to confirm 15-21 moles per mole of DT. LP was reacted with the N-hydroxysuccinimidyl ester of eMCS sufficient to produce a molar quantity of the M-LP intermediate to react with one mole of SPDP-DT. M-LP was purified over a column of Sephadex G10 (Pharmacia, Uppsala, Sweden). Maleimido content was quantitated using Ellman's Reagent. SPDP-DT was reacted with M-LP to produce LP-DT conjugate. Purified SPDP-DT solution was adjusted with CCB to approximately 20 mg/ml. Sufficient M-LP Peptide at 50 mg/ml in CCB was added at 10 ml/min to couple 18 moles of peptide per mole of DT. The reaction mixture was stirred for at least 6 hours at RT to allow coupling of LP via the maleimido of its C-terminal glycine residue to the thiol moiety of SPDP-DT to produce the LP-DT conjugate. The conjugate reaction mixture was then concentrated to approximately 30 mg/ml and purified by diafiltration against 15 volumes of PBS (pH 7.2). pH was tested (7.2±0.2). Purity was confirmed by SEC HPLC. Purified LP DT was then filtered through a sterile 0.22 μm filter (Millipore, Billerica, Mass.) and adjusted with sterile PBS (pH 7.2) to produce a final bulk LP-DT concentrate that was lyophilized prior to storage.

Example 2

Immunizations

As is known to those skilled in the art, female C57BL/6 mice (Charles River Laboratories, Wilmington, Mass.) were selected for immunizations due to the known propensity of this inbred mouse strain to generate a humoral response and hybridomas specific for beta-hCG. All procedures involving animals were reviewed by an Institutional Animal Care and Use Committee. Mice were immunized in groups of three. All immunizations were subcutaneous or intramuscular in either one or two sites. LP-DT conjugate was solubilized in sterile water then thoroughly emulsified in either Complete Freund's Adjuvant (CFA; Sigma-Aldrich, St. Louis, Mo.) or Incomplete Freund's Adjuvant (IFA; Sigma-Aldrich, St. Louis, Mo.). CFA was vortexed prior to use. Emulsification was performed by mixing the aqueous immunogen solution and either CFA or IFA between two 1 ml glass syringes connected by a luer lock, approximately 20 times, until the mixture became milky white and became difficult to push. Final immunogen concentration was 0.5 milligrams per milliliter.

In the first hybridoma generation (Fusion 1), initial immunizations were with 0.1 mg of LP-DT conjugate in CFA. Each of two sites were injected subcutaneously with 0.1 milliliter of emulsified immunogen via a 25 gauge needle (Becton-Dickinson, Franklin Lakes, N.J.). Subsequent immunizations were performed at two-week intervals with 0.05 milligrams of loop-DT conjugate in IFA, each time injected to two sites. Two weeks after the fourth immunization, tail bleeds were performed to assess binding capacity of serum from each mouse. Mice were mobilized individually in a restraining device, and the tail was heated for a minute or so under an infrared lamp. After swabbing with alcohol, the mouse tail was lanced with a scalpel and several drops of blood were obtained. Blood was incubated for one hour at 37° C. Each tube was then flicked to dislodge the blood clot prior to storage overnight at 4° C. Tubes were spun at 10,000 g, and serum was transferred from each tube to a separate container. Sera were frozen at −20° C. prior to screening.

In a second experiment (Fusion 2), mice were immunized on three occasions separated by four week intervals. As previously, the initial immunization was with 0.10 milligrams per mouse, whereas subsequent immunizations were with 0.5 milligrams per mouse. Priming and other procedures were the same.

Example 3

Radioimmunoassays

Serum, culture supernatant, or purified antibody samples were diluted in Phosphate Buffered Saline (PBS) containing 10% mouse serum (MS) and 1 millimolar ethylenediaminetetraacetate (EDTA). Initial dilutions for screening purposes were 1:10. Other reagents include PBS containing 1% (w/v) bovine serum albumin (BSA); $^{125}$I hCG at 2.5 ng/ml; assay controls with representative rabbit antisera specific for hCG having high, medium, and low antibody levels revealed by prior testing; non-specific monoclonal antibody serum; PBS-EDTA containing 40% calf serum (40% CS); and 25% (w/v) polyethylene glycol (PEG). $^{125}$I hCG was prepared by the Chloramine T method.

100 microliters of PBS containing 1% (w/v) bovine serum albumin (BSA) was added in quadruplicate to sets of four 10×75 mm disposable glass tubes. 100 microliters of $^{125}$I hCG at 2.5 nanograms/milliliter was then dispensed into all sets of tubes, as well as to an additional single set of four empty tubes (to serve as total count tubes). 100 microliters of diluted sample was then added to quadruplicate sets of tubes. Sets of tubes were included with non-specific monoclonal antibody serum as a negative control and the three representative anti-hCG antisera as positive controls. Tubes were shaken gently to mix, placed in plastic finger racks, then covered with parafilm, followed by aluminum foil. Racks of covered plastic tubes were incubated for 16-24 hours at 4° C. Tubes were then uncovered, and to each tube was added 100 microliters of PBS-EDTA-40% CS, followed by 400 microliters of 25% PEG. Subsequent vortexing of tubes was followed by incubation for 15 minutes at room temperature. Tubes were then centrifuged for 20 minutes at 4° C. and 1500×g. Liquid was decanted, and radioactivity remaining within tubes was counted in a gamma spectrometer for at least one minute per tube.

Mean counts per minute were calculated for each quadruplicate set of tubes. This was corrected by subtraction of the mean count from the tubes with non-specific monoclonal antibody serum. The bound/free (B/F) ratio was calculated for each dilution. (Total Counts-Bound=Free counts)

Receptor Binding Assay. Testes from adult male rats were decapsulated and torn apart in PBS using 19 gauge needles on 2.0 ml syringes. The mass of dispersed material was stirred for five minutes, filtered through nylon mesh and cotton wool, then centrifuged at 120 g for twenty minutes. Homogenate equivalent to 100 micrograms protein was transferred a 10×75 mm tube. 100 microliters of $^{125}$I hCG at 2.5 nanograms/milliliter was then dispensed into all sets of tubes, as well as to an additional single set of four empty tubes (to serve as total count tubes). 100 microliters of diluted sample was then added to quadruplicate sets of tubes. A standard curve was constructed with 5, 10, 25, 50, and 100 ng unlabeled hCG. Additional sets of tubes were prepared with increasing concentrations of monoclonal antibody. Tubes were shaken gently to mix, placed in plastic finger racks, then covered with parafilm, followed by aluminum foil. Racks of covered plastic tubes were incubated for 16-24 hours at 4° C. 100 microliters of PBS-EDTA-40% CS was then added to each tube, followed by 400 microliters of 25% PEG. Tubes were vortexed then incubated for 15 minutes at room temperature. After centrifugation at 1500×g for 20 minutes at 4° C., liquid was decanted. Pellet radioactivity was counted in a gamma spectrometer for at least one minute per tube per tube. Mean counts per minute were calculated for each quadruplicate set of tubes.

Example 4

Cell Lines and Culture and Hybridoma Generation

NS-1 murine myeloma cells and three human cell lines with the following phenotypic characteristics were obtained from the American Type Culture Collection (ATCC), Manassas, Va. First, BXPC-3 human pancreatic carcinoma cells produce beta-hCG protein but do not express the LH/hCG receptor to which the hCG heterodimer binds. Second, MCF-7 human breast carcinoma cells by contrast produce little or no beta-hCG protein but do express the LH/hCG receptor to which the hCG heterodimer (but not the beta-hCG chain alone) binds. Finally, HeLa human cervical carcinoma cells produce both the common alpha chain of the human heterodimeric glycoprotein family and the LH/hCG receptor.

NS-1 myeloma and hybridoma cells were cultured in RPMI-1640 (Sigma-Aldrich, St. Louis, Mo.). Media was supplemented with 10% fetal bovine serum (FBS), 100 units/milliliter penicillin, 0.1 milligrams/milliliter streptomycin, and 2 mM L-glutamine. For initial hybridoma culture following fusion and for limiting dilution subcloning, 20% FBS was employed. RPMI was also supplemented with penicillin at a final concentration of 100 units per milliliter; streptomycin at 100 micrograms per milliliter. Hybridoma selection media was made by addition of Hybri-Max HAT Media Supplement (Sigman-Aldrich Biotechnology, St. Louis, Mo.) to RPMI 1640 with 10% FBS, penicillinj, streptomycin, and L-glutamine to obtain a final working concentration of 100 μM hypoxanthine, 0.4 μM aminopterin, and 16 μM thymidine. BXPC-3 and MCF-7 cells were cultured in RPMI 1640 with 10% FBS, penicillin-streptomycin, and L-glutamine. HeLa cells were cultured in DMEM with 10% FBS and penicillin-streptomycin. Cell culture media were obtained from Mediatech, Inc. (Herndon, Va.) or Sigma-Aldrich (St. Louis, Mo.).

Cell culture was performed at 37° C. in a humidified atmosphere of 5% $CO_2$. Once cell concentration in culture reached approximately $10^6$ cells per milliliter, a 1:10 or 1:20 dilution with fresh media was performed. Cell freezing was performed as follows. Rapidly dividing cells in good health were transferred to a sterile, chilled centrifuge tube and spun at 400 g for five minutes at 4° C. Supernatant was decanted, and the pellet was resuspended with 75% RPMI/20% FBS/5% DMSO sufficient to generate a final cell concentration of approximately $10^7$ cells per milliliter. 0.5 ml aliquots of this suspension were distributed to freezing vials on ice. Vials were stored in a freezing rack at −70° C. overnight, followed by long term storage at −185° C. in liquid nitrogen. Cells are thawed by warming a frozen vial in a 37° C. water bath. After washing with RPMI 1640/10% FBS at room temperature, cells are resuspended 10 ml of the same media and cultured at 37° C.

Hybridoma Generation. Polyethylene glycol 1500 (PEG 1500, Boehringer Mannheim, Indianapolis, Ind.) and fetal bovine serum (FBS, Invitrogen/GIBCO, Carlsbad, Calif.) were pre-screened for capacity to support cell fusion and hybridoma growth, respectively. NS-1 myeloma cells were confirmed to be free of mycoplasma via a mycoplasma testing service (Bionique Testing Laboratories, Saranac Lake, N.Y.).

Mice received an antigenic boost with 0.05 μg LP-DT conjugate via the intravenous (tail) route four days prior to fusion. This was intended to induce B lymphocyte cell cycling, as well as to promote migration of B lymphocytes to the spleen. On the day of cell fusion, 0.5 gram PEG 1500 was melted in a 50° C. water bath, combined with 0.5 ml of unsupplemented RPMI, and maintained in a 37° C. water bath. Animals were sacrificed by cervical dislocation. The spleen was removed aseptically and placed in a 100 mm tissue culture plate that contained 10 ml of unsupplemented RPMI 1640 at 37° C. The spleen was torn apart into small pieces using 19-gauge needles on 2.0 ml syringes until most cells were released. Cell clumps were disrupted by pipetting. Cells and media were transferred to a sterile 50-ml polystyrene centrifuge tube. The tissue culture plate was washed with an additional 10 ml of unsupplemented RPMI 1640, which was then added to the contents of the centrifuge tube. After three minutes, supernatant was pipetted away from settled debris to a new sterile 50-ml centrifuge tube. Splenocytes so obtained were washed twice in unsupplemented, prewarmed RPMI 1640 and centrifuged at 400 g for 5 minutes. Log phase myeloma cells were washed once in unsupplemented RPMI 1640. Washed splenocytes and myeloma cells were counted visually using a Neubauer chamber hemocytometer (Reichert Scientific Instruments, Buffalo, N.Y.). Up to 1,000,000,000 splenocytes were then combined with 20,000,000 NS-1 myeloma cells and centrifuged at 400 g for five minutes. The 50% PEG 1500 solution at 37° C. was transferred slowly over one minute to the splenocyte-myeloma cell pellet with simultaneous cell resuspension by use of a sterile Pasteur pipet. After one minute of gentle stirring, ten ml of prewarmed, unsupplemented RPMI 1640 was added over the ensuing two minutes. The cells were centrifuged at 400 g for five minutes, decanted, and resuspended using 50 ml of RPMI 1640 supplemented with 20% FBS, penicillin-streptomicin, L-glutamine, and HAT. 0.5 ml of HAT selection media with cells was transferred to each well of 4 24-well tissue culture plates. Cells were fed the next day with and equal volume of 2×HAT selection media. 6 days later cells were fed again with 1×HAT selection media, and supernatants were harvested from wells with visible colonies of cells. Intermittent supernatant harvesting continued for about two weeks as additional cell colonies became visible. Supernatants were screened as described in Example 3 (Radioimmunoassays). Wells with supernatants positive in the initial screen were rescreened.

Those wells shown reproducibly to bind heterodimeric hCG were expanded to 10 ml of culture and frozen.

Limiting Dilution Subcloning. 96-well plates were prepared with RPMI supplemented with 10% FBS, penicillin, streptomycin, and L-glutamine. Hybridoma cells were counted then resuspended in 20 milliliters of media at 20, 10, and 2 cells/milliliter. Each cell suspension was then plated to two 96-well plates (Fisher Scientific, Ottawa, Ontario, Canada) at 100 microliters per well using a multichannel pipettor (Fisher Scientific, Ottawa, Ontario, Canada). Six days later cells were fed with the same media. Wells with apparently clonal populations of cells were screened either by radioimmunoassay as described or by use of an hCG enzyme-linked immunosorbent assay (Rock, E. P., et al. Immunogenicity of a fusion protein linking the beta subunit carboxyl terminal peptide (CTP) of human chorionic gonadotropin to the B subunit of *Escherichia coli* heat-labile enterotoxin (LTB). Vaccine. 14: 1560-1568. 1996). Detection was via horseradish peroxidase-conjugated Rabbit Anti-Goat IgG Heavy and Light Chain antibodies (Bethyl Laboratories, Montgomery, Tex.), followed by Chemiluminescent Peroxidase Substrate for ELISA (Sigma-Aldrich, St. Louis).

Isotype Determination Cryopreservation, and *Mycoplasma* Testing. Isotype determination was performed for individual monoclonal antibodies with the Immunotype Mouse monoclonal antibody typing kit (Sigma Chemical Co., St. Louis, Mo.) by following the manufacturer's instructions in an ELISA format with one microgram of Protein G purified monoclonal antibody per well of a 96-well plate as the solid phase. Monoclonal antibodies of known isotype were used as controls. Freezing media for cryopreservation contained 75% RPMI, 20% FBS, and 5% dimethyl sulfoxide (DMSO) (Sigma-Aldrich, St. Louis, Mo.). For cryopreservation, cells were spun at 4° C., then resuspended slowly in freezing medium at 20,000,000 cells/milliliter and aliquoted to freezing vials. Vials were frozen slowly in Styrofoam boxes to −70° C. then transferred one day later to liquid nitrogen. *Mycoplasma* testing was performed by Bionique Testing Laboratories (Saranac Lake, N.Y.).

Gene Sequencing. Cytoplasmic RNA was obtained from hybridoma cells using a Cytoplasmic and Nuclear RNA Purification Kit from Norgen Biotek (St Catherines, Ontario, Canada) via the manufacturer's protocol. Full-length poly(A) RNA was then selected and prepared for amplification using the Ambion FirstChoice RLM-RACE Kit (Applied Biosystems, Foster City, Calif.) via the manufacturer's protocol. 3' primers were obtained from Invitrogen (Carlsbad, Calif.). Nested PCR was performed, and the inner reaction was run on an agarose gel. A band of the correct predicted fragment size was excised and extracted with a Gel Extraction Kit (Qiagen, Valencia, Calif.) via the manufactuerer's protocol. Purification from contaminating primers, nucleotides, DNA polymerase, oil, and salts was performed using the GenElute PCR Clean-Up Kit (Sigma-Aldrich, St. Louis, Mo.). DNA sequencing was then performed on an Applied Biosystems sequencer (Foster City, Calif.) via the manufacturer's protocol.

Monoclonal Antibody Production and Purification. Hybridoma cells were grown in 250 ml RPMI with 10% FBS, penicillin, streptomycin, and L-glutamine using Corning polystyrene roller bottles revolving at two revolutions per minute (Fisher Scientific, Ottawa, Ontario, Canada). As the culture reached saturation of about 1,000,000 cells per milliliter, cells were removed by centrifugation. Antibody was concentrated by ammonium sulfate precipitation followed by resuspension and dialysis overnight at 4° C. to 20 millimolar sodium phosphate, pH 7.0. Subsequent antibody purification was performed using Hi-Trap Protein G columns (GE Healthcare/Amersham Biosciences, Uppsala, Sweden) via the manufacturers protocol. Elution from the column was with 0.1 molar glycine-HCl, pH 2.7. Following elution, the eluate was subsequently buffered with 1.0 molar Tris to pH 7.0, followed by dialysis overnight at 4° C. to phosphate-buffered saline (PBS) using 12,000 molecular weight cut-off tubing. Antibodies were stored at 4° C. or frozen in either PBS or water with 50% glycerol.

Example 5

Cancer Cell Proliferation and Xenografts

Effects on cancer cell proliferation were assessed as follows. 96-well plates were seeded with $10^3$ cells per well in culture media. Either 2 or 20 micrograms of purified monoclonal antibody was added to each well. Murine monoclonal antibody, muromonab-CD3 (OKT3; Orthoclone OKT3, Ortho Biotech Products, L.P., Bridgewater N.J.), was used as a negative control. Cells were cultured for 72 hours prior to harvesting for measurement of cell proliferation by two methods.

The MTS colorimetric assay measures cellular reductive capacity of NADH and NADPH. These moieties are produced by dehydrogenases in metabolically active cells and decrease with declining cell viability. MTS reagent was added to 96-well cell cultures as recommended by the manufacturer (CelTiter 96 AQueous Non-Radioactive Cell Proliferation Assay; Promega, Madison Wis.), and absorbance was read at 492 nm. Data are presented as mean % inhibition [(1−(experimental absorbance−background absorbance)/ (absorbance of control cultures−background absorbance))× 100]±SD for triplicate determinations.

Figure 8:
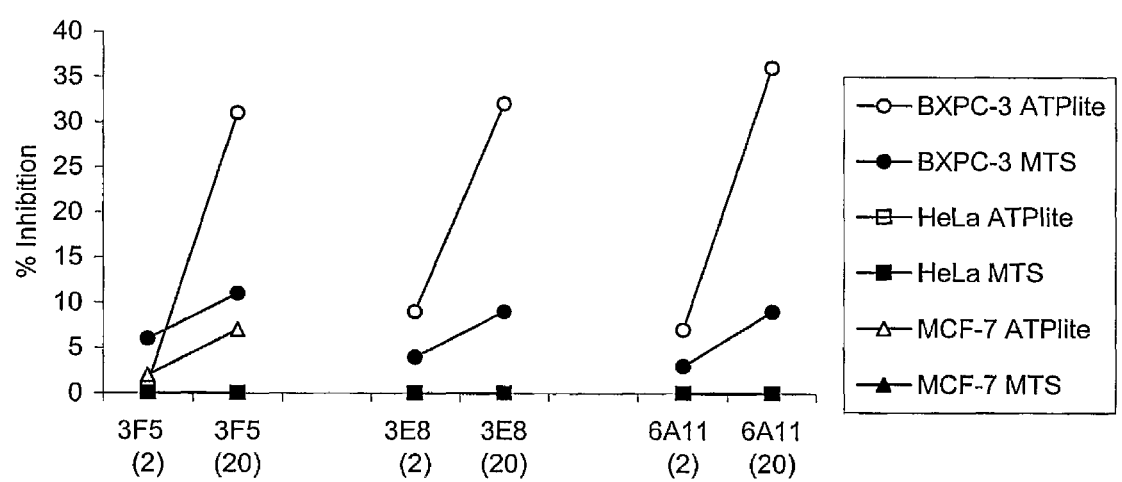
Figure 9:
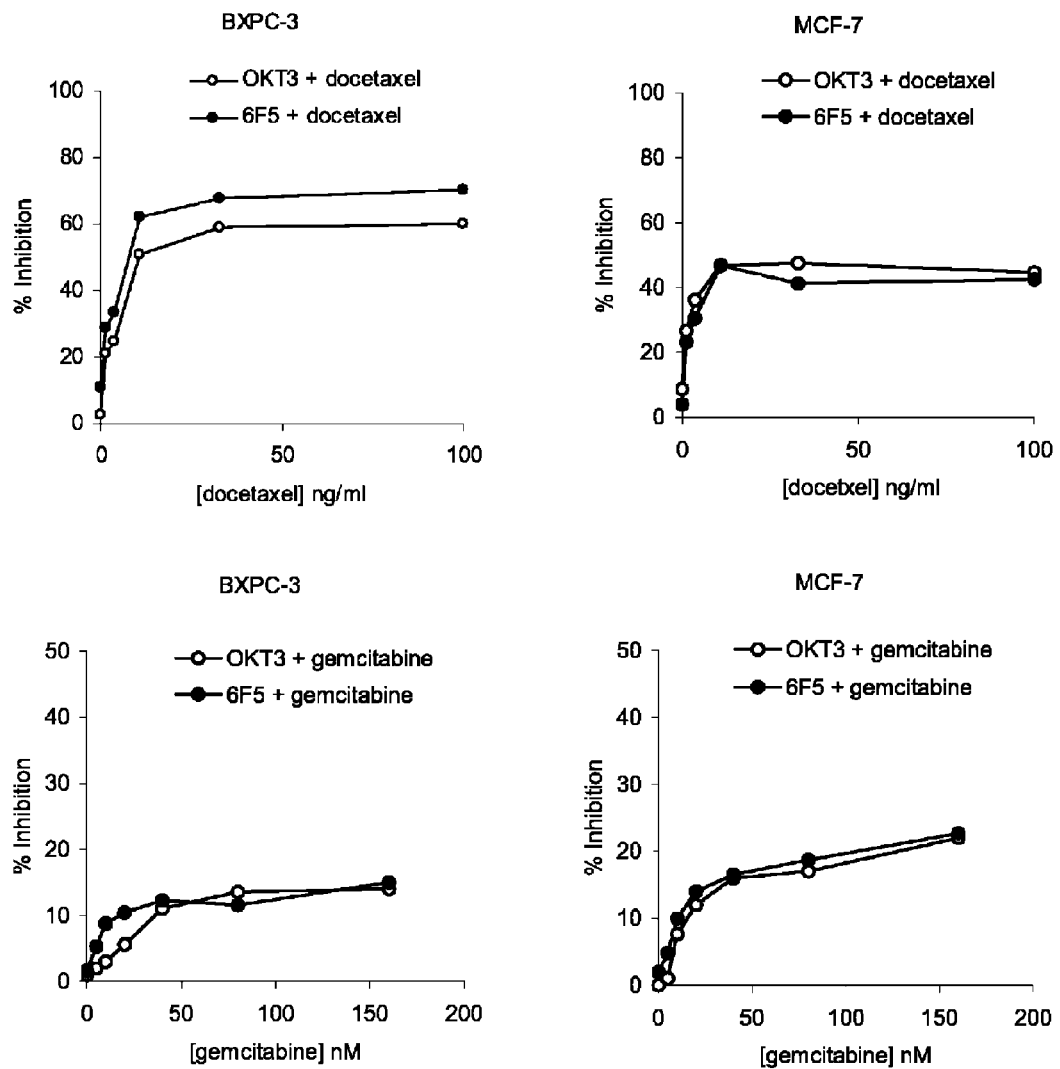

Intracellular ATP concentration was determined with the ATPlite™ Luminescence ATP Detection Assay System (PerkinElmer Life Sciences, Wellesley, Mass.) according to the manufacturer's directions. The procedure is described in U.S. patent application Ser. No. 09/806,165, which is incorporated as a reference herein. Advantages of this assay include sensitivity, linearity, and simplicity. In this test, ATP is converted to light by firefly (*Photinus pyralis*) luciferase. The light generated can be quantified as counts per second (cps) in a luminescence counter. Care was taken to avoid contamination of reagents in this kit with ATP present in the environment, e.g. on the hand. Gloves were worn at all times during the procedure. 50 microliters of the manufacturer's cell lysis solution is added to 100 microliters of cell suspension in wells of a 96-well microplate. The plate is incubated for five minutes on an orbital shaker operating at 700 revolutions per minute (rpm). 50 microliters of the manufacturer's substrate solution is then added to wells containing cell lysates, and the plate is again incubated for five minutes in an orbital shaker at 700 rpm. The plate is dark adapted for at least ten minutes, following which luminescence is read in either of two PerkinElmer luminometers. In each experiment, only one type of luminometer was used. Data in FIGS. 8 and 9 are presented as mean % inhibition [(1−experimental cps/control cps)×100%]±SD for triplicate determinations.

Human-Mouse Tumor Xenografts. Seven-week-old NCR male athymic nude homozygous (nu/nu) mice were purchased from Taconic (Germantown, N.Y.). Four groups of ten mice per group were inoculated subcutaneously on the flank in the mid-axillary line with $2 \times 10^6$ BXPC-3 cells on Day 1. A negative control group subsequently received no treatment (NT). The docetaxel group received intraperitoneal docetaxel at 30 milligrams/kilogram body weight in three treatments at 1-week intervals starting on Day 10. The 6F5 group received 100 micrograms of anti-beta-hCG L2 loop monoclonal antibody 6F5 in six treatments at twice weekly intervals starting on Day 6. A 6F5+docetaxel group received both docetaxel and monoclonal antibody 6F5 at the above doses and intervals. Mice were assessed twice weekly for bidimensional size of human tumor xenografts by use of a digital microcaliper device. Tumor volume in cubic millimeters was calculated for each mouse by use of the formula (length×width$^2$)÷2. Data are expressed for groups as the mean tumor volume+/−the standard error of the mean.

Example 6

LP-DT Conjugate Generates Monoclonal Antibodies Specific for the Beta-hCG L2 Loop Three female C57BL/6 mice were immunized with LP-DT conjugate on four occasions at three week intervals prior to Fusion 1. Similar mice were immunized on three occasions at three week intervals prior to Fusion 2. The mouse with the highest RIA titer against hCG after each series of immunizations was sacrificed for fusion with NS-1 cells and consequent hybridoma production. Fusion 1 yielded monoclonal antibodies 2B3.3E8 (3E8), 2B3.3F5 (3F5), and 2B3.6A11 (6A11). Fusion 2 yielded 2B2.6F5 (6F5). Specific binding to $^{125}$I hCG was verified after growth and purification of all monoclonal antibodies. All four of these antibodies were found to have an IgG1 isotype.

Figure 6:
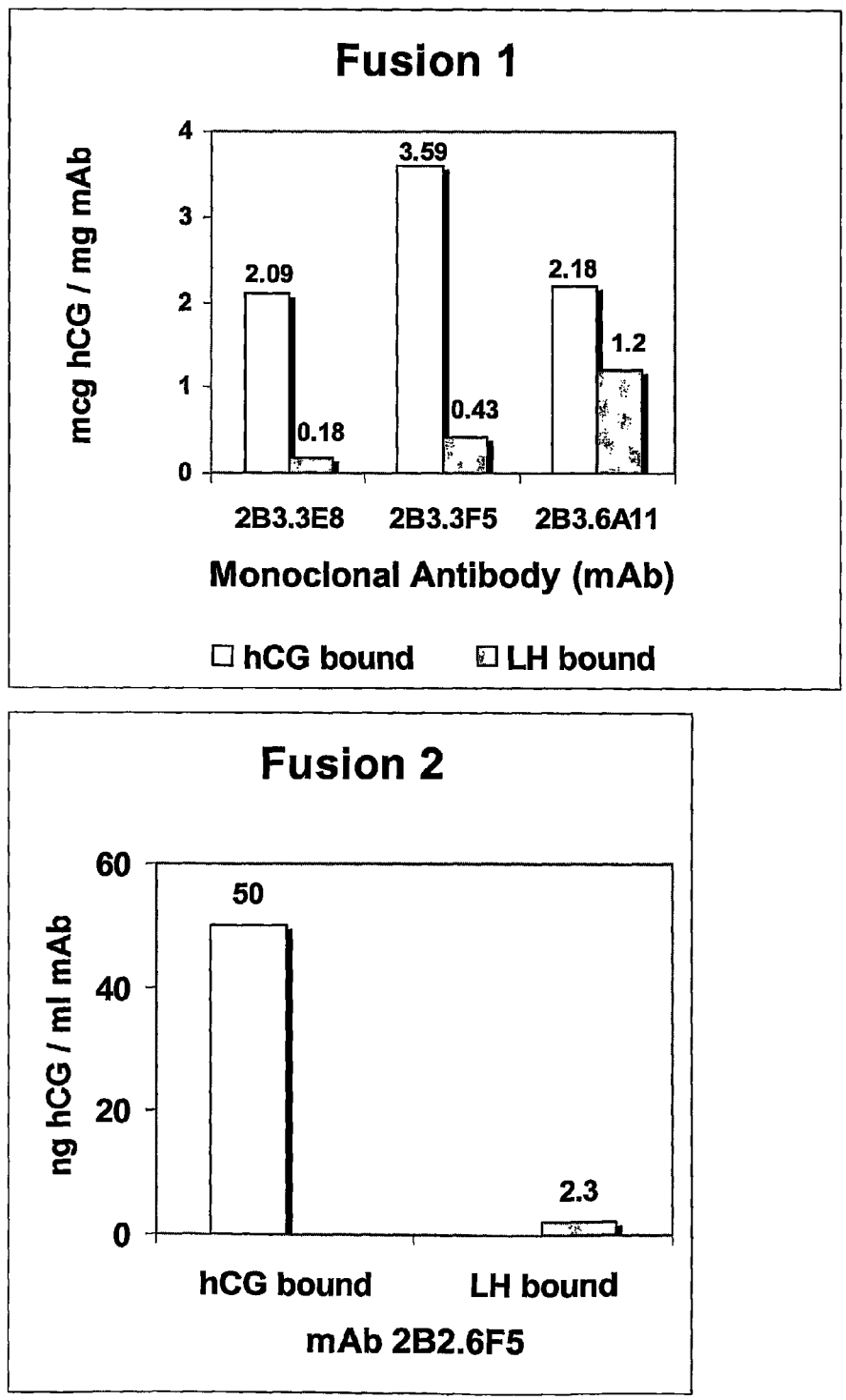

Cross-reactivity to LH was assessed by RIA via competition experiments with unlabeled LH. Standard curves with unlabeled hCG were constructed for each antibody and compared to curves generated using LH. The relative amount of LH to generate an equivalent drop in counts to that of the hCG standard curve was used to establish the degree of cross-reactivity. A similar experiment was performed with antibody 6F5 from Fusion 2. However, in the latter instance culture supernatant of undocumented concentration was tested. Results are shown in FIG. 6. Fusion 1 antibodies 3E8, 3F5, and 6A11 displayed 8.6%, 12%, and 55% cross-reactivity for LH, respectively. Fusion 2 antibody 6F5 displayed 4.6% cross-reactivity. These results demonstrate that immunization with the LP-DT conjugate is able to lead to generation of monoclonal antibodies with strong preferential binding to hCG over LH despite only a one amino acid difference between these two proteins in the surface-accessible residues of the beta-hCG L2 loop.

Monoclonal antibody 2B2.6F5 was grown in greater quantity for a xenograft experiment. In one production run, 781 milliliters of culture supernatant yielded 23 mg of antibody by Protein G purification. In a second such production experiment with 2B2.6F5 after limiting dilution subcloning, 1.5 liters of culture yielded 48 milligrams of purified antibody.

Example 7

Anti-Beta-hCG L2 Loop Antibodies Block Binding of hCG to LH/hCG Receptor

Figure 7:
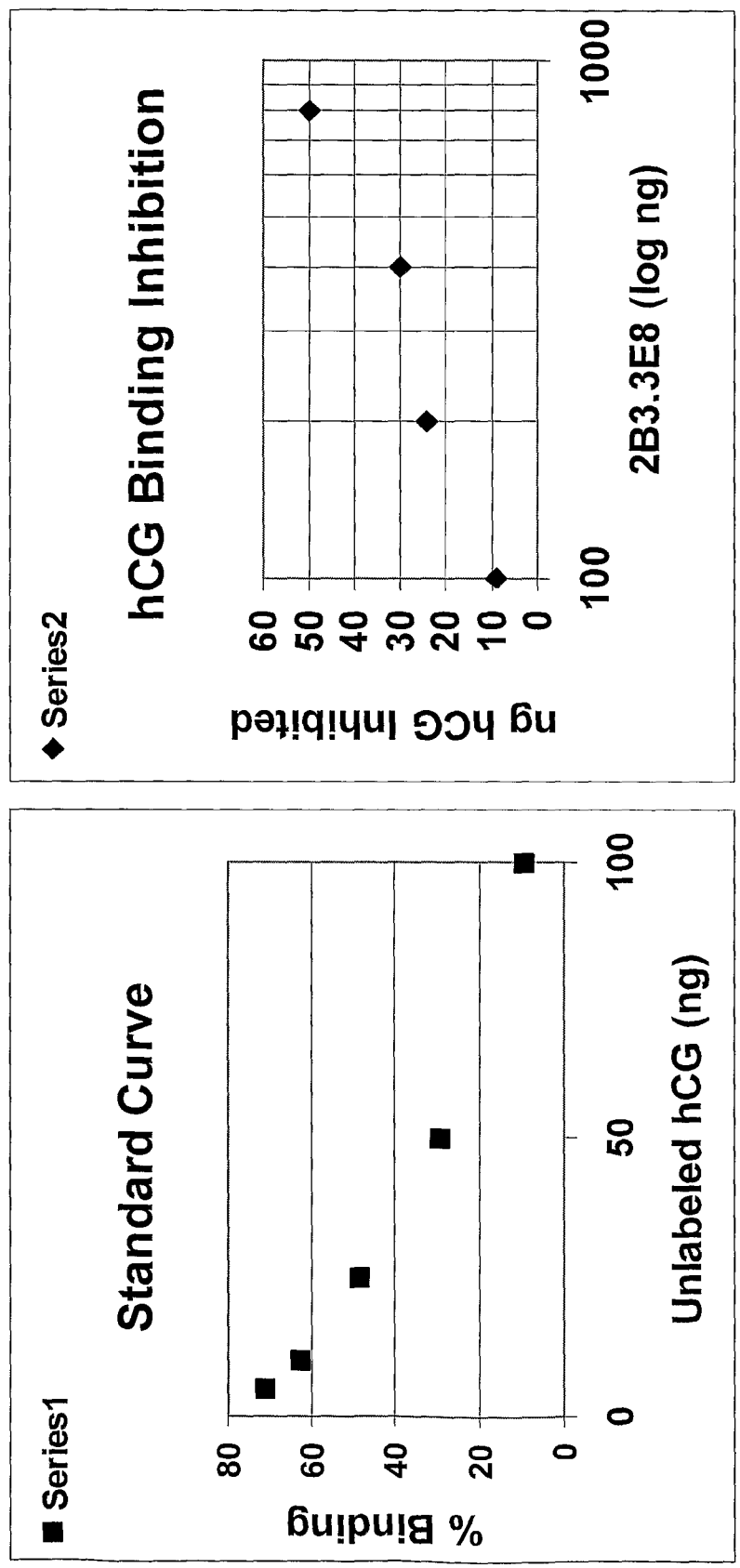

Iodinated hCG (0.25 ng hCG) was incubated with approximately 0.2 milligrams of rat testicular extract in duplicate tubes. This resulted in 28% of the labeled hCG being bound. This was then considered to represent 100% binding to available receptors. FIG. 7 shows as Series 1 an unlabeled hCG standard curve constructed using doses of 5, 10, 25, 50 and 100 ng hCG, all in duplicate tubes with rat testicular extract and 0.25 ng $^{125}$I hCG. As expected, this curve demonstrates that unlabeled hCG competes with labeled hCG for binding to the LH/hCG receptor. Ascending doses of monoclonal antibody 3E8 were then tested for their ability to abrogate inhibition of 0.25 ng $^{125}$I hCG binding to the LH/hCG receptor by 100 ng unlabeled hCG. 100, 200, 400 and 800 ng of monoclonal antibody 3E8 resulted in 12%, 18%, 21% and 29% of control binding, respectively. Reading from the standard curve, these effects imply ng hCG binding inhibition of 9, 24, 30, and 50 ng, respectively. This is shown in FIG. 7 as Series 2. Thus on average monoclonal antibody 3E8 neutralized 88 micrograms of hCG per milligram of antibody. These results demonstrate that a monoclonal antibody specific for the beta-hCG L2 loop demonstrates dose dependent inhibition of hCG binding to the LH/hCG receptor.

Example 8

Effects of Anti-beta-hCG Antibodies on the Growth of Human Tumor Cells

The ability of three anti-beta-hCG antibodies targeting the L2 long loop to modulate the growth of cancer cell lines in vitro was examined. Monoclonal antibodies 3F5, 3E8, 6A11 were generated as described in examples above. Each has both specificity for the L2 long loop of beta-hCG and an IgG1 isotype. A negative control monoclonal antibody was also tested. The negative control was murine monoclonal antibody muromonab-CD3 (OKT3; Orthoclone OKT3; Ortho Biotech Products, LP., Bridgewater, N.J.). These four antibodies were each tested for in vitro activity against the following three cancer cell lines. BXPC-3 pancreatic cancer cells produce beta-hCG but do not express the LH/hCG receptor. MCF-7 breast cancer cells produce relatively little beta-hCG but do express the LH/hCG receptor. HeLa cervical cancer cells produce alpha-hCG and express the LH/hCG receptor but not produce beta-hCG.

$1.0\times10^3$ cells were incubated in triplicate with either 2 or 20 μg of purified monoclonal antibody for 72 hours prior to cell proliferation assays. Two cell proliferation assays with employed. These were based on either cellular reductive capacity (MTS) or intracellular ATP concentration (ATPlite), as described in examples above.

As shown in FIG. 8, each of the anti-beta-hCG monoclonal antibodies inhibited in vitro proliferation of BXPC-3 pancreatic carcinoma cells, known to produce and secrete beta hCG. Inhibition of proliferation was dose dependent with each antibody. In each instance the effect on intracellular ATP concentrations (ATPlite) was greater than the effect on cellular reductive capacity by MTS. By contrast none of the three monoclonal antibodies had any discernible effect on proliferation of either MCF-7 or HeLa cells. As expected, OKT3 had no inhibitory effect on any of the three cell lines (data not shown). Thus anti-beta-hCG antibodies that target the L2 long loop are able as single agents to inhibit proliferation of cells that express beta-hCG but not cells that don't express beta-hCG.

Example 9

Anti-Beta-hCG L2 Loop Antibodies Synergize with Cytotoxic Chemotherapy

Ability of an anti-beta-hCG antibody targeting the L2 long loop to synergize with cytotoxic chemotherapy in modulating growth of cancer cell lines in vitro was also examined. Monoclonal antibody 6F5 was generated as described in examples above. This antibody binds with specificity for the L2 long loop of beta-hCG and also has an IgG1 isotype. A negative control monoclonal antibody was also tested. The negative control was murine monoclonal antibody muromonab-CD3 (OKT3; Orthoclone OKT3; Ortho Biotech Products, L.P., Bridgewater, N.J.). OKT3 is specific for the CD3 antigen found on human T lymphocytes and does not bind to the epithelial cancer cells described below. Monoclonal antibodies 6F5 and OKT3 were tested in combination with two cytotoxic chemotherapy drugs approved by the U.S. Food and Drug Administration (FDA) for treatment of pancreatic and/or breast cancer. Gemcitabine (Gemzar®, Eli Lilly and Company, Indianapolis, Ind.), an antimetabolite, is a fluorine-substituted deoxycitidine analog that received FDA approval for treatment of both advanced pancreatic and metastatic breast cancer. Docetaxel (Taxotere®, Sanofi-Aventis, Bridgewater, N.J.) targets microtubules and is a semi-synthetic taxane that received FDA approval for treatment of breast cancer after failure of prior chemotherapy. BXPC-3 pancreatic cancer cells produce beta-hCG but do not express the LH/hCG receptor. MCF-7 breast cancer cells produce relatively little beta-hCG but do express the LH/hCG receptor.

$1.0 \times 10^3$ cells were incubated in triplicate with 20 μg of purified 6F5 or OKT3 for 24 hours prior to addition of gemcitabine or docetaxel. Final docetaxel concentrations were 0, 1, 3, 10, 30, and 100 nanograms per milliliter. Final gemcitabine concentrations were 0, 5, 10, 20, 40, 80, and 160 nanomolar. After 48 hours of culture in the presence of cytotoxic chemotherapy, cell proliferation was assessed by an assay of intracellular ATP concentration (ATPlite), as described in examples above. Data shown in FIG. 9 are presented as mean percent inhibition of total intracellular ATP for triplicate assays. The data show that an anti-beta-hCG monoclonal antibody which targets the L2 long loop synergizes with cytotoxic chemotherapy in decreasing cell proliferation of cancer cells that are known to produce and secrete beta-hCG.

Pre-treatment with monoclonal antibody 6F5 increased anti-proliferative activity of docetaxel against BXPC-3 cells (p=0.00001, paired t test). Anti-proliferative activity of the antimetabolite gemcitabine was not significantly enhanced. As expected, monoclonal antibody 6F5 increased anti-proliferative activity of neither cytotoxic agent against MCF-7 cells, which do not produce beta-hCG. Taken together, these results indicate that an anti-beta-hCG monoclonal antibody targeting the L2 long loop synergizes with microtubule-targeting, cytotoxic chemotherapy (docetaxel) in diminishing cell proliferation of human cancer cells that produce beta-hCG.

Example 10

Anti-Beta-hCG L2 Loop Antibodies Inhibit Human-Mouse Tumor Xenografts

Ability of an anti-hCG antibody targeting the L2 long loop to modulate growth of cancer cells in vivo was also examined. Monoclonal antibody 6F5 was generated as described in examples above. Monoclonal antibody 6F5 was tested in combination with docetaxel (Taxotere®, Sanofi-Aventis, Bridgewater, N.J.), a semi-synthetic taxane that targets microtubules. BXPC-3 pancreatic cancer cells produce beta-hCG but do not express the LH/hCG receptor. Seven-week-old NCR female athymic nude homozygous (nu/nu) mice (Taconic, Germantown, N.Y.) were inoculated with BXPC-3 human pancreatic carcinoma xenografts. Four experimental groups of ten mice per group were studied. Groups include animals not treated (NT) and animals treated with docetaxel, anti-beta-hCG monoclonal antibody 6F5 alone, or antibody 6F5 plus docetaxel.

Figure 10:
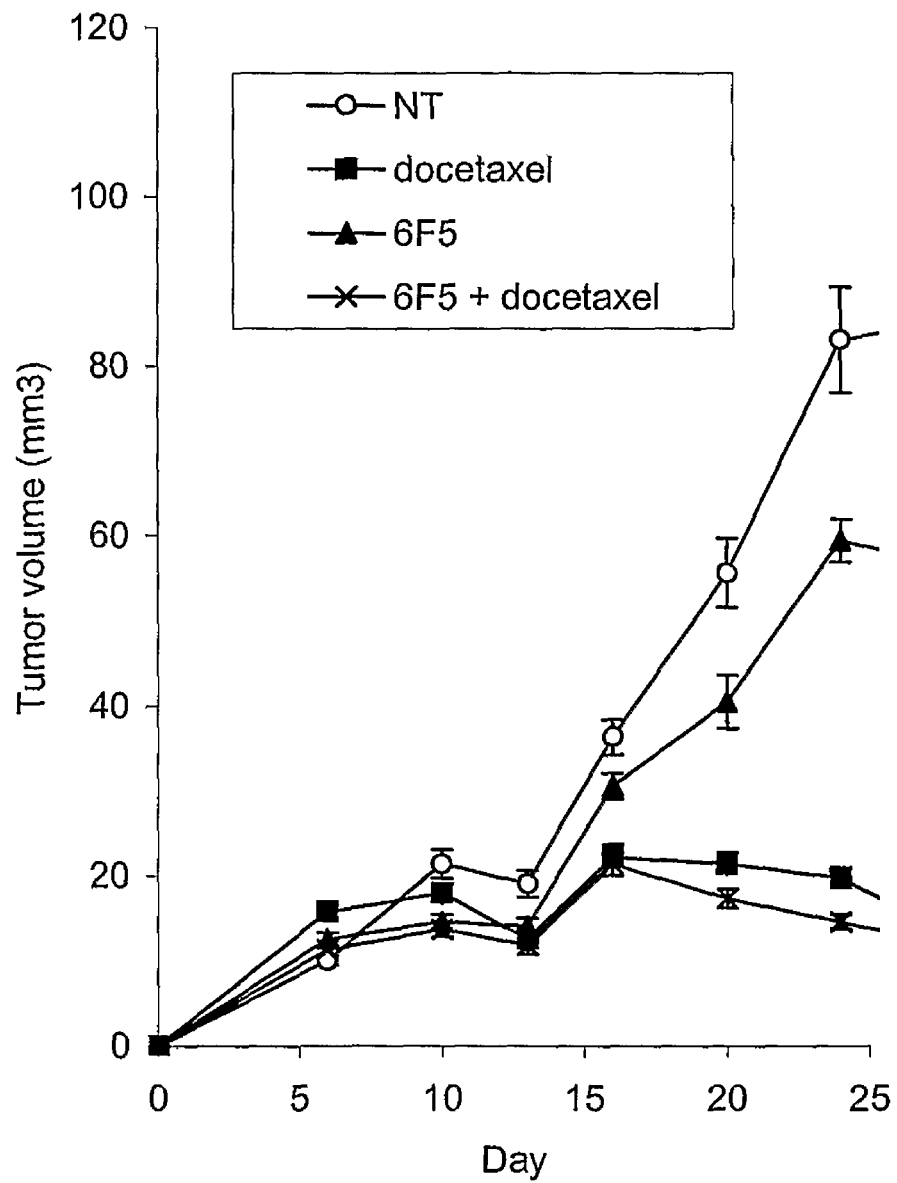

FIG. 10 shows that an anti-beta-hCG monoclonal antibody which targets the L2 long loop is able to diminish tumor growth in vivo, both by itself and in synergy with cytotoxic chemotherapy.

$2 \times 10^6$ cultured BXPC-3 tumor cells were inoculated into the flank in the mid-axillary line of each mouse on Day 1. Animals receiving antibody were given 100 micrograms purified 6F5 via the intraperitoneal route on each of Days 6, 9, 13, 16, 20, and 23. This is twice weekly for three weeks starting on Day 6. Animals receiving chemotherapy were given 30 mg/kg docetaxel via the intraperitoneal route on each of Days 10, 17, and 24. This is weekly for three weeks starting on Day 10. Tumors of all mice were measured bidimensionally with calipers every two to three days. Tumor volume was calculated using the formula (length×width$^2$)÷2. Data shown in FIG. 10 are expressed as mean tumor volume±standard error of the mean (SEM, N=10).

Treatment of mice with the anti-beta-hCG monoclonal antibody 6F5 alone resulted in significant anti-tumor activity in vivo relative to the NT negative control group. (p=0.000001, paired t test). Furthermore, treatment of mice bearing xenografts with antibody 6F5 also improved the anti-tumor activity of docetaxel in vivo relative to docetaxel alone (p=0.00001, paired t test). These results confirm and extend those obtained in vitro. We have shown that a monoclonal antibody directed against the L2 long loop of beta-hCG by itself generates significant anti-tumor activity in vivo against human pancreatic cancer. This anti-tumor activity is coincident with ability of the antibody to block binding of beta-hCG to a cognate receptor on the surface of cancer cells. Furthermore, the monoclonal antibody described synergizes with a separate agent, docetaxel. Docetaxel acts by a distinct mechanism, interference with microtubule function, and is known to be effective for the treatment of cancer. Thus the monoclonal antibody described offers the prospect for generation of a non-toxic cancer therapy that will supplement those already of demonstrable efficacy.

Example 11

DNA and Amino Acid Sequences of Beta-hCG L2 Loop Monoclonal Antibody Heavy Chain FIG. 11 shows DNA and amino acid sequences of mAb 2B2.6F5 heavy chain DNA and amino acid sequence, mAb 2B3.3E8 heavy chain DNA and amino acid sequence, and mAb 2B3.3F5 heavy chain DNA and amino acid sequence. The open reading frame is highlighted. mAb 2B3.3E8 heavy chain amino acid sequence, and mAb 2B3.3F5 heavy chain amino acid sequence show an identical heavy chain sequence.

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference in their entirety.

Those skilled in the art will appreciate that numerous changes and modifications can be made to the embodiments of the invention and that such changes and modifications can be made without departing from the spirit of the invention. It is, therefore, intended that the appended claims cover all such equivalent variations as fall within the true spirit and scope of the invention.

What is claimed:

1. A method of generating a monoclonal antibody specific for the beta-hCG long loop, said method comprises producing a hybridoma cell secreting the monoclonal antibody and isolating the monoclonal antibody, wherein the hybridoma cell is generated from a B cell isolated from an animal immunized with a peptide comprising amino acid residues 38-57 of a human chorionic gonadotropin beta chain, wherein the monoclonal antibody comprises the amino acid sequence of SEQ ID NO:2 or SEQ ID NO:4.

2. The method of claim 1, wherein the peptide is cyclized.

3. The method of claim 1, wherein the peptide is covalently linked to a carrier protein.

4. The method of claim 1, wherein the monoclonal antibody is monoclonal antibody 2B2.6F5 (ATCC Patent Deposit Designation No. PTA-7777).

5. The method of claim 1, wherein the monoclonal antibody is monoclonal antibody 2B3.3E8 (ATCC Patent Deposit Designation No. PTA-7775).

6. The method of claim 3, wherein the carrier protein is diphtheria toxoid.

* * * * *